US010040855B2

(12) United States Patent
Diluzio et al.

(10) Patent No.: US 10,040,855 B2
(45) Date of Patent: Aug. 7, 2018

(54) FORMULATION FOR ANTI-α4β7 ANTIBODY

(75) Inventors: Willow Diluzio, Westford, MA (US); Phoung M. Nguyen, Cambridge, MA (US); Csanad M. Varga, Newton, MA (US); Vaithianathan Palaniappan, Andover, MA (US); Jason Brown, Burlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 103 days.

(21) Appl. No.: 14/114,835

(22) PCT Filed: May 2, 2012

(86) PCT No.: PCT/US2012/036069
§ 371 (c)(1),
(2), (4) Date: Feb. 24, 2014

(87) PCT Pub. No.: WO2012/151247
PCT Pub. Date: Nov. 8, 2012

(65) Prior Publication Data
US 2014/0341885 A1 Nov. 20, 2014

Related U.S. Application Data

(60) Provisional application No. 61/544,054, filed on Oct. 6, 2011, provisional application No. 61/481,522, filed on May 2, 2011.

(51) Int. Cl.
| | | |
|---|---|---|
| *A61K 39/395* | (2006.01) | |
| *C07K 16/28* | (2006.01) | |
| *A61K 9/00* | (2006.01) | |
| *A61K 47/12* | (2006.01) | |
| *A61K 47/14* | (2017.01) | |
| *A61K 47/18* | (2017.01) | |
| *A61K 47/26* | (2006.01) | |
| *A61K 39/00* | (2006.01) | |

(52) U.S. Cl.
CPC ........ *C07K 16/2839* (2013.01); *A61K 9/0019* (2013.01); *A61K 39/39591* (2013.01); *A61K 47/12* (2013.01); *A61K 47/14* (2013.01); *A61K 47/183* (2013.01); *A61K 47/26* (2013.01); *A61K 2039/505* (2013.01); *A61K 2039/54* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,699,880 A | 10/1987 | Goldstein |
| 4,816,397 A | 3/1989 | Boss et al. |
| 4,816,567 A | 3/1989 | Cabilly et al. |
| 5,223,392 A | 6/1993 | Cohen |
| 5,225,538 A | 7/1993 | Capon et al. |
| 5,225,539 A | 7/1993 | Winter |
| 5,258,498 A | 11/1993 | Huston et al. |
| 5,403,919 A | 4/1995 | Butcher |
| 5,428,130 A | 6/1995 | Capon et al. |
| 5,530,101 A | 6/1996 | Queen et al. |
| 5,538,724 A | 7/1996 | Butcher et al. |
| 5,558,864 A | 9/1996 | Bendig et al. |
| 5,565,335 A | 10/1996 | Capon et al. |
| 5,585,089 A | 12/1996 | Queen et al. |
| 5,594,120 A | 1/1997 | Brenner et al. |
| 5,599,676 A | 2/1997 | Vonderheide et al. |
| 5,610,281 A | 3/1997 | Brenner et al. |
| 5,624,321 A | 4/1997 | Snyder |
| 5,624,821 A | 4/1997 | Winter et al. |
| 5,648,260 A | 7/1997 | Winter et al. |
| 5,665,595 A | 9/1997 | Petell et al. |
| 5,688,916 A | 11/1997 | Reid et al. |
| 5,693,761 A | 12/1997 | Queen et al. |
| 5,693,762 A | 12/1997 | Queen et al. |
| 5,714,147 A | 2/1998 | Capon et al. |
| 5,730,978 A | 3/1998 | Wayner |
| 5,821,337 A | 10/1998 | Carter et al. |
| 5,834,021 A | 11/1998 | Spiers |
| 5,840,299 A | 11/1998 | Bendig et al. |
| 5,859,205 A | 1/1999 | Adair et al. |

(Continued)

FOREIGN PATENT DOCUMENTS

| | | |
|---|---|---|
| EP | 0 239 400 A2 | 9/1987 |
| EP | 0303463 A2 | 2/1989 |

(Continued)

OTHER PUBLICATIONS

"Purified Rat Anti-Mouse MAdCAM-1" Technical Data Sheet (BD Pharmingen).
555945, BD Biosciences Pharmingen Integrin b7 BD Biosciences Online Catalog [online], 2005 [retrieved on Apr. 4, 2005]. Retrieved from the Internet: < URL: http://www.bdbiosciences.com/ptProduct.jsp?backLink=ptProductList.jsp&backName=Product%20List&ProId=15874>.
Declaration of Steven B. Landau, M.D. Under 37 CFR 1. 132 as filed in U.S. Appl. No. 08/700,737, Aug. 15, 1996 (Now U.S. Pat. No. 7,147,851, Issued Dec. 12, 2006.).
Adams et al., "Aberrant Homing of Mucosal T Cells and Extra-Intestinal Manifestations of Inflammatory Bowel Disease," Nature, 6:244-251 (2006).
Adams et al., "Complementary DNA Sequencing: Expressed Sequence Tags and Human Genome Project," Science, 252:1651-1656 (1991).

(Continued)

*Primary Examiner* — Yunsoo Kim
(74) *Attorney, Agent, or Firm* — Cristin H. Cowles; Womble Bond Dickinson (US) LLP

(57) ABSTRACT

Antibody formulations are described comprising a mixture of an anti-α4β7 antibody, an antioxidant or chelator, and at least one free amino acid. The disclosed formulations may have improved stability, reduced aggregate formation, or both. The present invention further provides a safe dosing regimen of these antibody formulations that is easy to follow, and which results in a therapeutically effective amount of the anti-α4β7 antibody in vivo.

29 Claims, 18 Drawing Sheets

(56) References Cited

U.S. PATENT DOCUMENTS

| | | | |
|---|---|---|---|
| 5,871,734 | A | 2/1999 | Lobb et al. |
| 5,888,507 | A | 3/1999 | Burkly |
| 5,932,214 | A | 8/1999 | Lobb et al. |
| 6,015,662 | A | 1/2000 | Hackett, Jr. et al. |
| 6,551,593 | B1 | 4/2003 | Ringler et al. |
| 7,147,851 | B1 | 12/2006 | Ponath et al. |
| 9,795,674 | B2 | 10/2017 | Parshad et al. |
| 2002/0147314 | A1 | 10/2002 | Briskin et al. |
| 2002/0172679 | A1 | 11/2002 | Ringler et al. |
| 2004/0009169 | A1 | 1/2004 | Taylor et al. |
| 2004/0023373 | A1 | 2/2004 | Briskin |
| 2005/0095238 | A1 | 5/2005 | Brettman et al. |
| 2006/0159653 | A1 | 7/2006 | Saito et al. |
| 2007/0122404 | A1 | 5/2007 | O'Keefe |
| 2008/0071063 | A1 | 3/2008 | Allan et al. |
| 2010/0098712 | A1* | 4/2010 | Adler .......... A61K 9/0019 424/172.1 |

FOREIGN PATENT DOCUMENTS

| | | |
|---|---|---|
| GB | 2 209 757 A | 5/1989 |
| JP | 06303990 A | 11/1994 |
| JP | 2006249084 A | 9/2006 |
| JP | 2007524602 A | 8/2007 |
| WO | WO-86/01533 A1 | 3/1986 |
| WO | WO-88/07089 A1 | 9/1988 |
| WO | WO-89/07142 A1 | 8/1989 |
| WO | WO-90/07321 A2 | 7/1990 |
| WO | WO-90/07861 A1 | 7/1990 |
| WO | WO-91/03252 A1 | 3/1991 |
| WO | WO-91/09967 A1 | 7/1991 |
| WO | WO-92/11018 A1 | 7/1992 |
| WO | WO-93/02191 A1 | 2/1993 |
| WO | WO-93/15764 A1 | 8/1993 |
| WO | WO-93/23526 A1 | 11/1993 |
| WO | WO-94/12214 A1 | 6/1994 |
| WO | WO-94/13312 A1 | 6/1994 |
| WO | WO-94/16094 A2 | 7/1994 |
| WO | WO-94/17828 A2 | 8/1994 |
| WO | WO-94/29351 A2 | 12/1994 |
| WO | WO-95/19790 A1 | 7/1995 |
| WO | WO-97/18838 A1 | 5/1997 |
| WO | WO-97/25351 A2 | 7/1997 |
| WO | WO-98/06248 A2 | 2/1998 |
| WO | WO-01/78779 | 10/2001 |
| WO | 2004016286 A2 | 2/2004 |
| WO | 2004055164 A2 | 7/2004 |
| WO | 2007/007159 A2 | 1/2007 |
| WO | 2007124299 A2 | 11/2007 |
| WO | WO-2008/071394 | 6/2008 |
| WO | WO-2009/009407 | 1/2009 |
| WO | 2009141239 A1 | 11/2009 |
| WO | 2010107752 A2 | 9/2010 |
| WO | 2010107752 A3 | 9/2010 |
| WO | 2012/151248 A2 | 11/2012 |

OTHER PUBLICATIONS

Adams et al., "Initial Assessment of Human Gene Diversity and Expression Patterns Based Upon 83 Million Nucleotides of cDNA Sequence," Nature (Supp), 377:3-174 (1995).
Adams et al., "Sequence Identification of 2,375 Human Brain Genes," Nature, 355:632-633 (1992).
Andrew et al., "Distinct but Overlapping Epitopes are Involved in α4β7-Mediated Adhesion to Vascular Cell Adhesion Molecule-1, Mucosal Addressin-1, Fibronectin, and Lymphocyte Aggregation," J. of Immunology, 153:3847-3861 (1994).
Andrew et al., "TABS, A T Cell Activation Antigen that Induces LFA-1-Dependent Aggregation," The Journal of Immunology, 155:1671-1684 (1995).
Aruffo et al., "Molecular Cloning of a CD28 cDNA by a High-Efficiency COS Cell Expression System," Proc. Natl. Acad. Sci. USA, 84:8573-8577 (1987).
ATCC No. HB-293, FIB504.64, ATCC Cell Biology Catalog [online], 2005 [retrieved on May 27, 2005]. Retrieved from Internet: <URL: http://www.atcc.org/common/catalog/numSearch/numResults.cfm?atccNum=HB-293>.
Bednarczyk et al., "Identification of a Combinatorial Epitope Expressed by the Integrin α4I3β7 Heterodimer Involved in the Regulation of Cell Adhesion," J. Biol. Chem., 289(11):8348-8354 (1994).
Bendig, "Humanization of Rodent Monoclonal Antifbodies by CDR Grafting," Methods: A Companion to Methods in Enzymology, 8:83-93 (1995).
Berg et al., "L-Selectin-Mediated Lymphocyte Rolling on MAdCAM-1," Nature, 366:695-698 (1993).
Berlin et al., "α4 Integrins Mediate Lymphocyte Attachment and Rolling under Physiological Flow," Cell, 80:413-422 (1995).
Berlin et al., "α4β7 Integrin Mediates Lymphocyte Binding to the Muscosal Vascular Addressin MAdCAM-1," Cell, 74:185-195 (1993).
Bloom, et al., "Adhesion Molecule Expression in Primary Sclerosing Cholangitis and Primary Biliary Cirrhosis," Gut, 36:604-609 (1995).
Bozic C.R., et al., "The Murine Interleukin 8 Type B Receptor Homologue and Its Ligands," J. Biol. Chem., 269:29355-29358 (1994).
Briskin et al., "Structural Requirements for Mucosal Vascular Addressin Binding to its Lymphocyte Receptor α4β7," J. Immunol., 156:719-726 (1996).
Briskin, M.J., et al., "MAdCAM-1 Has Homology to Immunoglobulin and Mucin-Like Adhesion Receptors and to IgA1," Nature, 363:461-463 (1993).
Brossay et al., "Mimicry of a Neutralizing Epitope of the Major Outer Membrane Protein of Chlamydia Trachomatis by Anti-Idiotypic Antibodies," Infection and Immunity, 62:341-347 (1994).
Brown, J., et al., "Critical Evaluation of ECV304 as a Human Endothelial Cell Model Defined by Genetic Analysis and Functional Responses: A Comparison with the Human Bladder Cancer Derived Epithelial Cell Line T24/83," Laboratory Investigation, 80:37-45 (2000).
Calvete et al., "Further Studies on the Topography of Human Platelet Glycoprotein IIb," Biochem, 273:767-775 (1991).
Carr et al., "Monocyte Chemoattractant Protein 1 Acts as a T-lymphocyte Chemoattractant," Proc. Natl. Acad. Sci. USA, 91:3652-3656 (1994).
Chenna et al., "Multiple Sequence Alignment with the Clustal Series of Programs," Nucleic Acids Research, 31:3497-3500 (2003).
Chensue et al., "Monocyte Chemotactic Protein Expression During Schistosome Egg Granuloma Formation," Am. J. of Pathology, 146(1):130-138 (1995).
Cleland et al., "A Specific Molar Ratio of Stabilizer to Protein is Required for Storage Stability of a Lyophilized Monoclonal Antibody," Journal of Pharmaceutical Sciences, 90:310-321 (2001).
Cooper et al., "Clinicopathologic Study of Dextran Sulfate Sodium Experimental Murine Colitis," Laboratory Investigations, 69(2):238-249 (1993).
Creyghton, W.M., et al., "Cytokine-Mediated Modulation of Integrin, ICAM-1 and CD44 Expression on Human Uveal Melanoma Cells in Vitro," Melanoma Research, 5:235-242 (1995).
De Fougerolles et al., "Intercellular Adhesion Molecule 3, A Third Adhesion Counter-Receptor for Lymphocyte Function-associated Molecule 1 on Resting Lymphocytes," J. Exp. Med., 175:185-190 (1992).
Declaration from Erik Fedyk filed in Opposition of EP Patent No. 0 808 367 (2009).
Declaration from Michael Briskin filed in Opposition of EP Patent No. 0 808 367 (2009).
Declaration from Vilmos Csizmadia filed in Opposition of EP Patent No. 0 808 367 (2009).
Dignass et al., "New Developments in the Management of Steroid-Refractory Inflammatory Bowel Disease," Business Briefing: European Gastroenterology Review, pp. 1-5 (2005).

(56) References Cited

OTHER PUBLICATIONS

Dirks, W.G., et al., Letter to the Editor, "ECV304 (Endothelial) Is Really T24 (Bladder Carcinoma): Cell Line Cross-Contamination at Source," In Vitro Cell Dev. Biol. Animal, 35:558-559 (1999).
Dowbenko, D., et al., "Cloning of a Rat Homologue of Mouse GlyCAM 1 Reveals Conservation of Structural Domains," J. Biol. Chem., 268: 14399-14403 (1993).
Dueñas et al., "Clonal Selection and Amplification of Phage Displayed Antibodies by Linking Antigen Recognition and Phage Replication," Bio/Technology, 12:999-1002 (1994).
Erle et al., Expression and Function of the MAdCAM-1 Receptor, Integrin α4β7, on Human Leukocyes,: J. of Immunology, 153:517-528 (1994).
Feagan et al., "An Ascending Dose Trial of a Humanized α4/β7 Antibody in Ulcerative Colitis(UC)," Gastroenterol. ,118(4): α4/β7, (Abstract No. 4851), (2000).
Feagan et al., "Treatment of Active Crohn's Disease with MLN0002, a Humanized Antibody to the alpha4beta7 Integrin", Clin Gastroenterol Hepatol., Dec. 2008;6(12):1370-7 (Abstract only).
Feagan et al., "Treatment of Ulcerative Colitis with a Humanized Antibody to the α4β7 Integrin," The New England Journal of Medicine, 352:2499:2507 (2005).
Feagan, et al., "Emerging Safety Profile of Vedolizumab: A Novel, Selective Integrin Inhibitor for the Treatment of IBD," 15(S2): S12, Abstract P-0025, 2009 IBD Abstracts (2009).
Feagan et al., "Vedolizumab as Induction and Maintenance Therapy for Ulcerative Colitis," The New England Journal of Medicine, 369(8):699-710 (Aug. 22, 2013).
Federlin, "Immunological aspects of inflammatory bowel diseases," Immun. Infekt., 6:15-27 (1978) (abstract only).
Fedyk, et al., "Regional Immunomodulation of the Gastrointestinal Tract Without Systemic Immunosuppression in Cynomolgus Macaques by Vedolizumab," 15(S2): S50, Abstract P-0144, 2009 IBD Abstracts (2009).
Forrester, J.V., and Leckie, J.M., "Adhesion of Neutrophil Leucocytes Under Conditions of Flow," J. Cell Sci., 70:93-110 (1984).
Goldenberg, D.M., "New Developments in Monoclonal Antibodies for Cancer Detection and Therapy," CA Cancer J. Clin., 44:43-64 (1994).
Gordon et al., "Randomised Double-Blind Placebo-Controlled Trial of Recombinant Humanised Antibody to α4 Integrin (Antegren™) in Active Crohn's Disease," Gastroenterology, 116(4) Part 2:A726 (1999).
Gordon, "Treatment of Active Ulcerative Colitis with a Recombinant Humanised Antibody to α4 integrin (Antegren™), "Gastroenterology, 116(4) Part 2:A726 (1999).
Gorman et al., "Humanisation of Monoclonal Antibodies for Therapy," Sem. Immunol., 2(6):457-466 (1990).
Grant et al., "MAdCAM-1 Expressed in Chronic Inflammatory Liver Disease Supports Mucosal Lymphocyte Adhesion to Hepatic Endothelium (MAdCAM-1 in Chronic Inflammatory Liver Disease)," Hepatology, 33:1065-1072 (2001).
Hall, D.E., et al., "The $α_1/β_1$ and $α_6/β_1$ Integrin Heterodimers Mediate Cell Attachment to Distinct Sites on Laminin," J. Cell Biol., 110:2175-2184 (1990).
Hamann et al., "Role of a4-Integrins in Lymphocyte Homing to Mucosal Tissues in Vivo," Journal of Immunology, 152:3282-3293 (1994).
Hänninen A., et al., "Vascular Addressins Are Induced on Islet Vessels during Insulitis in Nonobese Diabetic Mice and Are Involved in Lymphoid Cell Binding to Islet Endothelium" J. Clin Invest., 92(5):2509-2515 (1993).
Harris et al., "Therapeutic Antibodies—The Coming of Age," TIBTECH 11:42-44 (1993).
Herlyn et al., "Anti-Idiotypic Antibodies Bear the Internal Image of a Human Tumor Antigen," Science 232:100-102 (1986).

Hession et al., "Endothelial Leukocyte Adhesion Molecule 1: Direct Expression Cloning and Functional Interactions," Proc. Natl. Acad. Sci. USA, 87:1673-1677 (1990).
Hesterberg et al., "Rapid Resolution of Chronic Colitis in the Cotton-Top Tamarin with an Antibody to a Gut-Homing Integrin α4β7," Gastroenterology, 111:1373-1380 (1996).
Higgins, D.G., et al., "Using CLUSTAL for Multiple Sequence Alignments," Methods in Enzymology, 266:383-402 (1996).
Higgins, D.H , Sharp, P.M., "CLUSTAL; A Package for Performing Multiple Sequence Alignment on a Microcomputer," Gene, 73:237-244 (1988).
Hoentjen et al., "Safety of Anti-Tumor Necrosis Factor Therapy in Inflammatory Bowel Disease," World Journal of Gastroenterology, 15(17):2067-2073 (2009).
Holzmann, B., et al., "Identification of a Murine Peyer's Patch-Specific Lymphocyte Homing Receptor as an Integrin Molecule with an α Chain Homologous to Human VLA-4α," Cell, 56:37-46 (1989).
Hu, M. C-T et al., "Cloning and Expression of Mouse Integrin $β_p(β_7)$: A functional Role in Path-Specific Lymphocyte Homing," Proc. Natl. Acad. Sci., 89:8254-8258 (1992).
Huffnagle et al., "The Role of Monocyte Chemotactic Protein-1 (MCP-1) in the Recruitment of Monocytes and CD4 $^+$T Cells During a Pulmonary Cryptococcus Neoformans Infection," J. of Immunology, 155:4790-4797 (1995).
Hynes, "Integrins: Versatility, Modulation, and Signaling in Cell Adhesion," Cell, 69:11-25 (1992).
Information for Contributions: J. Immunol., 151(11) (1993).
Katz, "Medical and Surgical Management of Severe Colitis," Seminars in Gastrointestinal Disease, 11(1):18-32 (2000).
Katz, "Update in Medical Therapy in Inflammatory Bowel Disease: A Clinician's View," Digestive Diseases, 17:163-171 (1999).
Kettleborough et al., "Humanization of a Mouse Monoclonal Antibody by CDR-Grafting: The Importance of Framework Residues on Loop Conformation," Protein Engng., 4(7):773-783 (1991).
Kola, et al., "Can the Pharmaceutical Industry Reduce Attrition Rates?", Nature Reviews, Drug Discovery, Aug. 2004, pp. 711-715, vol. 3.
Lang, "Promising New Agents for the Treatment of Inflammatory Bowel Disorders," Drugs R&D, 1(3): 237-244 (1999).
Lazarovits et al., "Differential Expression in Rheumatoid Synovium and Synovial Fluid of α4β7 Integrin—A Novel Receptor for Fibronectin and Vascular Cell Adhesion Molecule-1," J. Immunol., 151(11):6482-6489 (1993).
Lazarovits et al., "Lymphocyte Activation Antigens-I. A Monoclonal Antibody, Anti Act 1, Defines a New Late Lymphocyte Activation Antigen," J. Immunol., 133:1857-1862 (1984).
Lazarovits et al., "α4β7 Integrin in Rheumatoid Arthritis," In Leukocyte Typing V-White Cell Differentiation Antigens, S.F. Schlossman et al., eds., (Oxford: Oxford University Press), pp. 1686-1687 (1995).
Lazarovits, et al., "A Monoclonal Antibody, Anti-Act I, Defines a New Late Lymphocyte Activation Antigen," J. of Immunology, 133(4):1857-1862 (1984).
Lederman et al., "A Single Amino Acid Substitution in a Common African Allele of the CD4 Molecule Ablates Binding of the Monoclonal Antibody, OKT4," Molec. Immunol., 28:1171-1181 (1991).
Leung et al., "Cloning of the Mucosal Addressin MAdCAM-1 from Human Brain: Identification of Novel Alternatively Spliced Transcripts," Immunology and Cell Biology, 74:490-496 (1996).
Lin Ko-Chung et al., "Very Late Antigen 4 (VLA4) Antagonists as Anti-Inflammatory Agents," Current Opinion in Chemical Biology, 2(4):453-457 (1998).
Lobb et al., The Role of α4β7 Integrins in Lung Pathophysiology, Eur. Respir. J., 9 (Supp 22):104s-108s (1996).
Loetscher et al., "Monocyte Chemotactc Proteins MCP-1, MCP-2, and MCP-3 are Major Attractants for Human CD4 $^+$ and CD8$^{+a}$T Lymphocytes," FASEB J., 8:1055-1060 (1994).
Marehbian et al., Adverse Events Associated with Common Therapy Regimens for Moderate-to-Severe Crohn's Disease, The American Journal of Gastroenterology, 104:2524-2533 (2009).

(56) References Cited

OTHER PUBLICATIONS

Marlin et al., "Purified Intercellular Adhesion Molecule-1 (ICAM-1) is a Ligand for Lymphocyte Function-Associated Antigen 1 (LFA-1)," Cell, 51:813-819 (1987).
Mawhorter et al., "Identification of Surface Molecules Associated with Physiologic Activation of Eosinophils. Application of Whole-Blood Flow Cytometry to Eosinophils," J. Immunol., 156:4851-4858 (1996).
MacDonald, et al., "Selective Biopsy of Human Peyer's Patches During Ileal Endoscopy," Gastroenterology, 93:1356-1362 (1987) (abstract only).
McLure, M.A., et al., "Comparative Analysis of Multiple Protein-Sequence Alignment Methods," Mol. Biol. Evol. 11(4):571-592 (1994).
Michie et al., "The Human Peripheral Lymph Node Vascular Addressin, An Inducible Endothelial Antigen Involved in Lymphocyte Homing," American Journal of Pathology, 143(6):1688-1698 (1993).
Mountain, A. and Adair, J.R., "Engineering Antibodies for Therapy," Biotechnol. Genet. Eng. Rev., 10:1-1412 (1992).
Nakache, et al., "The Mucosal Vascular Addressin is a Tissue-Specific Endothelial Cell Adhesion Molecule for Circulating Lymphocytes," Nature, 337:179-181 (1989).
Ngo et al., "Chapter 14," in The Protein Folding Problem and Tertiary Structure Predication, Merz et al., eds. (Boston: Birkhauser), pp. 491-495 (1994).
Nieto et al., "Expression of Functionally Active α4β1 Integrin by Thymic Epithelial Cells," Clin. Exp. Immunol. 106:170-178 (1996).
O'Kennedy et al., "Antibody Engineering: An Overview," Essays Biochem., 26:59-75 (1991).
Okayasu et al., "A Novel Method in the Induction of Reliable Experimental Acute and Chronic Ulcerative Colitis in Mice," Gastroenterology, 98:694-702 (1990).
Olson, T.S., and Ley, K., "Chemokines and Chemokine Receptors in Leukocyte Trafficking," Am. J. Physiol. Regulatory Integrative Comp Physiol., 283:R7-R28 (2002).
Osband et al., "Problems in the Investigational Study and Clinical use of Cancer Immunotherapy," Immunol. Today, 11(6):193-195 (1990).
Osband et al., "Problems in the Investigational Study and Clinical use of Cancer Immunotherapy," Immunol. Today, 11:103-105 (1990).
Osborn et al., "Direct Expression Cloning of Vascular Cell Adhesion Molecule 1, A Cytokine-Induced Endothelial Protein that Binds to Lymphocytes," Cell, 59:1203-1211 (1989).
Osborn, L., et al., "Arrangement of Domains, and Amino Acid Residues Required for Binding of Vascular Cell Adhesion Molecule-1 to Its Counter-Receptor VLA-4 ($\alpha_4\beta_1$)," J. Cell Biol., 124:601-608 (1994).
Owens et al., "The Genetic Engineering of Monoclonal Antibodies," J. Immunol. Methods, 168(2):149-165 (1994).
Page et al., "High Level Expression of the Humanized Monoclonal Antibody Campth-1 H in Chinese Hamster Ovary Cells," Bio/Technology, 9:64-68 (1991).
Pals et al., "Expression of the Mucosal Homing Receptor α4β7 in Malignant Lymphomatous Polyposis of the Intestine," Gastroenterology, 107:1519-1523 (1994).
Pan, J., et al., "Comparison of Promoters for the Murine and Human P-Selectin Genes Suggests Species-Specific and Conserved Mechanisms for Transcriptional Regulation in Endothelial Cells," J. Biol. Chem., 273:10058-10067 (1998).
Panitch, H.S., et al., "Exacerbations of Multiple Sclerosis in Patients Treated with Gamma Interferon," The Lancet 1(8538):893-895 (1987).
Parikh et al., "P130 Gastrointestinal Selectivity of Vedolizumab (MLN0002), A Humanized Monoclonal Antibody to Alpha 4beta 7 Integrin," Journal of Crohn's and Colitis, 3:S62 (2009).
Parikh et al., "No Increase in JC Viermia, Lymphocyte Count, or Circulating CD34+Hmeatopoietic Progenitor Cells After Treatment With Vedolizumab, A Humanized Monoclonal Antibody to α4/β7 Integrin," Gastroenterology, 138:S145-S146 (2010).
Parikh et al., "Vedolizumab for the Treatment of Active Ulcerative Colitis: A Randomized Controlled Phase 2 Dose-ranging Study," Inflamm. Bowel Dis., 18(8):1470-1479 (2012).
Parker et al., "A Family of β7 Integrins on Human Mucosal Lymphocytes," Proc. Natl. Acad. Sci. USA, 89:1924-1928 (1992).
Pennica et al., "Expression Cloning of Cardiotrophin 1, A Cytokine that Induces Cardiac Myocyte Hypertrophy," Proc. Natl. Acad. Sci., 92:1142-1146 (1995).
Petrovic et al., "LPAM ($\alpha_4\beta_7$Integrin) is an Important Homing Integrin on Alloreactive T Cells in the Development of Intestinal Graft-Versus-Host Disease," Blood, 103:1542-1547 (2004).
Philip, et al., "Value of Novelty?", Nature Reviews, Drug Discovery, Aug. 2002, pp. 571-572, vol. 1.
Picker et al., "Physiological and Molecular Mechanisms of Lymphocyte Homing," Annu. Rev. Immunol., 10:561-591 (1992).
Podolsky, "Inflammatory Bowel Disease (First of Two Parts)," The New England Journal of Medicine, 325(13):928-937 (1991).
Podolsky, "Inflammatory Bowel Disease (Second of Two Parts)," The New England Journal of Medicine, 325(14):1008-1016 (1991).
Podolsky, D.K. et al., "Attenuation of Colitis in the Cotton-Top Tamarin by Anti-$a_4$ Integrin Monoclonal Antibody," J. Clin. Invest., 92:372-380 (1993).
Postigo et al., "α4β7 Integrin Mediates B-Cell Binding to Fibronectin and Vascular Cell Adhesion Molecule-1," J. Immunol, 151(5):2471-2483 (1993).
Prakash et al., "Cloning and Analysis of Murine cDNA that Encodes a Fibrogenic Lymphokine, Fibrosin," Proc. Natl. Acad. Sci. USA, 92:2154-2158 (1995).
Prasad et al., "Evaluation of Mutagenesis for Epitope Mapping," The Journal of Biological Chemistry, 15:10705-10708 (1993).
Present, "How to do Without Steroids in Inflammatory Bowel Disease," Inflammatory Bowel Diseases, 6(1):48-57 (2000).
Pritsch et al., Can Immunoglobulin C.sub.H1 Constant Region Domain Modulate Antigen Binding Affinity of Antibodies? J. Clin. Invest., 98:2235-2243 (1996).
Pulido et al., "Functional Evidence for Three Distinct and Independently Inhibitable Adhesion Activities Mediated by the Human Integrin VLA-4," J. Biol. Chem. 266(16):10241-10245 (1991).
Reichert, "Antibody-Based Therapeutics to Watch in 2011," MABS, 3:76-99 (2011).
Reichmann et al., "Reshaping Human Antibodies for Therapy," Nature, 332:323-327 (1988).
Rice, G.E., et al., "Vascular and Nonvascular Expression of INCAM-110; A Target for Mononuclear Leukocyte Adhesion in Normal and Inflamed Human Tissues," Am. J. of Pathology, 138:385-393.
Ringler, et al., "Cellular Localization of Simian Immunodeficiency Virus in Lymphoid Tissues I. Immunohistochemistry and Electron Microscopy," American Journal of Pathology, 134(2):373-383 (1989).
Roberts et al., "The Mucosal T-Cell Integrin $\alpha_{M290}\beta_7$ Recognizes a Ligand on Mucosal Epithelial Cell Lines," Eur. J. Immunol., 23:1630-1635 (1993).
Rott et al., "Expression of Mucosal Homing Receptor α4β7 by Circulating CD4+ Cells with Memory for Intestinal Rotavirus," J. Clin Invest., 100(5):1204-1208 (1997).
Rudikoff et al., "Single Amino Acid Substitution Altering Antigen-Binding Specificity," Proc. Natl. Acad. Sci. USA, 79:1979-1983 (1982).
Rudinger, "Characteristics of the Amino Acids as Components of a Peptide Hormone Sequence," in Peptide Hormones, Parsons, J.A. (Ed.), University Park Press, Baltimore, M.D., p. 1-7 (1976).
Rudinger, In Peptide Hormones, Parsons, J.A., ed., (University Park Press, Baltimore MD) pp. 1-7 (1976).
Rutgeerts, "Review Article: Efficacy of Infliximab in Crohn's Disease-Induction and Maintenance of Remission," Aliment Pharmacol. Ther., 13(Suppl. 4):9-15 (1999).
Rutgeerts, "Summary," Aliment Pharmacol. Ther., 13(Suppl. 4):38 (1999).
Sachar, "How to do Without Steroids in Inflammatory Bowel Disease," Inflammatory Bowel Diseases, 6(1):58 (2000).

(56) References Cited

OTHER PUBLICATIONS

Sadlack et al., "Ulcerative Colitis-Like Disease in Mice with a Disrupted Interleukin-2 Gene," Cell, 75:253-261 (1993).
Salmi et al., "Aberrant Binding of Lamina Propia Lymphocytes to Vascular Endothelium in Inflammatory Bowel Diseases," Gastroenterology, 106:596-605 (1994).
Salmi et al., "Dual Binding Capacity of Mucosal Immunoblasts to Mucosal and Synovial Endothelium in Humans: Dissection of Molecular Mechanisms," J. Exp. Med., 181:137-149 (1995).
Sánchez et al., "VLA-3: A Novel Polypeptide Associate Within the VLA Molecular Complex: Cell distribution and Biochemical Characterization," Eur. J. Immunol., 16:1343-1349 (1986).
Sandborn et al., "Vedolizumab as Induction and Maintenance Therapy for Crohn's Disease," The New England Journal of Medicine, 369(8):711-721 (Aug. 22, 2013).
Santa Cruz Biotechnology Inc., ECV304 Human Whole Cell Lysate (sc-2269) Technical Datasheet.
Santa Cruz Biotechnology Inc., MAdCAM-1 siRNA (h) Technical Datasheet.
Santa Cruz Biotechnology, Inc. MAdCam-1 (Meca-367): sc-19604, www.scbt.com, obtained Sep. 25, 2007.
Scholz et al., "Clinical Pharmacology of Vedolizumab in Patients with Active Ulcerative Colitis," ECCO Annual Meeting Hamburg Germany (2009).
Schulz et al., Proteolytic Cleavage of CD25, the α Subunit of the Human T Cell Interleukin 2 Receptor, by Der p. 1, a Major Mite Allergen with Cysteine Protease Activity, J. Exp. Med., 187:271-275 (1998).
Schweighoffer et al., "Selective Expression of Integrin $\alpha_4\beta_7$ on a Subset of Human CD4+ Memory T Cells with Hallmarks of Gut-Trophism," The Journal of Immunology, 151:717-729 (1993).
Sela, "Overview: Antigens," In Handbook of Exp. Immunol., Immunochemistry, Weir et al., ed. Balckwell Sci. Pub., pp. 1.1-1.7 (1986).
Shaw et al., "Molecular Cloning of the Human Mucosal Lymphocyte Integrin $\alpha^E$ Subunit," J. Biol. Chem. 269(5):6016-6025 (1994).
Shaw et al., "Mouse/Human Chimeric Antibodies to a Tumor-Associated Antigen: Biologic Activity of the Four Human IgG Subclasses," J. Natl. Cancer Inst., 80:1553-1559 (1988).
Shiner, "Immunopathology of the Digestive Apparatus in Infancy," Pediatr. Med. Chir. 4:359-364 (1982) (abstract only).
Shyjan et al., "Human Mucosal Addressin Cell Adhesion Molecule-1 (MAdCAM-1) Demonstrates Structural and Functional Similarities to the α4β7-Integrin Binding Domains of Murine MadCAM-1, but Extreme Divergence of Mucin-like Sequences," J. of Immunology, 156:2851-2857 (1996).
Silber et al, "Recruitment of Lymphocytes During Cutaneous Delayed Hypersensitivity in Nonhuman Primates is Dependent on E-Selectin and Vascular Cell Adhesion Molecule 1," J. Clin. Invest., 93:1554-1563 (1994).
Springer et al., "Leukocyte Typing V White Cell Differentiation Antigens, vol. II," Oxford University Press, pp. 1443-1456 (1995).
Springer, "The Sensation and Regulation of Interactions with the Extracellular Environment: The Cell Biology of Lymphocyte Adhesion Receptors," Annu. Rev. Cell Biol., 6:359-402 (1990).
Springer, "Traffic Signals for Lymphocyte Recirculation and Leukocyte Emigration: The Multistep Paradigm," Cell, 76:301-314 (1994).
Staunton, DE, et al., "Functional cloning of ICAM-2, a Cell Adhesion Ligand for LFA-1 Homologous to ICAM-1," Nature, 339(6219):61-64 (1989).
Streeter, P.R.E.L., et al., "A Tissue-Specific Endothelial Cell Molecule Involved in Lympocyte Homing," Nature, 331:41-46 (1988).
Strober et al., "Chronic Intestinal Inflammation: An Unexpected Outcome in Cytokine or T-Cell Receptor Mutant Mice," Cell, 75:203-205 (1993).
Tang, D.G., et al., "Phenotypic Properties of Cultured Tumor Cells: Integrin α11β3 Expression, Tumor-Cell-Induced Platelet Aggregation, and Tumor-Cell Adhesion to Endothelium as Important Parameters of Experimental Metastasis," Int. J. Cancer, 54:338-347 (1993).
Taub et al., "Monocyte Chemotactic Protein-1 (MCP-1), -2 and -3 are Chemotactic for Human T Lymphocytes," J. of Clin. Investigation, 95:1370-1376 (1995).
Teague et al., "Integrin α4β7 Co-Stimulation in Human Peripheral Blood T-Cell Proliferation," Cell Ad. Comm., 2:539-547 (1994).
Thompson, J.D., et al., "CLUSTAL W: Improving the Sensitivity of Progressive Multiple Sequence Alignment through Sequence Weighting, Position-Specific Gap Penalties and Weight Matrix Choice," Nucleic Acids Res., 22:4673-4680. (1994).
Thorpe, S.J., and T. Feizi, "Species Differences in the Expression of Carbohydrate Differentiation Antigens on Mammalian Blood Cells Revealed by Immunoflurescence with Monoclonal Antibodies," Bioscience Reports, 4:673-685 (1984).
Tidswell et al., "Structure-Function Analysis of the Integrin β7 Subunit," J. Immunol., 159:1497-1505 (1997).
Tiisala et al., "$\alpha_E\beta_7$ and α4β7 Integrins Associated with Intraepithelial and Mucosal Homing are Expressed in Macrophages," Eur. J. Immunol., 25:411-417 (1995).
Toruner et al., "Risk Factors for Opportunistic Infections in Patients with Inflammatory Bowel Disease," Gastroenterology, 134:929-936 (2008).
Tromm et al., "Oral Mesalazine for the Treatment of Crohn's Disease: Clinical Efficacy with Respect to Pharmacokinetic Properties," Hepato-Gastroenterology, 46:3124-3135 (1999).
Van der Voort et al., "Paracrine Regulation of Germinal Center B Cell Adhesion Through the c-Met-Hepatocyte Growth Factor/Scatter Factor Pathway," J. Exp. Med., 185(12):2121-2131 (1997).
Vasiliauskas, "An Open-Label Pilot Study of Low-Dose Thalidomide in Chronically Active, Steroid-Dependant Crohn's Disease," Gastroenterology, 117:1278-1287 (1999).
Waldmann, "Monoclonal Antibodies in Diagnosis and Therapy," Science, 252:1657-1662 (1991).
Wan et al., "Expression of α4β7 Integrin on Eosinophils and Modulation of α4-Integrin-Mediated Eosinophil Adhesion via CD4," Int. Arch. Allergy Immunol., 107:343-344 (1995).
Webster's II New Riverside Dictionary, The Riverside Publishing Company, p. 755, (1988).
Winter et al., "Humanized Antibodies," Immunol. Today, 14(6):243-246 (1993).
Woodside et al., "Specific Inhibition of T Lymphocyte Coactivation by Triggering Integrin β1 Reveals Convergence of β2 and β7 Signaling Pathways," J. Immunol., 157:700-706 (1996).
Wu, N.W., et al., "Evolutionary Conservation of Tissue-specific Lymphocyte-Endothelial Cell Recognition Mechanisms Involved in Lymphocyte Homing," J. Cell Biol., 107(5):1845-1851 (1998).
Yacyshyn et al., "Crohn's Disease, Ulcerative Colitis, and Normal Intestinal Lymphocytes Express Integrins in .Dissimilar Patterns," Gastroenterology, 107:1364-1371 (1994).
Yang et al., "Construction and Adhesion Properties of a Soluble MAdCAM-1-Fe Chimera Expressed in a Baculovirus System: Phylogenetic Conservation of Receptor-Ligand Interation," Scand. J. Immunol., 42:235-247 (1995).
Yang et al., "Involvement of $\beta_7$ Integrin and Mucosal Addressin Cell Adhesion Molecule-1 (MAdCAM-1) in the Development of Diabetes in Nonobese Diabetic Mice," Diabetes, 46;1542-1547 (1997).
Yuan et al., "Cloning and Sequence Analysis of a Novel b2—Related Integrin Transcript from T Lymphocytes: Homology of Integrin Cysteine-Rich Repeats to Domain III of Laminin B Chains," International Immunology, 2:1097-1108 (1990).
Yuan et al., "Cloning and Sequence Analysis of a Novel b2 -Related Integrin Transcript from T Lymphocytes: Homology of Integrin Cysteine-Rich Repeats to Domain III of Laminin B Chains," International Immunology, 3:1373-1374 (1990).
Yuan et al., "Human Peripheral Blood Eosinophils Express a Functional C-Kit Receptorfor Stem Cell Factor that Stimulates Very Late Antigen 4 (VLA-4)-Mediated Cell Adhesion to Fibronectin and Vascular Cell Adhesion Molecule 1 (VCAM01)," J. Exp. Med., 186:313-323 (1997).
International Search Report and the Written Opinion from Corresponding PCT/US2012/036069 dated Oct. 19, 2012.

(56) References Cited

OTHER PUBLICATIONS

Daugherty, A. L. et al., "Formulation and Delivery Issues for Monoclonal Antibody Therapeutics," Current Trends in Monoclonal Antibody Development and Manufacturing, Biotechnology: Pharmaceutical Aspects, Chapter 8, 103-129 (2010).

Wang, W., et al., "Antibody Structure, Instability, and Formulation," Journal of Pharmaceutical Sciences, vol. 96, 1-26 (2007).

Chen, et al., "Influence of histidine on the stability and physical properties of a fully human antibody in aqueous and solid forms," Pharm. Res., Dec. 2003, pp. 1952-1960, vol. 20, No. 12.

Feagan, et al., "Treatment of active Crohn's disease with MLN0002, a humanized antibody to the alpha4beta7 integrin," Clin. Gastroenterol Hepatol., Dec. 2008, pp. 1370-1377, vol. 6, No. 12.

Kerwin Bae, et al., "Polysorbates 20 and 80 used in the formulation of protein biotherapeutics: structure and degradation pathways," Journal of Pharmaceutical Science, Aug. 2008, pp. 2924-2935, vol. 97, No. 8.

Sigma Aldrich Product Information Sheet Tween 80.

DrugBank Database entry for Vedolizumab.

"Formulation and Process Development Strategies for Manufacturing Biopharmaceuticals", Feroz Jameel and Susan Hershenson (eds), John Wiley and Sons, Inc., Hoboken, USA, 2010; Front matter; p. 383-427; 469-472; 692-694.

Mahler et al. Pharm Sci. Sep. 2009; 98 (9): 2909-2934.

Gokarn et al., 2008, J. Pharm. Sci., 97: 3051-3066.

Notice of Opposition of EP Patent No. 2704742 by Dehmel & Bettenhausen Patentwalte PartmbB.

Arakawa et al., Amino Acids. 2007 Nov; 33 (4): 587-605. Epub Mar 16, 2007.

Sigma Product Information Sheet Tween 20.

Janeway et al., "Immunobiology: The Immune System in Health and Disease", 5th edition. New York: Gartland Science; 2001, p. 95.

Notice of Opposition of EP Patent No. 2704742 by Gill Jennings and Every LLP.

\* cited by examiner

FIG. 1A

New LDP02 Heavy DNA — contains cloning sites (lower case), Kozak sequence (upper case) and Leader (lower case)

gaattctcgagatcgatCTCACCatgggatggagctgtatcatcctcttcttggtagcaacagtgcaacagtgtccactccag
gtgCAATTGGTGCAGTCTGGGGCTGAGGTTAAGAAGCCTGGGGCTTCAGTGAA
GGTGTCCTGCAAGGGTTCTGGCTACACCTTCACCAGTACTGGATGCATTGGG
TGAGGCAGGGCGCCTGGCCAAGCGTCTAGAGTGGATGGGAGAGATTGATCCTTC
TGAGAGTAATACTAACTACAATCAAAAATTCAAGGGACGCGTCACATTGACT
GTAGACACATTTCCGCTAGCACAGCCTACATGGAGCTCTCCAGCCTGAGATCTG
AGGACACTGCGGTCTACTATTGTGCAAGAGGGGTTACGACGGATGGGACTA
TGCTATTGACTACTGGGGTCAAGGCACCCTGGTCACCGTCAGCTCAGCCTCCA
CCAAGGGCCCATCGGTCTTCCCCCTGGCACCCTCCTCCAAGAGCACCTCTGGG
GGCACAGCGGCCCTGGGCTGCCTGGTCAAGGACTACTTCCCCGAACCGGTGA
CGGTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCCCT
CCAGCAGCTTGGGCACCCAGACCTACATCTGCAACGTGAATCACAAGCCCAG
CAACACCAAGGTGACAAGAAAGTTGAGCCCAAATCTTGTGACAAACTCAC
ACATGCCCACCGTGCCCAGCACCTGAACTCGGGGGCACCGTCAGTCTTCC
TCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGG
AGCAGTACAACAGCACGTACCGTGTGGTCAGCGTCCTCACCGTCCTGCACCA
GGACTGGCTGAATGGC AAGGAGTACAAGTGCAAGGTCTCCAACAAAGCCCTCCAGCCCCCATCGAGA
AACCATCTCCAAAGGCCAAAGGGCAGCCCCGAGAACCACAGGTGTACACCCT
GCCCCCATCCCGGGATGAGCTGACCAAGAACCAGGTCAGCCTGACCTGCCTG
GTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTC
CTTCTTCCTCTACAGCAAGCTCACCGTGGACAAGAGCAGGTGGCAGCAGGGG
AACGTCTTCTCATGCTCCGTGATGCATGAGGCTCTGCACAACCACTACACGCA
GAAGAGCCTCTCCCTGTCTCCGGGTAAAtaatctagagca

New LDP02 Heavy Protein (space between VHL, VH and Human IgG1-FcRmut)
MGWSCIILFLVATATGVHS
QVQLVQSGAEVKKPGASVKVSCK<u>GSGYTFTSYWMH</u>WVRQAPGQRLEWIG<u>EIDP
SESNTNYNQKFK</u>GRVTLTVDISASTAYMELSSLRSEDTAVYYCAR<u>GGYDGWDY
AIDY</u>WGQGTLVTVSS
ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCP
PCPAPELAGAPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTI
SKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLS
PGK

New LDP02 Light DNA – contains cloning sites (lower case), Kozak sequence (upper case) and Leader (lower case)

gaattctcgagatcgatCTCACCatggggatggagctgtatcatcctcttcttggtagcaacagctacaggtgtccactccgat
GTAGTGATGACTCAAAGTCCACTCTCCCTGCCTGTCACCCCTGGAGAACCAGC
TTCTATCTCTTGCAGGTCTAGTCAGAGTCTTGCAAAGAGTTATGGGAACACCT
ATTTGTCTCTTGGTACCTGCAGAAGCCTGGCCAGTCTCCACAGCTCCTCATCTAT
GGGATTTCCAACAGATTTTCTGGGGTGCCAGACAGGTTCAGTGGCAGTGGTT
CAGGGACAGATTTCACACTCAAGATCTCGCGAGTAGAGGCTGAGGACGTGGG
AGTGTATTACTGCTTACAAGGTACACATCAGCCGTACACGTTCGGACAGGGG
ACCAAGGTGGAGATCAAGCGTACGGTGGCTGCACCATCTGTCTTCATCTTCCC
GCCATCTGATGAGCAGTTGAAAATCTGGAACTGCCTCTGTTGTGTGCCTGCTGA
ATAACTTCTATCCCAGAGAGGCCAAAGTACAGTGGAAGGTGGATAACGCCCT
CCAATCGGGTAACTCCCAGGAGAGTGTCACAGAGCAGGACAGCAGCAAGGACAG
CACCTACAGCCTCAGCAGCACCCTGACCCTGAGCAAAGCAGACTACGAGAAA
CACAAAGTCTACGCCTGCGAAGTCACCCATCAGGGCCTGAGCTCGCCCGTCA
CAAAGAGCTTCAACAGGGGAGAGTGTagtctagagcagc

New LDP02 Light Protein (space between VKL, VK and Human C Kappa)

MGWSCIILFLVATATGVHS
DVVMTQSPLSLPVTPGEPASISCRSSQSLAKSYGNTYLSWYLQKPGQSPQLLIYGI
SNRFSGVPDRFSGSGSGTDFTLKISRVEAEDVGVYYCLQGTHQPYTFGQGTKVEI
K

RTVAAPSVFIFPPSDEQLKSGTASVVCLLNNFYPREAKVQWKVDNALQSGNSQE
SVTEQDSKDSTYSLSSTLTLSKADYEKHKVYACEVTHQGLSSPVTKSFNRGEC

FIG. 3

PAIRWISE newMLN02-no sig          LDP-02-no sig.txt

```
A   1 DVVMTQSPLSLPVTPGEPASISCRSSQSLAKSYGNTYLSWYLQKPGQSPQ  50
      ||||||||||||||||||||||||||||||||||||||||||||||||||
B   1 DVVMTQSPLSLPVTPGEPASISCRSSQSLAKSYGNTYLSWYLQKPGQSPQ  50

51 LLIYGISNRFSGVPDRFSGSGSGTDFTLKISRVEAEDVGVYYCLQGTHQP 100
      |||||||||||||||||||||||||||||||||||||||||||||||||
   51 LLIYGISNRFSGVPDRFSGSGSGTDFTLKISRVEAEDVGVYYCLQGTHQP 100

101 YTFGQGTKVEIKRTVAAPSVFIFPPSDEQLKSGTASVVCLLNNFYPREAK 150
      ||||||||||||| ||||||||||||||||||||||||||||||||||||
  101 YTFGQGTKVEIKRADAAPSVFIFPPSDEQLKSGTASVVCLLNNFYPREAK 150

151 VQWKVDNALQSGNSQESVTEQDSKDSTYSLSSTLTLSKADYEKHKVYACE 200
      |||||||||||||||||||||||||||||||||||||||||||||||||
  151 VQWKVDNALQSGNSQESVTEQDSKDSTYSLSSTLTLSKADYEKHKVYACE 200

201 VTHQGLSSPVTKSFNRGEC 219
      |||||||||||||||||||
  201 VTHQGLSSPVTKSFNRGEC 219
```

FIG. 4

Pairwise Hum kappa-const    MI:Mur kappa-const.txt

```
A   1 rtvaapsvfifppsdeqlksgtasvvcllnnfypreakvqwkvdnalqsg  50
      ||| .|||  ||||| ||||  ||||| ||  . ||: . |||.| | . 
B   1 radaaptvsifppsseqltsggasvvcflnnfypkdinvkwkidgserqn  50

A  51 nsqesvteqdskdstyslsstltlskadyekhkvyacevthqglsspvtk 100
       |.||  :||||||| |.|| |:||| | ||.| ||| .||. .||:|| 
B  51 gvlnswtdqdskdstysmsstltltkdeyerhnsytceathktstspivk 100

A 101 sfnrgec 107
      |||| ||
B 101 sfnrnec 107
```

FIG. 8
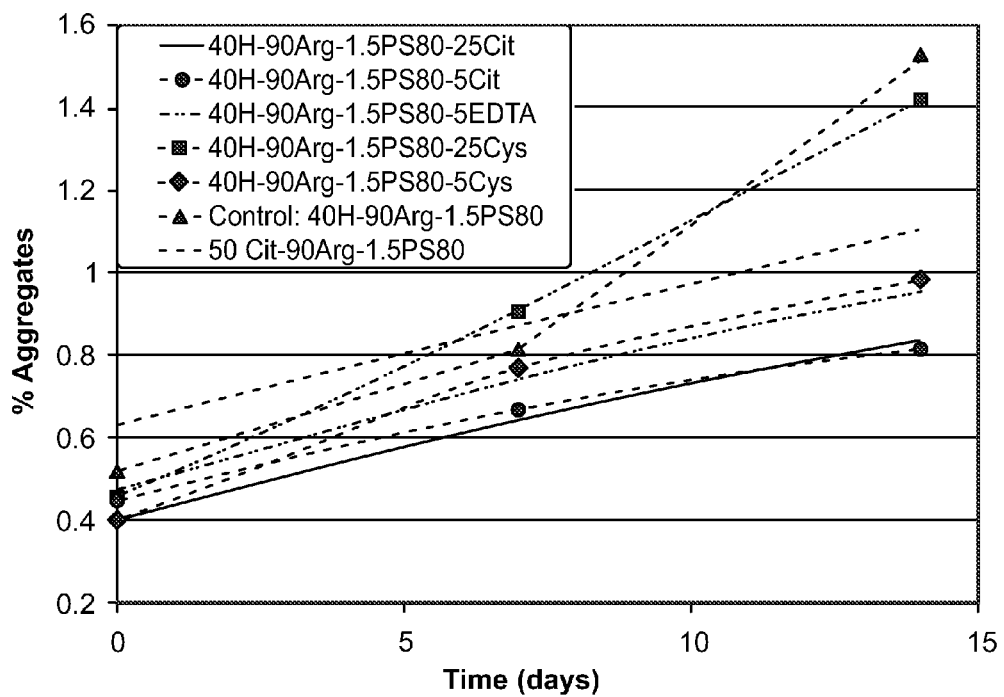
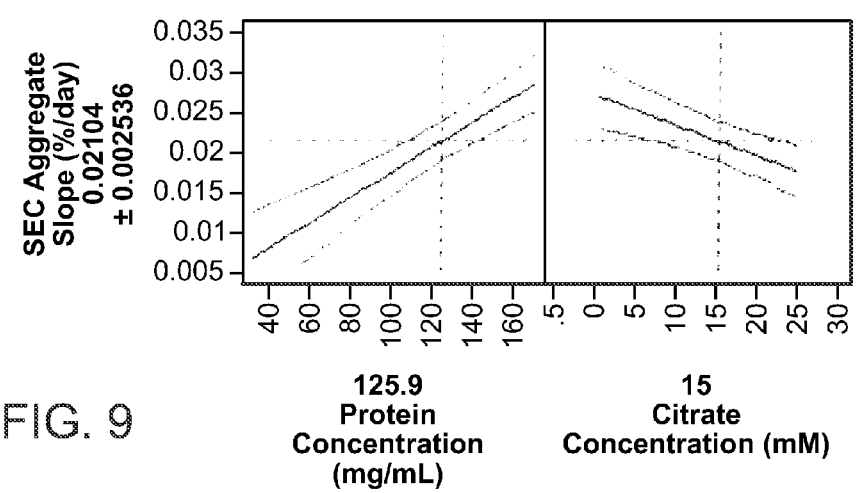
FIG. 9

FIG. 14A

GM607'Cl antibody kappa light chain variable region

SEQ ID NO: 14

```
Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Pro Gln Thr Phe Gly Gln Gly Thr Lys Val Glu Ile Lys
                100                 105                 110
```

21/28'CL antibody heavy chain variable region

SEQ ID NO: 15

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
            20                  25                  30
Ala Met His Trp Val Arg Gln Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Gly Gly Tyr Tyr Gly Ser Gly Ser Asn Tyr Trp Gly Gln Gly
                100                 105                 110
Thr Leu Val Thr Val Ser Ser
        115

FIG. 14B

Components of a Protein Product in a Pre-filled Syringe

SEQUENCE LISTING

<160> NUMBER OF SEQ ID NOS: 15

<210> SEQ ID NO 1
<211> LENGTH: 1445
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1

```
gaattctcga gatcgatctc accatgggat ggagctgtat catcctcttc ttggtagcaa      60
cagctacagg tgtccactcc caggtgcaat tggtgcagtc tggggctgag gttaagaagc     120
ctggggcttc agtgaaggtg tcctgcaagg gttctggcta caccttcacc agctactgga     180
tgcattgggt gaggcaggcg cctggccaac gtctagagtg gatcggagag attgatcctt     240
ctgagagtaa tactaactac aatcaaaaat tcaaggacg cgtcacattg actgtagaca     300
tttccgctag cacagcctac atggagctct ccagcctgag atctgaggac actgcggtct     360
actattgtgc aagagggggt tacgacggat gggactatgc tattgactac tggggtcaag     420
gcaccctggt caccgtcagc tcagcctcca ccaagggccc atcggtcttc cccctggcac     480
```

-continued

```
cctcctccaa gagcacctct gggggcacag cggccctggg ctgcctggtc aaggactact    540
tccccgaacc ggtgacggtg tcgtggaact caggcgccct gaccagcggc gtgcacacct    600
tcccggctgt cctacagtcc tcaggactct actccctcag cagcgtggtg accgtgccct    660
ccagcagctt gggcacccag acctacatct gcaacgtgaa tcacaagccc agcaacacca    720
aggtggacaa gaaagttgag cccaaatctt gtgacaaaac tcacacatgc ccaccgtgcc    780
cagcacctga actcgcgggg gcaccgtcag tcttcctctt ccccccaaaa cccaaggaca    840
ccctcatgat ctcccggacc cctgaggtca catgcgtggt ggtggacgtg agccacgaag    900
accctgaggt caagttcaac tggtacgtgg acggcgtgga ggtgcataat gccaagacaa    960
agccgcggga ggagcagtac aacagcacgt accgtgtggt cagcgtcctc accgtcctgc   1020
accaggactg gctgaatggc aaggagtaca agtgcaaggt ctccaacaaa gccctcccag   1080
cccccatcga gaaaaccatc tccaaagcca agggcagccc cgagaaccag gtgtacaccc   1140
ccctgccccc atcccgggat gagctgacca agaaccaggt cagcctgacc tgcctggtca   1200
aaggcttcta tcccagcgac atcgccgtgg agtgggagag caatgggcag ccggagaaca   1260
actacaagac cacgcctccc gtgctggact ccgacggctc cttcttcctc tacagcaagc   1320
tcaccgtgga caagagcagg tggcagcagg ggaacgtctt ctcatgctcc gtgatgcatg   1380
aggctctgca caaccactac acgcagaaga gcctctccct gtctccgggt aaataatcta   1440
gagca                                                               1445
```

<210> SEQ ID NO 2
<211> LENGTH: 470
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Gly Ser Gly Tyr Thr Phe
            35                  40                  45

Thr Ser Tyr Trp Met His Trp Val Arg Gln Ala Pro Gly Gln Arg Leu
        50                  55                  60

Glu Trp Ile Gly Glu Ile Asp Pro Ser Glu Ser Asn Thr Asn Tyr Asn
65                  70                  75                  80

Gln Lys Phe Lys Gly Arg Val Thr Leu Thr Val Asp Ile Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Gly Tyr Asp Gly Trp Asp Tyr Ala Ile Asp
        115                 120                 125

Tyr Trp Gly Gln Gly Thr Leu Val Thr Val Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Cys Pro Pro Cys Pro Ala Pro Glu
                245                 250                 255

Leu Ala Gly Ala Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 3
<211> LENGTH: 751
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
gaattctcga gatcgatctc accatgggat ggagctgtat catcctcttc ttggtagcaa      60
cagctacagg tgtccactcc gatgtagtga tgactcaaag tccactctcc ctgcctgtca     120
cccctggaga accagcttct atctcttgca ggtctagtca gagtcttgca aagagttatg     180
ggaacaccta tttgtcttgg tacctgcaga agcctggcca gtctccacag ctcctcatct     240
atgggatttc aacagatttc tctggggtgc cagacaggtt cagtggcagt ggttcaggga     300

```
cagatttcac actcaagatc tcgcgagtag aggctgagga cgtgggagtg tattactgct     360
tacaaggtac acatcagccg tacacgttcg gacaggggac caaggtggag atcaagcgta     420
cggtggctgc accatctgtc ttcatcttcc cgccatctga tgagcagttg aaatctggaa     480
ctgcctctgt tgtgtgcctg ctgaataact tctatcccag agaggccaaa gtacagtgga     540
aggtggataa cgccctccaa tcgggtaact cccaggagag tgtcacagag caggacagca     600
aggacagcac ctacagcctc agcagcaccc tgaccctgag caaagcagac tacgagaaac     660
acaaagtcta cgcctgcgaa gtcacccatc agggcctgag ctcgcccgtc acaaagagct     720
tcaacagggg agagtgttag tctagagcag c                                    751
```

<210> SEQ ID NO 4
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Met Gly Trp Ser Cys Ile Ile Leu Phe Leu Val Ala Thr Ala Thr Gly
1               5                   10                  15

Val His Ser Asp Val Val Met Thr Gln Ser Pro Leu Ser Leu Pro Val
            20                  25                  30

Thr Pro Gly Glu Pro Ala Ser Ile Ser Cys Arg Ser Ser Gln Ser Leu
        35                  40                  45

Ala Lys Ser Tyr Gly Asn Thr Tyr Leu Ser Trp Tyr Leu Gln Lys Pro
    50                  55                  60

Gly Gln Ser Pro Gln Leu Leu Ile Tyr Gly Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Leu Gln Gly Thr His Gln Pro Tyr Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 5
<211> LENGTH: 219
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 5
```

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
            20                  25                  30

Tyr Gly Asn Thr Tyr Leu Ser Trp Tyr Leu Gln Lys Pro Gly Gln Ser
        35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

Arg Ala Asp Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 6
<211> LENGTH: 107
<212> TYPE: PRT
<213> ORGANISM: Homo sapiens

<400> SEQUENCE: 6
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 7
<211> LENGTH: 107
<212> TYPE: PRT
<213> ORGANISM: Mus sp.

<400> SEQUENCE: 7

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 8
<211> LENGTH: 5
<212> TYPE: PRT
<213> ORGANISM: Mus sp.

<400> SEQUENCE: 8

Ser Tyr Trp Met His
1               5

<210> SEQ ID NO 9
<211> LENGTH: 17
<212> TYPE: PRT
<213> ORGANISM: Mus sp.

<400> SEQUENCE: 9

Glu Ile Asp Pro Ser Glu Ser Asn Thr Asn Tyr Asn Gln Lys Phe Lys
1               5                   10                  15

Gly

<210> SEQ ID NO 10
<211> LENGTH: 12
<212> TYPE: PRT
<213> ORGANISM: Mus sp.

<400> SEQUENCE: 10

Gly Gly Tyr Asp Gly Trp Asp Tyr Ala Ile Asp Tyr
1               5                   10

<210> SEQ ID NO 11
<211> LENGTH: 16
<212> TYPE: PRT
<213> ORGANISM: Mus sp.

<400> SEQUENCE: 11

Arg Ser Ser Gln Ser Leu Ala Lys Ser Tyr Gly Asn Thr Tyr Leu Ser
1               5                   10                  15

<210> SEQ ID NO 12
<211> LENGTH: 7
<212> TYPE: PRT
<213> ORGANISM: Mus sp.
```

<400> SEQUENCE: 12

Gly Ile Ser Asn Arg Phe Ser
1               5

<210> SEQ ID NO 13
<211> LENGTH: 9
<212> TYPE: PRT
<213> ORGANISM: Mus sp.

<400> SEQUENCE: 13

Leu Gln Gly Thr His Gln Pro Tyr Thr
1               5

<210> SEQ ID NO 14
<211> LENGTH: 111
<212> TYPE: PRT
<213> ORGANISM: Homo sapiens

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Lys Val Glu Ile Lys
            100                 105                 110

<210> SEQ ID NO 15
<211> LENGTH: 119
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
        115

FORMULATION FOR ANTI-α4β7 ANTIBODY

RELATED APPLICATIONS

This application is the U.S. National Stage of International Application No. PCT/US2012/036069, filed May 2, 2012, published in English, and claims priority to U.S. Provisional Application 61/544,054, filed on Oct. 6, 2011 and U.S. Provisional Application 61/481,522 filed on May 2, 2011. The entire contents of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 30, 2012, is named 92596603.txt and is 16,986 bytes in size.

BACKGROUND OF THE INVENTION

Advances in biotechnology have made it possible to produce a variety of proteins for pharmaceutical applications using recombinant DNA techniques. Because proteins are larger and more complex than traditional organic and inorganic drugs (i.e., possessing multiple functional groups in addition to complex three-dimensional structures), the formulation of such proteins poses special problems. For a protein to remain biologically active, a formulation must preserve the conformational integrity of at least a core sequence of the protein's amino acids, while at the same time protecting the protein's multiple functional groups from degradation. Proteins may suffer from a lack of stability, and monoclonal and polyclonal antibodies in particular may be relatively unstable (See e.g., Wang, et al., *J. Pharm Sci.* 96:1-26 (2007)). A large number of formulation options are available, and not one approach or system is suitable for all proteins. Several factors to be considered have been reported (See e.g., Wang et al.).

Numerous characteristics may affect a protein's stability. In fact, even in the case of purified antibodies, the antibody structures may be heterogenous, which further complicates the formulation of such systems. Moreover, the excipients included in antibody formulations preferably minimize any potential immune response.

In the case of antibodies, preservation of the conformational integrity is even more important. Degradation pathways for proteins can involve chemical instability (i.e., any process which involves modification of the protein by bond formation or cleavage resulting in a new chemical entity) or physical instability (i.e., changes in the higher order structure of the protein). Chemical instability is manifested in, for example, deamidation, isomerization, hydrolysis, oxidation, fragmentation, glycan beta elimination or disulfide exchange. Physical instability can result from denaturation, aggregation, precipitation or adsorption, for example. The four most common protein degradation pathways are protein fragmentation, aggregation, deamidation, and oxidation. Consequences of chemical or physical instability of therapeutic protein include a lowering of the effective administered dose, decreased safety of the therapy due to, for example irritation or immunological reactivity, and more frequent manufacturing due to short shelf life.

Several publications have disclosed generally various methods of treating inflammatory bowel diseases, and provided dosing schemes for administration of agents designed to treat inflammatory bowel disease. For example, WO 96/24673 discloses mucosal vascular addressins and treatment of diseases associated with leukocyte recruitment to the gastrointestinal tract as a result of leukocyte binding to cells expressing MAdCAM. U.S. 2005/0095238 describes methods of treating a disease associated with leukocyte infiltration of mucosal tissue and administration to a human an effective amount of a human or humanized immunoglobulin or antigen binding fragment having binding specificity for α4β7 integrin. U.S. 2005/0095238 further describes various doses (e.g. 0.15, about 0.5, about 1.0, about 1.5 or about 2.0 mg immunoglobulin or fragment per kg body weight) and various intervals between doses (7, 14, 21, 28, or 30 days). However, the aforementioned patents and publications do not disclose specific formulations of the anti-α4β7 antibody or the specific doses and dose regimens described and claimed herein. Importantly, the aforementioned patents do not disclose formulations, doses, and dose regimens that provide for the methods of treatment (supported by clinical trial data) described and claimed herein.

The antibody formulations of the present invention may be useful for inhibiting leukocyte binding to cells expressing MAdCAM and therefore aid in treatment of inflammatory bowel diseases in patients. There is, accordingly, an urgent need to discover suitable dosages and dosing schedules of these compounds, and to develop formulations, preferably subcutaneous formulations, which give rise to steady, therapeutically effective blood levels of the antibody formulations over an extended period of time in a stable and convenient form.

SUMMARY OF THE INVENTION

The invention relates to the identification of an antioxidant or chelator, and at least one amino acid, as useful excipients for formulating anti-α4β7 antibody formulations whose instability makes them susceptible to deamidation, oxidation, isomerization and/or aggregation. The formulation improves stability, reduces aggregate formation and retards degradation of the antibody therein.

Thus, in a first aspect, the invention relates to a stable liquid pharmaceutical formulation comprising a mixture of an anti-α4β7 antibody, an antioxidant or chelator and at least one free amino acid.

In some embodiments, the stable liquid pharmaceutical formulation has less than about 1.0% aggregate formation after 12 months at room temperature. The stable liquid pharmaceutical formulation can have less than about 0.2% aggregate formation after 12 months at room temperature.

In some embodiments, the antioxidant or chelator is citrate. In some embodiments the chelator is EDTA.

In some embodiments, the free amino acid of the formulation is histidine, alanine, arginine, glycine, glutamic acid, or any combination thereof. The formulation can comprise between about 50 mM to about 175 mM of free amino acid. The formulation can comprise between about 100 mM and about 175 mM of free amino acid. The ratio of free amino acid to antibody molar ratio can be at least 250:1.

The formulation can also contain a surfactant. The surfactant can be polysorbate 20, polysorbate 80, a poloxamer, or any combination thereof.

In some embodiments, the molar ratio of the antioxidant to the surfactant is about 3:1 to about 156:1.

The formulation can have a pH between about 6.3 and about 7.0. The pH of the formulation can be between about 6.5 and about 6.8. The formulation can have a pH between about 6.1 and about 7.0, or between about 6.2 and 6.8.

In some embodiments, the stable liquid pharmaceutical formulation contains at least about 60 mg/ml to about 160 mg/ml anti-α4β7 antibody. The formulation can contain at least about 160 mg/ml anti-α4β7 antibody. The formulation can contain about 150 to about 180 mg/ml antibody or about 165 mg/ml antibody.

In another aspect, the invention relates to a stable liquid pharmaceutical formulation comprising at least about 60 mg/ml to about 160 mg/ml anti-α4β7 antibody, a buffering agent and at least about 10 mM citrate. The buffering agent can be a histidine buffer.

In another aspect, the invention relates to a stable liquid pharmaceutical formulation comprising at least about 60 mg/ml to about 180 mg/ml anti-α4β7 antibody, a buffering agent and at least about 5 mM citrate. The buffering agent can be a histidine buffer.

In another aspect, the invention relates to a stable liquid pharmaceutical formulation comprising at least about 160 mg/ml anti-α4β7 antibody and at least about 10 mM citrate. The formulation can further contain polysorbate 80.

In another aspect, the invention relates to a stable liquid pharmaceutical formulation comprising about 160 mg/ml anti-α4β7 antibody and at least about 5 mM citrate. The formulation can further contain polysorbate 80.

In another aspect, the invention relates to a stable liquid pharmaceutical formulation comprising a mixture of anti-α4β7 antibody, citrate, histidine, arginine and polysorbate 80. The formulation can be present in a container, such as a vial, cartridge, syringe or autoinjector.

The anti-α4β7 antibody in the stable liquid pharmaceutical formulation of the invention can be vedolizumab. The formulation of the invention can be for subcutaneous, intravenous, or intramuscular administration.

In some aspects, the formulation can minimize immunogenicity of the anti-α4β7 antibody.

In another aspect, the invention relates to a method of treating inflammatory bowel disease, comprising administering to a patient in need thereof the stable liquid pharmaceutical formulation described herein. The administering can be subcutaneous administering. The administering can be self-administering.

In yet another aspect, the invention relates to an article of manufacture, comprising a container, a stable liquid pharmaceutical formulation described herein, and instructions for its use.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human α4β7 integrin, wherein the humanized immunoglobulin or antigen-binding fragment thereof is administered to the patient according to the following dosing regimen: (a) initial doses, e.g., in an induction phase treatment regimen, of 165 mg of the humanized immunoglobulin or antigen-binding fragment thereof as a subcutaneous injection every other day for six doses; (b) followed at week six by a seventh and subsequent doses, e.g., in a maintenance phase treatment regimen, of 165 mg of the humanized immunoglobulin or antigen-binding fragment thereof as a subcutaneous injection every two weeks or every four weeks as needed; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain *variable* region and three complementarity determining regions (CDR1. CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen comprising an induction phase of intravenous doses and a maintenance phase of subcutaneous doses: (a) an initial intravenous dose of 300 mg of the humanized immunoglobulin or antigen-binding fragment thereof as an intravenous infusion; (b) followed by a second intravenous subsequent dose of 300 mg of the humanized immunoglobulin or antigen-binding fragment thereof as an intravenous infusion at about two weeks after the initial dose; (c) followed beginning at week six by a third and subsequent doses of 165 mg of the humanized immunoglobulin or antigen-binding fragment thereof as a subcutaneous injection every week, every two weeks, every three weeks or every four weeks as needed; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a mean steady state trough serum concentration of the immunoglobulin or antigen-binding fragment thereof of about 9 to about 13 µg/mL; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a mean steady state trough serum concentrations of the humanized immunoglobulin or antigen-binding fragment thereof of about 35 to about 40 µg/mL; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In another aspect, the invention relates to a method of treating a human patient suffering from inflammatory bowel disease, wherein the method comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen: (a) a plurality of induction phase doses of the humanized immunoglobulin or antigen-binding fragment thereof sufficient to achieve a mean trough serum concentration of about 20 to about 30 µg/mL of the humanized immunoglobulin or antigen-binding fragment thereof by about six weeks of initial dosing; (b) followed by a plurality of maintenance phase doses of the humanized immunoglobulin or antigen-binding fragment thereof as needed to maintain a mean steady state trough serum concentration of about 9 to about 13 µg/mL or about 35 to 40 µg/mL of the immunoglobulin or antigen-binding fragment thereof; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In some aspects, the formulation, method of treatment, dose and/or dose regimen ensure minimal likelihood that a patient will develop antibodies reactive to the anti-α4β7 antibody.

The patient may have had a lack of an adequate response with, loss of response to, or was intolerant to treatment with at least one of an immunomodulator, a tumor necrosis factor-alpha (TNF-α) antagonist or combinations thereof.

The inflammatory bowel disease can be Crohn's disease or ulcerative colitis. The inflammatory bowel disease can be moderate to severely active ulcerative colitis.

The dosing regimen can result in mucosal healing in patients suffering from moderate to severely active ulcerative colitis.

The patient may have previously received treatment with at least one corticosteroid for the inflammatory bowel disease. The patient may concurrently receive treatment with at least one corticosteroid for the inflammatory bowel disease. The dosing regimen can result in a reduction, elimination or reduction and elimination of corticosteroid use by the patient.

In some aspects, the humanized immunoglobulin or antigen-binding fragment thereof is administered in a final dosage form at a concentration of between about 1.0 mg/ml to about 1.4 mg/ml. The humanized immunoglobulin or antigen-binding fragment thereof can be administered in a final dosage form of about 1.2 mg/ml.

In some aspects, the humanized immunoglobulin or antigen-binding fragment is administered in a final dosage form having an amount of anti-α4β7 antibody between about 70 to about 250 mg, between about 90 to about 200 mg, between about 150 to about 180 mg, or at least 160 mg.

In some aspects, the dosing regimen does not alter the ratio of CD4 to CD8 in cerebrospinal fluid of patients receiving said treatment.

The patient can be a person 65 years of age or older and does not require any adjustment of the dosing regimen.

In some aspects the method of treatment with the anti-α4β7 antibody formulation, the dose, or the dose regimen can minimize immunogenicity of the anti-α4β7 antibody.

BRIEF DESCRIPTION OF THE DRAWINGS

FIG. 1 is an illustration of a nucleotide sequence (SEQ ID NO:1) encoding the heavy chain of a humanized anti-α4β7 immunoglobulin, and the deduced amino acid sequence of the heavy chain (SEQ ID NO:2). The nucleotide sequence contains cloning sites (lower case), Kozak sequence (upper case, nucleotides 18-23 of SEQ ID NO:1) and leader sequence (lower case, nucleotides 24-86 of SEQ ID NO:1) at the 5' end of the heavy chain. The open reading frame of the nucleotide sequence is nucleotides 24-1433 of SEQ ID NO:1.

FIG. 2 is an illustration of a nucleotide sequence (SEQ ID NO:3) encoding the light chain of a humanized immunoglobulin referred to herein as vedolizumab, and the deduced amino acid sequence (SEQ ID NO: 4) of the light chain. The nucleotide sequence contains cloning sites (lower case), Kozak sequence (upper case, nucleotides 18-23 of SEQ ID NO:3) and leader sequence (lower case, nucleotides 24-80 of SEQ ID NO:3) at the 5' end of the heavy chain. The open reading frame of the nucleotide sequence is nucleotides 24-737 of SEQ ID NO:3.

FIG. 3 is an alignment of the amino acid sequences of (A) the mature humanized light chain (amino acids 20-238 of SEQ ID NO:4) of the humanized immunoglobulin referred to herein as vedolizumab and (B) the mature humanized light chain of the humanized immunoglobulin referred to herein as LDP-02 (SEQ ID NO:5). (Regarding LDP-02, see, WO 98/06248 and Feagan et al., *N. Eng. J. Med.* 352:2499-2507 (2005)). Feagan et al. describe a clinical study of LDP-02, but in the article they refer to LDP-02 as MLN02.) The alignment illustrates that the amino acid sequences of the light chains of vedolizumab and LDP-02 differ at positions 114 and 115 of the mature light chains.

FIG. 4 is an alignment of amino acid sequences of (A) a generic human kappa light chain constant region (SEQ ID NO:6) and (B) a generic murine kappa light chain constant region (SEQ ID NO:7). The amino acid residues Thr and Val (which are present at positions 114 and 115 of the mature vedolizumab light chain (amino acids 133 and 134 of SEQ ID NO:4)) are present in the constant region of the human kappa light chain, whereas the amino acid residues Ala and Asp (which are present at positions 114 and 115 of the mature LDP-02 light chain (SEQ ID NO:5)) are present in the constant region of the mouse kappa light chain.

FIG. 8 is a graph showing the effect of excipients on the formation of aggregates. 25 mM citrate, 5 mM citrate, 5 mM EDTA, 25 mM cysteine, or 5 mM cysteine was added to formulations. All three excipients reduced the formation of aggregates.

FIG. 9 is a set of graphs that shows reduction in aggregate formation with the presence of 25 mM citrate in the formulation, and a correlation between increased protein concentration and increased rate of aggregate formation.

FIG. 14 shows the amino acid sequences of (A) the mature human GM607'CL antibody kappa light chain variable region and (B) the the human 21/28'CL heavy chain variable region.

FIG. 17 (B) shows the initial glide force for each syringe manufacturer and needle size.

DETAILED DESCRIPTION OF THE INVENTION

Figure 5:
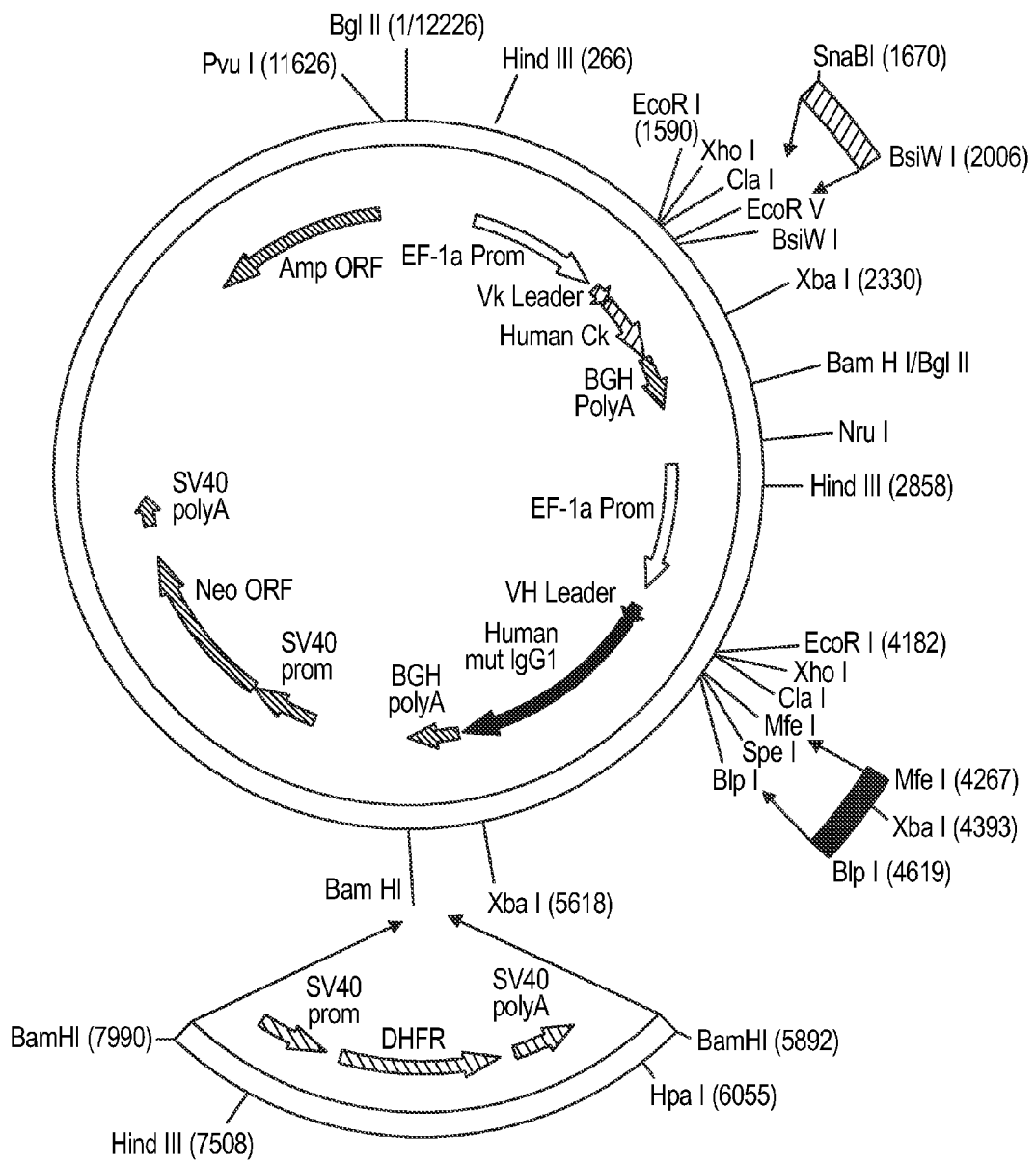
FIG. 5 is a map of vector pLKTOK38D (also referred to as pTOK38MLN02-TV), which encodes the humanized heavy chain and the humanized light chain of MLN02, and is suitable for producing vedolizumab in CHO cells. (See, U.S. Patent Application Publication No. 2004/0033561 A1 which discloses pLKTOK38. pLKTOK38D is a variant of pLKTOK38 in which the restriction sites indicated on the map flank the sequence encoding the light chain variable region.)

The invention relates to a pharmaceutical formulation comprising anti-α4β7 antibodies. The pharmaceutical formulation may be a mixture comprising an antioxidant or chelator (e.g., citrate), anti-α4β7 antibody and a free amino acid. The pharmaceutical formulation may be in a solid or liquid form.

Definitions

The term "pharmaceutical formulation" refers to a preparation that contains an anti-α4β7 antibody in such form as to permit the biological activity of the antibody to be effective, and which contains no additional components which are unacceptably toxic to a subject to which the formulation would be administered.

A "stable" formulation is one in which the antibody therein substantially retains its physical stability and/or its chemical stability and/or its biological activity upon storage. In one aspect, the formulation substantially retains its physical and chemical stability, as well as its biological activity upon storage. The storage period is generally selected based on the intended shelf-life of the formulation. Various analytical techniques for measuring protein stability are available in the art and are reviewed, for example, in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For example, the liquid formulation is stable at about 40° C. for at least about 3 days, 5 days, 1 week, 2 weeks, 3 weeks, 4 weeks, 5 weeks or 6 weeks. In another aspect, the lyophilized formulation is stable at about 40° C. for at least about 2-4 weeks, at least about 3 months, at least about 6 months, at least about 9 months, at least about 12 months, or at least about 18 months. The liquid and/or lyophilized formulation in another aspect is stable at about 5° C. and/or 25° C. for at least about 1 month, at least about 3 months, at least about 6 months, at least about 9 months, at least about 12 months, at least about 18 months, at least about 24 months, at least about 30 months, or at least about 36 months; and/or stable at about −20° C. and/or −70° C. for at least about 1 month, at least about 3 months, at least about 6 months, at least about 9 months, at least about 12 months, at least about 18 months, at least about 24 months, at least about 30 months, at least about 36 months, at least about 42 months, or at least about 48 months. Furthermore, the liquid formulation may, in some embodiments, be stable following freezing (to, e.g., −80° C.) and thawing, for example following 1, 2 or 3 cycles of freezing and thawing.

The stability of a liquid formulation can be evaluated qualitatively and/or quantitatively in a variety of different ways, including evaluation of dimer, multimer and/or aggregate formation (for example using size exclusion chromatography (SEC), matrix-assisted laser desorption-ionization time-of-flight mass spectrometry (MALDI-TOF MS), analytical ultracentrifugation, light scattering (photon correlation spectroscopy, dynamic light scattering (DLS), static light scattering, multi-angle laser light scattering (MALLS)), flow-based microscopic imaging, electronic impedance (coulter) counting, light obscuration or other liquid particle counting system, by measuring turbidity, and/or by visual inspection); by assessing charge heterogeneity using cation exchange chromatography (CEX), isoelectric focusing (IEF), e.g. capillary technique (cIEF), or capillary zone electrophoresis; amino-terminal or carboxy-terminal sequence analysis; mass spectrometric analysis; SDS-PAGE or SEC analysis to compare fragmented, intact and multimeric (i.e., dimeric, trimeric, etc.) antibody; peptide map (for example tryptic or LYS-C) analysis; evaluating biological activity or antigen binding function of the antibody; and the like. Stability of a solid-state formulation can also be evaluated qualitatively and/or quantitatively in a variety of different ways, including direct tests, such as identifying crystal structure by X-Ray Powder Diffraction (XRPD); evaluating antibody structure in the solid state using Fourier Transform Infrared Spectroscopy (FTIR); and measuring thermal transitions in the lyophilized solid (melting, glass transition, etc.) using Differential Scanning calorimetry (DSC) and indirect tests such as measuring moisture content by Karl Fisher test, e.g., to extrapolate the likelihood of chemical instability through hydrolysis. Instability may involve any one or more of: aggregation (e.g., non-covalent soluble aggregation, covalent soluble aggregation (e.g., disulfide bond rearrangement/scrambling), insoluble aggregation), deamidation (e.g. Asn deamidation), oxidation (e.g. Met oxidation), isomerization (e.g. Asp isomeriation), clipping/hydrolysis/fragmentation (e.g. hinge region fragmentation), succinimide formation, N-terminal extension, C-terminal processing, glycosylation differences, and the like.

A "deamidated" monoclonal antibody is one in which one or more asparagine or glutamine residue thereof has been derivatized, e.g. to an aspartic acid or an iso-aspartic acid.

An antibody which is "susceptible to deamidation" is one comprising one or more residue which has been found to be prone to deamidate.

An antibody which is "susceptible to oxidation" is an antibody comprising one or more residue which has been found to be prone to oxidation.

An antibody which is "susceptible to aggregation" is one which has been found to aggregate with other antibody molecule(s), especially upon freezing, heating, drying, reconstituting and/or agitation.

An antibody which is "susceptible to fragmentation" is one which has been found to be cleaved into two or more fragments, for example at a hinge region thereof.

By "reducing deamidation, oxidation, aggregation, or fragmentation" is intended to mean preventing or decreasing (e.g., to 80%, 60%, 50%, 40%, 30%, 20% or 10% of) the amount of deamidation, aggregation, or fragmentation relative to the monoclonal antibody formulated at a different pH or in a different buffer.

An "aggregate", "SEC aggregate", or "soluble aggregate" is more than one and less than or equal to ten antibody proteins and/or fragments associated together through covalent, ionic, or hydrophobic interactions to form a larger protein body.

An "insoluble aggregate" or "particle" is greater than ten antibody proteins and/or fragments associated together through covalent, ionic, or hydrophobic interactions to form a larger protein body.

As used herein, "biological activity" of a monoclonal antibody refers to the ability of the antibody to bind to antigen and result in a measurable biological response which can be measured in vitro or in vivo. Such activity may be antagonistic or agonistic.

The cell surface molecule, "$\alpha 4\beta 7$ integrin," or "$\alpha 4\beta 7$," is a heterodimer of an $\alpha_4$ chain (CD49D, ITGA4) and a $\beta_7$ chain (ITGB7). Each chain can form a heterodimer with an alternative integrin chain, to form for example $\alpha_4\beta_1$ or $\alpha_E\beta_7$. Human $\alpha_4$ and $\beta_7$ genes (GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, $\alpha 4\beta 7$ can exist in either a resting or activated state. Ligands for $\alpha 4\beta 7$ include vascular cell adhesion molecule (VCAM), fibronectin and mucosal addressin (MAdCAM, e.g., MAdCAM-1).

As used herein, a human immunoglobulin or antigen-binding fragment thereof that has "binding specificity for the $\alpha 4\beta 7$ complex" binds to $\alpha 4\beta 7$, but not to $\alpha 4\beta 1$ or $\alpha E\beta 7$.

As used herein, an "isotonic" formulation has substantially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffering agent" refers to a buffer that resists changes in pH by the action of its acid-base conjugate components. The buffering agent may be present in a liquid or solid formulation of the invention. In some embodiments, the buffering agent of this invention adjusts the pH of the formulation to about 5.0 to about 7.5, to about pH 5.5 to about 7.5, to about pH 6.0 to about 7.0, or to a pH of about 6.3 to about 6.5. In one aspect, examples of buffering agents that alone or in combination, will control the pH in the 5.0 to 7.5 range include acetate, succinate, gluconate, histidine, citrate, phosphate, maleate, cacodylate, 2-[N-morpholino] ethanesulfonic acid (MES), bis(2-hydroxyethyl)iminotris [hydroxymethyl]methane (Bis-Tris), N-[2-acetamido]-2-iminodiacetic acid (ADA), glycylglycine and other organic acid buffers. In another aspect, the buffering agent herein is histidine or citrate.

A "histidine buffer" is a buffer comprising histidine ions. Examples of histidine buffers include histidine chloride, histidine acetate, histidine phosphate, histidine sulfate solutions. The histidine buffer or histidine-HCl buffer has a pH between about pH 5.5 to about 7.0, between about pH 6.1 to about 6.9, or about pH 6.5.

A "citrate buffer" is a buffer comprising citrate ions. Examples of citrate buffers include sodium citrate, ammonium citrate, calcium citrate, and potassium citrate solutions. The citrate buffer has a pH of about 3.0 to 6.2, about pH 5.5 to 6.5, about pH 6.1 to about 6.5, about pH 6.1, about pH 6.2, or about pH 6.5.

A "saccharide" herein is a compound that has a general formula $(CH_2O)_n$ and derivatives thereof, including monosaccharides, disaccharides, trisaccharides, polysaccharides, sugar alcohols, reducing sugars, nonreducing sugars, and the like. Examples of saccharides herein include glucose, sucrose, trehalose, lactose, fructose, maltose, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, and the like. A saccharide can be a lyoprotectant. In one aspect, a saccharide herein is a nonreducing disaccharide, such as sucrose.

Herein, a "surfactant" refers to an agent that lowers surface tension of a liquid. In one aspect, the surfactant is a nonionic surfactant. Examples of surfactants herein include polysorbate (polyoxyethylene sorbitan monolaurate, for example, polysorbate 20 and polysorbate 80); TRITON (t-Octylphenoxypolyethoxyethanol, nonionic detergent, Union Carbide subsidiary of Dow Chemical Co., Midland Mich.); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; sorbitan monopalmitate; and the MONAQUAT series (Mona Industries, Inc., Paterson, N.J.); polyethyl glycol (PEG), polypropylene glycol (PPG), and copolymers of poloxyethylene and poloxypropylene glycol (e.g. Pluronics/Poloxamer, PF68 etc); etc. In another aspect, the surfactant herein is polysorbate 80.

The term "chelator" refers to an agent that binds to an atom through more than one bond. In one aspect, examples of chelators herein include citrate, ethylenediaminetetraacetic acid, ethyleneglycoltetraacetic acid (EGTA), dimercaprol, diethylenetriaminepentaacetic acid, and N,N-bis(carboxymethyl)glycine. In another aspect, the chelator is citrate or EDTA.

The term "antioxidant" refers to an agent that inhibits the oxidation of other molecules. Examples of antioxidants herein include citrate, lipoic acid, uric acid, glutathione, tocopherol, carotene, lycopene, cysteine, phosphonate compounds, e.g., etidronic acid, desferoxamine and malate.

The term "antibody" herein is used in the broadest sense and specifically covers full length monoclonal antibodies, immunoglobulins, polyclonal antibodies, multispecific antibodies (e.g. bispecific antibodies) formed from at least two full length antibodies, e.g., each to a different antigen or epitope, and individual antigen binding fragments, including dAbs, scFv, Fab, F(ab)'$_2$, Fab', including human, humanized and antibodies from non-human species and recombinant antigen binding forms such as monobodies and diabodies.

Molar amounts and ratios of anti-α4β7 antibody to other excipients described herein are calculated on the assumption of an approximate molecular weight of about 150,000 daltons for the antibody. The actual antibody molecular weight may differ from 150,000 daltons, depending on amino acid composition or post-translational modification, e.g., as dependent on the cell line used to express the antibody. Actual antibody molecular weight can be +/−5% of 150,000 daltons.

The term "human antibody" includes an antibody that possesses a sequence that is derived from a human germ-line immunoglobulin sequence, such as an antibody derived from transgenic mice having human immunoglobulin genes (e.g., XENOMOUSE genetically engineered mice (Abgenix, Fremont, Calif.), HUMAB-MOUSE®, KIRIN TC MOUSE™ transchromosome mice, KMMOUSE® (MEDAREX, Princeton, N.J.)), human phage display libraries, human myeloma cells, or human B cells.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mot. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen binding sequences derived from a non-human primate (e.g. Old World Monkey, Ape etc) and human constant region sequences.

"Antigen binding fragments" of the humanized immunoglobulin prepared in the formulation of the invention comprise at least the variable regions of the heavy and/or light chains of an anti-α4β7 antibody. For example, an antigen binding fragment of vedolizumab comprises amino acid residues 20-131 of the humanized light chain sequence of SEQ ID NO:4. Examples of such antigen binding fragments include Fab fragments, Fab' fragments, scFv and F(ab')$_2$ fragments of a humanized immunoglobulin known in the art. Antigen binding fragments of the humanized immunoglobulin of the invention can be produced by enzymatic cleavage or by recombinant techniques. For instance, papain or pepsin cleavage can be used to generate Fab or F(ab')$_2$ fragments, respectively. Antibodies can also be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_1$ domain and hinge region of the heavy chain. In one aspect, antigen binding fragments inhibit binding of α4β7 integrin to one or more of its ligands (e.g. the mucosal addressin MAdCAM (e.g., MAdCAM-1), fibronectin).

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the $V_H$ and $V_L$ domains of antibody, wherein these domains are present in a single polypeptide chain. In one aspect, the Fv polypeptide further comprises a polypeptide linker between the $V_H$ and $V_L$ domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., *Proc. Natl. Acad. Sci. USA*, 90:6444-6448 (1993).

A "full length antibody" is one which comprises an antigen binding variable region as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. In one aspect, the full length antibody has one or more effector functions.

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

A "therapeutic monoclonal antibody" is an antibody used for therapy of a human subject. Therapeutic monoclonal antibodies disclosed herein include anti-α4β7 antibodies.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead of a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), and the like.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

The "light chains" of antibodies from any vertebrate species can be assigned to one of two clearly distinct types, called kappa (κ) and lambda (λ), based on the amino acid sequences of their constant domains.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The terms "Fc receptor" or "FcR" are used to describe a receptor that binds to the Fc region of an antibody. In one aspect, the FcR is a native sequence human FcR. In another aspect, the FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See, review in M. Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:33-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "hypervariable region" when used herein refers to the amino acid residues of an antibody which are responsible for antigen binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., Nature 332:323-329 (1988); and Presta, *Curr. Op. Struct. Biol.* 2:593-596 (1992).

An "affinity matured" antibody is one with one or more alterations in one or more hypervariable regions thereof which result an improvement in the affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7): 3310-9 (1995); and Hawkins et al., *J. Mol. Biol.* 226:889-896 (1992).

An "isolated" antibody is one which has been identified and separated and/or recovered from a component of its natural environment. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease. The terms "patient" and "subject" are used interchangeably herein.

The antibody which is formulated is substantially pure and desirably substantially homogeneous (i.e. free from contaminating proteins etc). "Substantially pure" antibody means a composition comprising at least about 90% antibody by weight, based on total weight of the protein, alternatively, at least about 95% or 97% by weight. "Substantially homogeneous" antibody means a composition comprising protein wherein at least about 99% by weight of protein is specific antibody, e.g., anti-α4β7 antibody, based on total weight of the protein.

"Clinical remission" as used herein with reference to ulcerative colitis subjects refers to a complete Mayo score of 2 or less points and no individual subscore greater than 1 point. Crohn's disease "clinical remission" refers to a CDAI score of 150 points or less.

A "clinical response" as used herein with reference to ulcerative colitis subjects refers to a reduction in complete Mayo score of 3 or greater points and 30% from baseline, (or a partial Mayo score of 2 or greater points and 25% or greater from baseline, if the complete Mayo score was not performed at the visit) with an accompanying decrease in rectal bleeding subscore of 1 or greater points or absolute rectal bleeding score of 1 or less point. A "clinical response" as used herein with reference to Crohn's disease subjects refers to a 70 point or greater decrease in CDAI score from baseline (week 0).

"Mucosal healing" as used herein with reference to ulcerative colitis subjects refers to an endoscopic subscore of 1 point or less.

As used herein, "treatment failure" refers to disease worsening, a need for rescue medications or surgical intervention for treatment of ulcerative colitis or Crohn's disease. A rescue medication is any new medication or any increase in dose of a baseline medication required to treat new or unresolved ulcerative colitis or Crohn's disease symptoms (other than antidiarrheals for control of chronic diarrhea).

Formulations

As described herein, it has been discovered that anti-α4β7 antibodies are more stable when formulated with an antioxidant or chelator. In addition, as described herein, anti-α4β7 antibodies may be formulated to reduce aggregate formation (e.g., the amount of polysorbate 80 in the formulation may be reduced). For example, formulations that comprise citrate or EDTA and anti-α4β7 antibodies decrease the rate of antibody aggregate formation during storage. Formulations may also be stored without oxygen to reduce aggregate formation. In one embodiment, the formulation has an antibody aggregate formation of less than about 2.5% at 25° C. after 12 months. In one embodiment, the formulation has an antibody aggregate formation of less than about 2.0% at 25° C. after 12 months. In one embodiment, the formulation has an antibody aggregate formation of less than about 1.6% at 25° C. after 12 months. In one embodiment, the formulation has an antibody aggregate formation of less than about 1.3% at 25° C. after 12 months. In one embodiment, the formulation has an antibody aggregate formation of less than about 1.0% at 25° C. after 12 months. In another embodiment, the formulation has an antibody aggregate formulation of less than about 0.5% at 5° C. after 12 months. In another embodiment, the formulation has an antibody aggregate formulation of less than about 0.3% at 5° C. after 12 months.

The present invention provides, in a first aspect, a stable anti-α4β7 antibody formulation. The formulation comprises an anti-α4β7 antibody and an antioxidant or chelator. The formulation also comprises a buffering agent that may be one or more free amino acids. The formulation may optionally further comprise a surfactant. The antibody in the formulation may be a full length antibody or an antigen binding fragment thereof, such as a Fab, Fv, scFv, Fab' or F(ab')$_2$ fragment.

Aggregate formation can be reduced by removing oxygen from the formulation. Alternatively, the formulation can contain an antioxidant or chelator. In one aspect, exemplary antioxidants and chelators that can be included in the formulation include lipoic acid, uric acid, glutathione, tocopherol, carotene, lycopene, cysteine, ethylenediaminetetraacetic acid (EDTA), ethyleneglycoltetraacetic acid (EGTA), dimercaprol, diethylenetriaminepentaacetic acid, and N,N-bis(carboxymethyl)glycine, phosphonate compounds, e.g., etidronic acid, desferoxamine, malate and citrate. Some antioxidants and chelators can decrease the rate of aggregate formation during storage of the formulation. In another aspect, the chelator and/or antioxidant is citrate or EDTA. Exemplary chelator concentrations for liquid formulations are in the range of from about greater than 0 mM to about 60 mM, about 5 mM to about 50 mM, about 5 mM to about 15 mM, about 10 mM to about 25 mM, and about 20 to about 30 mM. In another aspect, the chelator concentration is from about 0 mM to about 30 mM. In one embodiment, the chelator and/or antioxidant is citrate, and the citrate concentration is from about 0 mM to about 15 mM, about 0 mM to about 10 mM, or about 0 mM to about 5 mM.

The formulation can contain any desired one free amino acid, which can be in the L-form, the D-form or any desired mixture of these forms. In one aspect, free amino acids that can be included in the formulation include, for example, histidine, alanine, arginine, glycine, glutamic acid, serine, lysine, tryptophan, valine, cysteine and combinations thereof. Some amino acids can stabilize the proteins against degradation during manufacturing, drying, lyophilization and/or storage, e.g., through hydrogen bonds, salt bridges, antioxidant properties, or hydrophobic interactions or by exclusion from the protein surface. Amino acids can act as tonicity modifiers or can act to decrease viscosity of the formulation. In another aspect, free amino acids, such as histidine and arginine, can act as lyoprotectants, and do not crystallize when lyophilized as components of the formulation. Free amino acids, such as glutamic acid and histidine, alone or in combination, can act as buffering agents in aqueous solution in the pH range of 5 to 7.5. In still yet another aspect, the formulation contains histidine, arginine, or a combination of histidine and arginine. In still yet another aspect, free amino acid concentrations for liquid formulations are in the range from about 9 mM to about 0.5 M, for example, from about 10 mM to about 90 mM, about 10 mM to about 75 mM, about 10 mM to about 40 mM, about 25 mM to about 50 mM, about 15 mM to about 300 mM, about 20 mM to about 200 mM, about 25 mM to about 150 mM, about 50 mM to about 75 mM, about 50 mM to about 120 mM, about 50 to about 150 mM, or about 50 mM or about 125 mM.

The formulation can optionally further contain at least one surfactant, e.g., to control soluble and insoluble aggregate formation. In one aspect, the surfactant is a non-ionic surfactant. In another aspect, the surfactant is an ionic surfactant. Exemplary surfactants that can be included in the formulation include, for example, polysorbate 20, polysorbate 80, a poloxamer (Pluronic®) and combinations thereof. When present, the surfactant is generally included in an amount which reduces formation of insoluble aggregates of antibody, e.g., during bottling, freezing, drying, lyophilization and/or reconstitution, in the presence of silicone, filling vials, prefilled syringes, and/or cartridges. The surfactant concentration is generally from about 0.0001% to about 1.0%, from about 0.01% to about 0.5%, for example, about 0.05%, 0.1%, 0.15%, 0.20%, 0.3%, 0.4%, or 0.5% (w/v). Higher concentrations of surfactant, e.g., polysorbate 80 can lead to more SEC aggregate formation. Reducing the concentration of polysorbate 80 can reduce SEC aggregate formation upon storage. In one aspect, the surfactant:antibody molar ratio is from about 0.7:1 to about 2.0:1. In another aspect, the surfactant:antibody molar ratio is 1.5:1.

An embodiment of an anti-α4β7 antibody formulation contains a high concentration of anti-α4β7 antibody. For example, in one embodiment, the liquid formulations can comprise at least about 60 mg/ml, at least about 70 mg/ml, at least about 80 mg/ml, at least about 90 mg/ml, at least about 100 mg/ml, at least about 110 mg/ml, at least about 120 mg/ml, at least about 130 mg/ml, at least about 140 mg/ml, at least about 150 mg/ml, at least about 160 mg/ml, at least about 170 mg/ml, at least about 180 mg/ml, at least about 190 mg/ml, at least about 200 mg/ml, at least about 250 mg/ml, at least about 300 mg/ml, from about 60 mg/ml to about 190 mg/ml, from about 60 mg/ml to about 170 mg/ml anti-α4β7 antibody, from about 150 mg/ml to about 180 mg/ml, or about 160 mg/ml or about 165 mg/ml anti-α4β7 antibody. Alternatively, in another aspect, the liquid formulations can comprise at least about 154 mg/ml, at least about 176 mg/ml.

The formulation can be a liquid or a solid. Liquid formulations are aqueous solutions or suspensions, prepared in a suitable aqueous solvent, such as water or an aqueous/organic mixture, such as water alcohol mixtures. Liquid formulations have a pH between about 5.5 and about 7.5, between about 6.0 and 7.3, between about 6.0 and about 7.0, between about 6.0 and 6.5, between about 6.0 and 6.3, between about 6.3 and 7.1, or between about 6.4 and 7.0, or between about 6.3 and 6.8, such as about 6.0, 6.1, 6.2, 6.3, 6.4, 6.5, 6.6, 6.7, 6.8, or 6.9. Liquid formulations can be kept at room temperature, refrigerated (e.g., 2-8° C.), or frozen (e.g., −20° C. or −70° C.) for storage.

A solid formulation can be prepared in any suitable way and can be in the form of a cake or powder, for example, with the addition of a lyoprotectant. In one aspect, the solid formulation is prepared by drying a liquid formulation as described herein, for example by lyophilization or spray drying. When the formulation is a solid formulation, the formulation can have a moisture content of no more than about 5%, no more than about 4.5%, no more than about 4%, no more than about 3.5%, no more than about 3%, no more than about 2.5%, no more than about 2%, no more than about 1.5%, no more than about 1%, or is substantially anhydrous. A solid formulation can be dissolved, i.e. reconstituted, in a suitable medium or solvent to become liquid suitable for administration. Suitable solvents for reconstituting the solid formulation include water, isotonic saline, buffer, e.g., phosphate-buffered saline, Ringer's (lactated or dextrose) solution, minimal essential medium, alcohol/aqueous solutions, dextrose solution, etc. The amount of solvent can result in a therapeutic protein concentration higher, the same, or lower then the concentration prior to drying. In another aspect, the reconstituted anti-α4β7 antibody concentration is the same concentration as in the pre-drying liquid formulation.

The formulation may be sterile, and this can be achieved according to the procedures known to the skilled person for generating sterile pharmaceutical formulations suitable for administration to human subjects, prior to, or following, preparation of the formulation. The formulation can be sterilized as a liquid, e.g., before drying and/or after reconstitution by filtration through small pores, through aseptic processing or by exposure to ultraviolet radiation. Filter pore sizes can be 0.1 μm or 0.2 μm to filter microorganisms or 10 to 20 nm to filter virus particles. Alternatively, or additionally, the dried formulation can be sterilized, e.g., by exposure to gamma radiation. In one aspect, the anti-α4β7 antibody liquid formulation is sterilized by filtration before drying.

In one aspect, the formulation is stable upon storage. Various stability assays are available to the skilled practitioner for confirming the stability of the formulation. For example, the antibody in the liquid formulation may be stable upon storage at about 25° C. for at least about 4 weeks, at least about 2 months, at least about 3 months, or at least about 6 months, or at least about 9 months, or at least about 12 months; at about 2-8° C. at least about 3 months, at least about 1 year, at least about 2 years, at least about 3 years or longer. Alternatively or in addition, the antibody in the formulation may be stable upon storage at about 15° C. for at least about 4 weeks, at least about 3 months, at least about 6 months, at least about 9 months, at least about 1 year, or longer. Alternatively or in addition, the antibody in the formulation may be stable upon storage at about −20° C. or −70° C. for at least about 4 weeks; at least about 3 months, at least about 6 months, at least about 9 months, at least about 1 year, at least about 2 years, at least about 3 years, at least about 4 years or longer.

Stability can be tested by evaluating physical stability, chemical stability, and/or biological activity of the antibody in the formulation around the time of formulation as well as following storage at the noted temperatures. Physical and/or chemical stability of a liquid formulation or a reconstituted dry powder can be evaluated qualitatively and/or quantitatively in a variety of different ways (see, e.g., *Analytical Techniques for Biopharmaceutical Development*, Rodriguez-Diaz et al. eds. Informa Healthcare (2005)), including evaluation of soluble and insoluble aggregate formation (for example using size exclusion chromatography, analytical ultracentrifugation, MALDI-TOF MS, light scattering (dynamic (DLS) or MALLS), flow-based microscopic imaging, or other liquid particle counting system, by measuring turbidity, by density gradient centrifugation and/or by visual inspection); by assessing charge heterogeneity using cation exchange chromatography (see also Vlasak and Ionescu, *Curr. Pharm. Biotechnol.* 9:468-481 (2008) and Harris et al. *J. Chromatogr. B Biomed. Sci. Appl.* 752:233-245 (2001)), isoelectric focusing or capillary zone electrophoresis; amino-terminal or carboxy terminal sequence analysis; mass spectrometric analysis; SDS-PAGE analysis to compare fragmented, intact and multimeric (i.e., dimeric, trimeric, etc.) antibody; peptide map (for example tryptic or LYS- and the like). Instability may result in aggregation, deamidation (e.g., Asn deamidation), oxidation (e.g., Met oxidation), isomerization (e.g., Asp isomerization), denaturation, clipping/hydrolysis/fragmentation (e.g., hinge region fragmentation), succinimide formation, unpaired cysteine(s), N-terminal extension, C-terminal processing, glycosylation differences, etc. Biological activity or antigen binding function, e.g., binding of the anti-α4β7 antibody to MAdCAM (e.g., MAdCAM-1) or inhibition of the binding of a cell expressing α4β7 integrin to MAdCAM (e.g., MAdCAM-1), e.g., immobilized MAdCAM (e.g., MAdCAM-1), can be evaluated using various techniques available to the skilled practitioner (see e.g., Soler et al., *J. Pharmacol. Exper. Ther.* 330:864-875 (2009)). Measurement of the moisture content of a dry formulation can indicate how likely a formulation will undergo chemical or physical degradation, with higher moisture leading to more degradation.

A stable formulation can contribute to a low immunogenicity of an anti-α4β7 antibody. An immunogenic anti-α4β7 antibody can lead to a human-anti-human antibody (HAHA) response in human subjects or patients. Patients who develop a HAHA response to an anti-α4β7 antibody can have adverse events (e.g., site infusion reaction) upon treatment or can eliminate anti-α4β7 antibody quickly, resulting in a lower dose than planned by treatment. A report (Feagen et al. (2005) N. Engl. J. Med. 352:2499-2507) of early study of an anti-α4β7 antibody treatment indicated that human antihuman antibodies developed by week 8 in 44% of treated patients. The antibody in this study was stored as a liquid and did not contain any polysorbate.

In some embodiments, the formulation can increase the proportion of HAHA negative patients to at least 40%, at least 50%, at least 60%, at least 70%, at least 80% or at least 90% of patients compared to the HAHA results of a less stable formulation.

In some embodiments, an anti-α4β7 antibody formulation has ≥50% major charged isoform, ≥55% major charged isoform, or 65 to 70% major charged isoform. In other aspects, a stable anti-α4β7 antibody formulation has ≤45% acidic charged isoforms, ≤40% acidic charged isoforms, ≤30% acidic charged isoforms or 22 to 28% acidic isoforms. In still other aspects, a stable anti-α4β7 antibody formulation has ≤25% basic isoforms, ≤20% basic isoforms, ≤15% basic isoforms, about 5% basic isoforms or about 10% basic isoforms. In one aspect, a stable anti-α4β7 antibody formulation has ≥55% major isoform, ≤30% acidic isoforms and/or ≤20% basic isoforms, e.g., as determined by CEX. In another aspect, a stable anti-α4β7 antibody formulation has ≥50% major isoform, ≤45% acidic isoforms and/or <10% basic isoforms, e.g., as determined by cIEF.

In some aspects, an anti-α4β7 antibody dry, solid formulation has ≤10% moisture content, ≤5% moisture content or <2.5% moisture content. The time required for reconstitution is ≤60 minutes, ≤50 minutes or ≤40 minutes or ≤30 minutes or ≤20 minutes.

Monomeric content and/or aggregate content (e.g., as dimers, trimers, tetramers, pentamers, oligomers and higher-order aggregates), i.e., in the liquid formulation, or in the reconstituted formulation, can be measured by SEC, analytical ultracentrifugation, light scattering (DLS or MALLS), MALDI-TOF MS or nanoscale measurement, such as nanoparticle tracking analysis NTA, NanoSight Ltd, Wiltshire, UK). Resolution, characterization and quantification of aggregate can be achieved in a number of ways, including increasing the length of the SEC column separation, e.g., by a longer column or by serial attachment of a second or more SEC column(s) in line with the initial analytical SEC column, supplementing SEC quantification of monomers with light scattering, or by using NTA.

In one embodiment, an anti-α4β7 antibody formulation has ≥90% monomeric antibody, ≥95% monomeric antibody, or 97 to 99% monomeric antibody. In another embodiment, the majority of the material in an anti-α4β7 antibody formulation has an average radius of ≤20 nm, ≤15 nm, ≤10 nm, or about 5 to about 7 nm. In one aspect, an anti-α4β7 antibody formulation has 80% amount heavy plus light chain by protein analysis. In one aspect, there is 90% heavy plus light chain. In another aspect, an anti-α4β7 antibody formulation has ≤10% aggregate, ≤5% aggregate, ≤2.5% aggregate, ≤1.5% aggregate, ≤1.0% aggregate or ≤0.5% aggregate. In another aspect, stable anti-α4β7 antibody formulation has ≥96% monomer and/or ≤2.5% aggregate. In yet another aspect, a stable anti-α4β7 antibody formulation has about 99% monomer and/or about <1% aggregate.

Particle sizes, greater than 1 to 2 micron, e.g., of aggregates or undissolved excipient, i.e., in the liquid formulation, or in the reconstituted formulation can be measured by light obscuration (e.g., liquid particle counting system (HIAC) by Hach Ultra Analytics (Grants Pass, Oreg.)), microscopy, coulter counter, or digital (e.g., flow-based) microscopic imaging based system such as microfluidics imaging (MFI) by Brightwell (Ottawa, Calif.) or FLOWCAM® Image particle analyzer by Fluid Imaging Technologies (Yarmouth, Me.). In one aspect, particle size in an anti-α4β7 antibody preparation is about 30 μm, about 25 μm, about 10 μm, about 5 μm, about 2 μm or 1 μm or less. The amount of particles should be minimized in antibody formulations. In one aspect, an amount of particles in an anti-α4β7 antibody formulation is <6000 particles ≥10 μm diameter and/or <600 particles ≥25 μm diameter in one dose (U.S. Pharmacopoeia Chp. 788, light obscuration counting method; half those amounts by microscopic quantification method). In another aspect, an amount of particles in a dose of an anti-α4β7 antibody formulation is about 1000 particles ≥10 μm and about 0-100 particles ≥25 μm (MFI method). In yet another aspect, an amount of particles per milliliter, e.g., by MFI measurement, in a dose of an anti-α4β7 antibody formulation is about 500 to about 2000 of 2-10 μm particles per ml, about 50 to about 350 of ≥10 μm particles per ml and about 0 to about 50 of ≥25 μm particles per ml. In yet another aspect, an amount of particles in a dose of an anti-α4β7 antibody formulation is about 500 to about 100,000, about 1000 to about 5000 or about 1500 to about 3000 of 2-10 μm particles per ml.

The viscosity of an anti-α4β7 antibody formulation can be controlled for subcutaneous or intramuscular administration. The viscosity can be affected by protein concentration and pH. For example, as the protein concentration increases, the viscosity can increase. An increase in pH can decrease the viscosity of the anti-α4β7 antibody formulation. In some protein formulations, sodium chloride is added to reduce the viscosity of the formulation. Additional components that can affect viscosity of an anti-α4β7 antibody formulation are amino acids such as histidine and arginine.

An anti-α4β7 antibody formulation can be isotonic (e.g., 250-350 mOsm) or hypertonic (e.g., greater than 350 mOsm, greater than 450 mOsm, greater than 550 mOsm or greater than 650 mOsm), e.g., for subcutaneous or intramuscular administration. In one aspect, the anti-α4β7 antibody formulation is not hypotonic, e.g., less than 250 mOsm. In another aspect, the anti-α4β7 antibody formulation is about 350 to about 400 mOsm, about 400 to about 450 mOsm or about 350 to about 450 mOsm.

Instability leading to denaturation can be assessed by differential scanning calorimetry (DSC). Antibodies have two melting temperatures (Tm) in DSC, e.g., Tm1 and Tm2. Certain excipients can affect the stability of the native anti-α4β7 antibody. A finding of a higher melting temperature when comparing formulations by DSC can indicate a more stable anti-α4β7 antibody formulation with the higher Tm. For example, at pH5.7, the Tm of an anti-α4β7 antibody formulation is lower, and thus less stable than at pH 6.5. In one aspect, Tm1 of an anti-α4β7 antibody formulation is >60° C. In another aspect, the Tm1 of an anti-α4β7 antibody formulation is about 65° C. to about 70° C. or about 69° C. In one aspect, Tm2 of an anti-α4β7 antibody formulation is >80° C. In another aspect, the Tm2 of an anti-α4β7 antibody formulation is about 82° C. to about 88° C. or about 86° C.

In one embodiment, an anti-α4β7 antibody formulation has a binding affinity or EC50 value of about 60% to about 140% of the reference standard anti-α4β7 antibody. In one aspect, an anti-α4β7 antibody in a formulation described herein binds to α4β7, e.g., on a cell (WO98/06248 or U.S. Pat. No. 7,147,851), at a value of about 80% to about 120% of the reference standard. In another embodiment, an anti-α4β7 antibody formulation has the ability to inhibit at least 50%, or at least 60% of the binding of a cell expressing α4β7 integrin to MAdCAM (e.g., MAdCAM-1), e.g., a MAdCAM-Ig chimera (see U.S. Patent Application Publication No. 20070122404, also for reference standard examples).

As noted above, freezing of the formulation is specifically contemplated herein. Hence, the formulation can be tested for stability upon freezing and thawing. Accordingly, the antibody in a liquid formulation may be stable upon freezing and thawing the formulation, for example the antibody can be stable after one, two, three, four, five or more freeze/thaw cycles.

In some embodiments, the pharmaceutical formulation is a liquid formulation comprising at least about 60 mg/ml to about 170 mg/ml anti-α4β7 antibody, a buffering agent (e.g., histidine), and at least about 5 mM citrate. In other embodiments, the formulation is a liquid formulation comprising at least about 60 mg/ml to about 170 mg/ml anti-α4β7 antibody, a buffering agent (e.g., citrate), amino acid (e.g., arginine) and surfactant (e.g., polysorbate 80).

In another embodiment, the formulation comprises at least about 140 mg/ml or about 150 mg/ml to about 170 mg/ml, for example, about 160 mg/ml of an anti-α4β7 antibody, a buffering agent (e.g., histidine), at least about 5 mM citrate and a free amino acid (e.g., arginine).

In yet another embodiment, the formulation comprises at least about 160 mg/ml of an anti-α4β7 antibody, a buffering agent (e.g., histidine), at least about 5 mM citrate, 0.2% polysorbate 80, and a free amino acid (e.g., arginine). In an embodiment, the buffer concentration in the formulation is about 15 to about 75 mM, about 25 to about 65 mM, or about 50 mM. The free amino acid concentration in the formulation is about 50 to about 250 mM, about 75 to about 200 mM, about 100 to about 150 mM or about 125 mM; the polysorbate 80 concentration in the formulation is about 0.05% to 0.4%, about 0.1% to 0.4%, about 0.1% to 0.3%, about 0.1% to 0.25%, about 0.1% to 0.2%, or about 0.2%.

In some embodiments, the formulation is a solid formulation (e.g., a lyophilized formulation), comprising a mixture of an anti-α4β7 antibody, citrate, histidine, arginine, polysorbate 80, and a lyoprotectant or a saccharide, such as a non-reducing sugar. Saccharide can be included in the liquid formulation to reach concentrations from 0% to 20%, or about 6% to about 10%.

In one embodiment, the formulation is lyophilized and stored as a single dose in one container, e.g., vial, syringe, cartridge, and/or autoinjector. The container can be stored at about 2-8° C. or 25° C. until it is administered to a subject in need thereof. The vial may for example be a 5, 10 or 20 cc vial (for example for a 160 mg/ml dose). The vial may contain at least about 20 mg, at least about 50 mg, at least about 70 mg, at least about 80 mg, at least about 100 mg, at least about 120 mg, at least about 155 mg, at least about 180 mg, at least about 200 mg, at least about 240 mg, at least about 300 mg, at least about 360 mg, at least about 400 mg, at least about 540 mg, or at least about 900 mg of anti-α4β7 antibody. In one aspect, the container contains about 165 mg of anti-α4β7 antibody.

In another embodiment, the formulation is liquid and stored as a single dose in one or two vials, cartridges, syringes, or autoinjectors. The vial, cartridge, syringe, or autoinjector can be stored at about 2-8° C. until its contents, e.g., an anti-α4β7 antibody, are administered to a subject in need thereof. The vial may, for example, be a 5, 10 or 20 cc vial (for example for a 160 mg/ml dose). The vial may contain at least about 20 mg, at least about 50 mg, at least about 70 mg, at least about 80 mg, at least about 100 mg, at least about 120 mg, at least about 155 mg, at least about 180 mg, at least about 200 mg, at least about 240 mg, at least about 300 mg, at least about 360 mg, at least about 400 mg, at least about 540 mg, or at least about 900 mg of anti-α4β7 antibody. In one aspect, the vial contains about 165 mg of anti-α4β7 antibody. The syringe or cartridge may be a 1 mL or 2 mL container (for example for a 160 mg/mL dose) or more than 2 ml, e.g., for a higher dose (at least 320 mg or 400 mg or higher). The syringe or cartridge may contain at least about 20 mg, at least about 50 mg, at least about 70 mg, at least about 80 mg, at least about 100 mg, at least about 120 mg, at least about 155 mg, at least about 180 mg, at least about 200 mg, at least about 240 mg, at least about 300 mg, at least about 360 mg, at least about 400 mg, or at least about 500 mg of anti-α4β7 antibody.

One or more other pharmaceutically acceptable carriers, excipients or stabilizers such as those described in *Remington: The Science and Practice of Pharmacy,* 21st Edition, Hendrickson, R. Ed. (2005) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including citrate and cysteine; chelating agents such as EDTA; metal complexes (e.g., Zn-protein complexes); biodegradable polymers such as polyesters; preservatives; container wall lubricants, e.g., silicone, mineral oil, glycerin, or TRIBO-GLIDE® (Tribo Film Research, Inc.) perfluoropolyether derivative, for injection ease and/or salt-forming counterions such as sodium.

α4β7 Antibodies

Anti-α4β7 antibodies suitable for use in the formulations include antibodies from any desired source, such as fully human antibodies, murine antibodies, rabbit antibodies and the like, and any desired engineered antibodies, such as chimeric antibodies, humanized antibodies, and the like. Antigen-binding fragments of any of these types of antibodies, such as Fab, Fv, scFv, Fab' and F(ab')$_2$ fragments, are also suitable for use in the formulations.

The anti-α4β7 antibody can bind to an epitope on the α4 chain (e.g., humanized MAb 21.6 (Bendig et al., U.S. Pat. No. 5,840,299)), on the β7 chain (e.g., FIB504 or a humanized derivative (e.g., Fong et al., U.S. Pat. No. 7,528,236)), or to a combinatorial epitope formed by the association of the α4 chain with the β7 chain. In one aspect, the antibody binds a combinatorial epitope on the α4β7 complex, but does not bind an epitope on the α4 chain or the β7 chain unless the chains are in association with each other. The association of α4 integrin with β7 integrin can create a combinatorial epitope for example, by bringing into proximity residues present on both chains which together comprise the epitope or by conformationally exposing on one chain, e.g., the α4 integrin chain or the β7 integrin chain, an epitopic binding site that is inaccessible to antibody binding in the absence of the proper integrin partner or in the absence of integrin activation. In another aspect, the anti-α4β7 antibody binds both the α4 integrin chain and the β7 integrin chain, and thus, is specific for the α4β7 integrin complex. Such antibodies can bind α4β7 but not bind α4β1, and/or not bind $α_E$β7, for example. In another aspect, the anti-α4β7 antibody binds to the same or substantially the same epitope as the Act-1 antibody (Lazarovits, A. I. et al., *J. Immunol.,* 133(4): 1857-1862 (1984), Schweighoffer et al., *J. Immunol.,* 151(2): 717-729, 1993; Bednarczyk et al., *J. Biol. Chem.,* 269(11): 8348-8354, 1994). Murine ACT-1 Hybridoma cell line, which produces the murine Act-1 monoclonal antibody, was deposited under the provisions of the Budapest Treaty on Aug. 22, 2001, on behalf of Millennium Pharmaceuticals, Inc., 40 Landsdowne Street, Cambridge, Mass. 02139, U.S.A., at the American Type Culture Collection, 10801 University Boulevard, Manassas, Va. 20110-2209, U.S.A., under Accession No. PTA-3663. In another aspect, the anti-α4β7 antibody is a human antibody or an α4β7 binding protein using the CDRs provided in U.S. Patent Application Publication No. 2010/0254975.

In one aspect, the anti-α4β7 antibody inhibits binding of α4β7 to one or more of its ligands (e.g. the mucosal addressin, e.g., MAdCAM (e.g., MAdCAM-1), fibronectin, and/or vascular addressin (VCAM)). Primate MAdCAMs (e.g., MAdCAM-1) are described in the PCT publication WO 96/24673, the entire teachings of which are incorporated herein by this reference. In another aspect, the anti-α4β7 antibody inhibits binding of α4β7 to MAdCAM (e.g., MAdCAM-1) and/or fibronectin without inhibiting the binding of VCAM.

In one aspect, the anti-α4β7 antibodies for use in the formulations are humanized versions of the mouse Act-1 antibody. Suitable methods for preparing humanized antibodies are well-known in the art. Generally, the humanized anti-α4β7 antibody will contain a heavy chain that contains the 3 heavy chain complementarity determining regions (CDRs, CDR1, SEQ ID NO:8, CDR2, SEQ ID NO:9 and CDR3, SEQ ID NO:10) of the mouse Act-1 antibody and suitable human heavy chain framework regions; and also contain a light chain that contains the 3 light chain CDRs (CDR1, SEQ ID NO:11, CDR2, SEQ ID NO:12 and CDR3, SEQ ID NO:13) of the mouse Act-1 antibody and suitable human light chain framework regions. The humanized Act-1 antibody can contain any suitable human framework regions, including consensus framework regions, with or without amino acid substitutions. For example, one or more of the framework amino acids can be replaced with another amino acid, such as the amino acid at the corresponding position in the mouse Act-1 antibody. The human constant region or portion thereof, if present, can be derived from the κ or λ light chains, and/or the γ (e.g., γ1, γ2, γ3, γ4), μ, α (e.g., α1, α2), δ or ε heavy chains of human antibodies, including allelic variants. A particular constant region (e.g., IgG1), variant or portions thereof can be selected in order to tailor effector function. For example, a mutated constant region (variant) can be incorporated into a fusion protein to minimize binding to Fc receptors and/or ability to fix complement (see e.g., Winter et al., GB 2,209,757 B; Morrison et al., WO 89/07142; Morgan et al., WO 94/29351, Dec. 22, 1994). Humanized versions of Act-1 antibody were described in PCT publications nos. WO98/06248 and WO07/61679, the entire teachings of each of which are incorporated herein by this reference.

In another aspect, the anti-α4β7 humanized antibodies for use in the formulation comprise a heavy chain variable region comprising amino acids 20 to 140 of SEQ ID NO:2, and a light chain variable region comprising amino acids 20 to 131 of SEQ ID NO:4 or amino acids 21 to 132 of SEQ ID NO:5. If desired, a suitable human constant region(s) can be present. For example, the humanized anti-α4β7 antibody can comprise a heavy chain that comprises amino acids 20 to 470 of SEQ ID NO:2 and a light chain comprising amino acids 21 to 239 of SEQ ID NO:5. In another example, the humanized anti-α4β7 antibody can comprise a heavy chain that comprises amino acids 20 to 470 of SEQ ID NO:2 and a light chain comprising amino acids 20 to 238 of SEQ ID NO:4. FIG. 4 shows an alignment which compares the generic light chains of human antibodies with murine antibodies. The alignment illustrates that the humanized light chain of vedolizumab (e.g., Chemical Abstract Service (CAS, American Chemical Society) Registry number 943609-66-3), with two mouse residues switched for human residues, is more human than the light chain of LDP-02 (FIG. 3). In addition, LDP-02 has the somewhat hydrophobic, flexible alanine 114 and a hydrophilic site (Aspartate 115) that is replaced in vedolizumab with the slightly hydrophilic hydroxyl-containing threonine 114 and hydrophobic, potentially inward facing valine 115 residue.

Further substitutions to the antibody sequence can be, for example, mutations to the heavy and light chain framework regions, such as a mutation of isoleucine to valine on residue 2 of SEQ ID NO:14; a mutation of methionine to valine on residue 4 of SEQ ID NO:14; a mutation of alanine to glycine on residue 24 of SEQ ID NO:15; a mutation of arginine to lysine at residue 38 of SEQ ID NO:15; a mutation of alanine to arginine at residue 40 of SEQ ID NO:15; a mutation of methionine to isoleucine on residue 48 of SEQ ID NO:15; a mutation of isoleucine to leucine on residue 69 of SEQ ID NO:15; a mutation of arginine to valine on residue 71 of SEQ ID NO:15; a mutation of threonine to isoleucine on residue 73 of SEQ ID NO:15; or any combination thereof; and replacement of the heavy chain CDRs with the CDRs (CDR1, SEQ ID NO:8, CDR2, SEQ ID NO:9 and CDR3, SEQ ID NO:10) of the mouse Act-1 antibody; and replacement of the light chain CDRs with the light chain CDRs (CDR1, SEQ ID NO:11, CDR2, SEQ ID NO:12 and CDR3, SEQ ID NO:13) of the mouse Act-1 antibody.

In some embodiments, the anti-α4β7 humanized antibodies for use in the formulation comprise a heavy chain variable region that has about 95%, 96%, 97%, 98%, or 99% sequence identity to amino acids 20 to 140 of SEQ ID NO:2, and a light chain variable region that has about 95%, 96%, 97%, 98%, or 99% sequence identity to amino acids 20 to 131 of SEQ ID NO:4 or amino acids 21 to 132 of SEQ ID NO:5. Amino acid sequence identity can be determined using a suitable sequence alignment algorithm, such as the Lasergene system (DNASTAR, Inc., Madison, Wis.), using the default parameters. In an embodiment, the anti-α4β7 antibody for use in the formulation is vedolizumab (CAS, American Chemical Society, Registry number 943609-66-3).

Other α4β7 antibodies may also be used in the formulations and dosing regimes described herein. For example, the α4β7 antibodies described in US 2010/0254975 (Amgen, Inc.), incorporated by reference herein in its entirety, are suitable for use in the formulations and methods of treating inflammatory bowel disease in an individual.

The anti-α4β7 antibody can be produced by expression of nucleic acid sequences encoding each chain in living cells, e.g., cells in culture. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an anti-α4β7 antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus, is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Rather et al., EMBO J. 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to Chinese hamster ovary (CHO), NS0, HeLa, VERY, baby hamster kidney (BHK), monkey kidney (COS), MDCK, 293, 3T3, WI38, human hepatocellular carcinoma cells (e.g., Hep G2), breast cancer cell lines such as, for example, BT483, Hs578T, HTB2, BT20 and T47D, and normal mammary gland cell line such as, for example, CRL7030 and Hs578Bst.

The glycosylation machinery of different cell types can produce antibodies with different glycosylation composition than in another cell type, or no glycosylation, as with bacterial cells. In one aspect, cell types for production of the anti-α4β7 antibody are mammalian cells, such as NS0 or CHO cells. In one aspect, the mammalian cells can comprise the deletion of an enzyme involved in cell metabolism and the exogenous gene of interest can be operably linked to a replacement enzyme, e.g., in a construct or vector for introduction into the cells, e.g., by transformation or transfection. The construct or vector with the exogenous gene confers to the cells which host the construct or vector a selection advantage to encourage production of the polypeptide encoded by the exogenous gene. In one embodiment, CHO cells are DG44 cells (Chasin and Urlaub (1980) *PNAS USA* 77:4216), comprising the deletion or inactivation of the dihydrofolate reductase gene. In another embodiment, CHO cells are CHO K1 cells comprising the deletion or inactivation of the glutamine synthase gene (see, e.g., U.S. Pat. No. 5,122,464 or 5,827,739).

Solid Formulations

Solid formulations of the invention are generally prepared by drying a liquid formulation. Any suitable method of drying can be used, such as lyophilization or spray drying. In one aspect, a lyoprotectant is added to the formulation prior to lyophilization. Lyophilization involves freezing a liquid formulation, usually in the container that will be used to store, ship and distribute the formulation (e.g., a vial, syringe (e.g., a single- or dual-chamber syringe), or cartridge (e.g., a single- or dual-chamber cartridge) (See, e.g., Gatlin and Nail in *Protein Purification Process Engineering*, ed. Roger G. Harrison, Marcel Dekker Inc., 317-367 (1994).) Once the formulation is frozen, the atmospheric pressure is reduced and the temperature is adjusted to allow removal of the frozen solvent e.g., through sublimation. This step of the lyophilization process is sometimes referred to as primary drying. If desired, the temperature can then be raised to remove any solvent that is still bound to the dry formulation by evaporation. This step of the lyophilization process is sometimes referred to as secondary drying. When the formulation has reached the desired degree of dryness, the drying process is concluded and the containers are sealed. The final solid formulation is sometimes referred to as a "lyophilized formulation" or a "cake." The lyophilization process can be performed using any suitable equipment. Suitable lyophilization equipment is available from a number of commercial sources (e.g., SP Scientific, Stone Ridge, N.Y.).

A variety of suitable apparatuses can be used to dry liquid formulations to produce a solid (e.g., lyophilized) formulation. Generally, lyophilized formulations are prepared by those of skill in the art using a sealed chamber that contains shelves, on which vials of the liquid formulation to be dried are placed. The temperature of the shelves, as well as cooling and heating rate can be controlled, as can the pressure inside the chamber. It will be understood that various process parameters discussed herein refer to processes performed using this type of apparatus. Persons of ordinary skill can easily adapt the parameters described herein to other types of drying apparatuses if desired.

Suitable temperatures and the amount of vacuum for primary and secondary drying can be readily determined by a person of ordinary skill. In general, the formulation is frozen at a temperature of about −30° C. or less, such as −40° C. or −50° C. The rate of cooling can affect the amount and size of ice crystals in the matrix. Primary drying is generally conducted at a temperature that is about 10° C., about 20° C., about 30° C., about 40° C. or about 50° C. warmer than the freezing temperature. In one aspect, the primary drying conditions can be set to maintain the anti-α4β7 antibody below the glass transition temperature or collapse temperature of the formulation. Above the collapse temperature, the amorphous frozen matrix can flow (collapse), with a result that the protein molecules may not be surrounded by a rigid, solid matrix, and the protein molecules may not be stable in the collapsed matrix. Also, the formulation can be difficult to fully dry if collapse occurs. The resulting higher amounts of moisture in the formulation can lead to higher rates of protein degradation and a decrease in the amount of time that the lyophilized product can be stored before its quality diminishes to unacceptable levels. In one aspect, the shelf temperature and chamber pressure are selected to maintain the product temperature below the collapse temperature during primary drying. The glass transition temperature of a frozen formulation can be measured by methods known in the art, e.g., by differential scanning calorimetry (DSC). The collapse temperature can be measured by methods known in the art, e.g. freeze-drying microscopy, optical coherence tomography. The drying step can remove at least 50%, at least 60%, at least 70% or more of the solvent. In one aspect, the primary drying step removes more than 80% of the solvent from the anti-α4β7 antibody formulation.

Vial size can be selected based on the surface area which will be exposed to the shelf and to the vacuum during lyophilization. Drying time is directly proportional to cake height, thus the vial size may be chosen based upon what is determined to be a reasonable cake height. A vial with a large diameter relative to volume can provide a high amount of contact with the shelf for efficient heat transfer during the lyophilization cycle. A dilute antibody solution in a high volume of liquid will require more time for drying. A balance in vial size versus formulation volume needs to be struck, because larger vials can be more expensive to store and ship and have a larger headspace to formulation ratio, and may expose a high proportion of the formulation to the degradative effects of moisture during long term storage. For a 165 mg dose, the vial size of the anti-α4β7 antibody formulation can be 3 mL, 5 ml or 10 ml. In one aspect, the vial size is 5 ml for a 160 mg/ml solution.

The principles for choosing a cartridge or syringe size for lyophilization are similar to that of the vial. The depth of the cake height will also increase the drying time as the height increases. The diameter and size of the syringe or cartridge must be balanced out with the final formulation volume. Larger diameters can increase the rate of moisture uptake in the lyophilized cake, thus increasing the degradative effects of moisture during storage. For a 165 mg dose, the anti-α4β7 antibody formulation volume can be 1 ml or 2 mL. In one aspect, the syringe or cartridge size is greater than 1 mL for a 160 mg/mL solution.

After lyophilization, the vial, syringe, or cartridge can be sealed, e.g., stoppered, under a vacuum. Alternatively, a gas, e.g., dry air or nitrogen, can be allowed into the container prior to sealing. Where oxidation is a concern, the gas allowed into the lyophilization chamber can comprise a gas which retards or prevents oxidation of the lyophilized product. In one aspect the gases are non-oxygenated gases, e.g., nitrogen, or an inert gas, e.g., helium, neon, argon, krypton or xenon. In another aspect, the gas is nitrogen or argon.

Treatment with the Antibody Formulation

In one aspect, the invention provides a method of treating a disease or disorder in a subject comprising administering to a subject the anti-α4β7 antibody formulation described herein in an amount effective to treat the disease or disorder, e.g., in humans. The human subject may be an adult (e.g., 18 years or older), an adolescent, or a child. The human subject may be a person 65 years or older. In contrast to alternative therapeutic dosing regimens, a human subject 65 years or older does not require any modification of the dosing regimen described herein, and may be administered the conventional anti-α4β7 antibody formulation described herein.

The subject may have had a lack of an adequate response with, loss of response to, or was intolerant to treatment with an immunomodulator, a TNF-α antagonist, or combinations thereof. The patient may have previously received treatment with at least one corticosteroid (e.g., prednisone) for the inflammatory bowel disease. An inadequate response to corticosteroids refers to signs and symptoms of persistently active disease despite a history of at least one 4-week induction regimen that included a dose equivalent to prednisone 30 mg daily orally for 2 weeks or intravenously for 1 week. A loss of response to corticosteroids refers to two failed attempts to taper corticosteroids to below a dose equivalent to prednisone 10 mg daily orally. Intolerance of corticosteroids includes a history of Cushing's syndrome, osteopenia/osteoporosis, hyperglycemia, insomnia and/or infection.

An immunomodulator may be, for example, oral azathioprine, 6-mercaptopurine, or methotrexate. An inadequate response to an immunomodulator refers to signs and symptoms of persistently active disease despite a history of at least one 8 week regimen or oral azathioprine (≥1.5 mg/kg), 6-mercaptopurine (≥0.75 mg/kg), or methotrexate (≥12.5 mg/week). Intolerance of an immunomodulator includes, but is not limited to, nausea/vomiting, abdominal pain, pancreatitis, LFT abnormalities, lymphopenia, TPMT genetic mutation and/or infection.

A TNF-α antagonist is, for example, an agent that inhibits the biological activity of TNF-α, and preferably binds INF-α, such as a monoclonal antibody, e.g., REMICADE (infliximab), HUMIRA (adalimumab), CIMZIA (certolizumab pegol), SIMPONI (golimumab) or a circulating receptor fusion protein such as ENBREL (etanercept). An inadequate response to a TNF-α antagonist refers to signs and symptoms of persistently active disease despite a history of at least one 4 week induction regimen of infliximab 5 mg/kg IV, 2 doses at least 2 weeks apart; one 80 mg subcutaneous dose of adalimumab, followed by one 40 mg dose at least two weeks apart; or 400 mg subcutaneously of certolizumab pegol, 2 doses at least 2 weeks apart. A loss of response to a INF-α antagonist refers to recurrence of symptoms during maintenance dosing following prior clinical benefit. Intolerance of a TNF-α antagonist includes, but is not limited to infusion related reaction, demyelination, congestive heart failure, and/or infection.

A loss of maintenance of remission, as used herein for ulcerative colitis subjects, refers to an increase in Mayo score of at least 3 points and a Modified Baron Score of at least 2.

In another aspect, the present invention provides anti-α4β7 antibody formulations which (1) can bind α4β7 integrin in vitro and/or in vivo; and (2) can modulate an activity or function of an α4β7 integrin, such as (a) binding function (e.g., the ability of α4β7 integrin to bind to MAdCAM (e.g., MAdCAM-1), fibronectin and/or VCAM-1) and/or (b) leukocyte infiltration function, including recruitment and/or accumulation of leukocytes in tissues (e.g., the ability to inhibit lymphocyte migration to intestinal mucosal tissue). In one embodiment, an antibody in the formulation can bind an α4β7 integrin, and can inhibit binding of the α4β7 integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). In another embodiment, an antibody in the formulation can bind an α4β7 integrin, and can selectively inhibit binding of the α4β7 integrin to one or more of its ligands (e.g., MAdCAM (e.g., MAdCAM-1), VCAM-1, fibronectin), thereby inhibiting leukocyte infiltration of tissues (including recruitment and/or accumulation of leukocytes in tissues). Such anti-α4β7 antibody formulations can inhibit cellular adhesion of cells bearing an α4β7 integrin to vascular endothelial cells in mucosal tissues, including gut-associated tissues, lymphoid organs or leukocytes (especially lymphocytes such as T or B cells) in vitro and/or in vivo. In yet another embodiment, the anti-α4β7 antibody formulation of the present invention can inhibit the interaction of α4β7 with MAdCAM (e.g., MAdCAM-1) and/or fibronectin. In still yet another embodiment, the anti-α4β7 antibody formulation of the present invention can inhibit the interaction of α4β7 with MAdCAM (e.g., MAdCAM-1) and/or fibronectin selectively, e.g., without inhibiting the interaction of α4β7 with VCAM.

The anti-α4β7 antibody formulations of the present invention can be used to modulate (e.g., inhibit (reduce or prevent)) binding function and/or leukocyte (e.g., lymphocyte, monocyte) infiltration function of α4β7 integrin. For example, humanized immunoglobulins which inhibit the binding of α4β7 integrin to a ligand (i.e., one or more ligands) can be administered according to the method in the treatment of diseases associated with leukocyte (e.g., lymphocyte, monocyte) infiltration of tissues (including recruitment and/or accumulation of leukocytes in tissues), particularly of tissues which express the molecule MAdCAM (e.g., MAdCAM-1).

An effective amount of an anti-α4β7 antibody formulation of the present invention (i.e., one or more) is administered to an individual (e.g., a mammal, such as a human or other primate) in order to treat such a disease. For example, inflammatory diseases, including diseases which are associated with leukocyte infiltration of the gastrointestinal tract (including gut-associated endothelium), other mucosal tissues, or tissues expressing the molecule MAdCAM (e.g., MAdCAM-1) (e.g., gut-associated tissues, such as venules of the lamina propria of the small and large intestine; and mammary gland (e.g., lactating mammary gland)), can be treated according to the present method. Similarly, an individual having a disease associated with leukocyte infiltration of tissues as a result of binding of leukocytes to cells (e.g., endothelial cells) expressing MAdCAM (e.g., MAdCAM-1) can be treated according to the present invention.

In one embodiment, diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis. In some embodiments, the inflammatory bowel disease is Crohn's disease or ulcerative colitis. The ulcerative colitis may be moderate to severely active ulcerative colitis. Treatment may result in mucosal healing in patients suffering from moderate to severely active ulcerative colitis. Treatment may also result in a reduction, elimination, or reduction and elimination of corticosteroid use by the patient.

Pancreatitis and insulin-dependent diabetes mellitus are other diseases which can be treated using the formulations of the invention. It has been reported that MAdCAM (e.g., MAdCAM-1) is expressed by some vessels in the exocrine pancreas from NOD (nonobese diabetic) mice, as well as from BALB/c and SJL mice. Expression of MAdCAM (e.g., MAdCAM-1) was reportedly induced on endothelium in inflamed islets of the pancreas of the NOD mouse, and MAdCAM (e.g., MAdCAM-1) was the predominant addressin expressed by NOD islet endothelium at early stages of insulitis (Hanninen, A., et al., *J. Clin. Invest.*, 92: 2509-2515 (1993)). Treatment of NOD mice with either anti-MAdCAM or anti-β7 antibodies prevented the development of diabetes (Yang et al., *Diabetes*, 46:1542-1547 (1997)). Further, accumulation of lymphocytes expressing α4β7 within islets was observed, and MAdCAM-1 was implicated in the binding of lymphoma cells via α4β7 to vessels from inflamed islets (Hanninen, A., et al., *J. Clin. Invest.*, 92: 2509-2515 (1993)) or to the gastrointestinal tract in mantle cell lymphoma (Geissmann et al., *Am. J. Pathol.*, 153:1701-1705 (1998)).

Examples of inflammatory diseases associated with mucosal tissues which can be treated using a formulation of the invention include cholecystitis, cholangitis (Adams and Eksteen Nature Reviews 6:244-251 (2006) Grant et al., *Hepatology* 33:1065-1072 (2001)), e.g., primary sclerosing cholangitis, Behcet's disease, e.g., of the intestine, or pericholangitis (bile duct and surrounding tissue of the liver), and graft versus host disease (e.g., in the gastrointestinal tract (e.g., after a bone marrow transplant) (Petrovic et al. *Blood* 103:1542-1547 (2004)). As seen in Crohn's disease, inflammation often extends beyond the mucosal surface, accordingly chronic inflammatory diseases, such as sarcoidosis, chronic gastritis, e.g., autoimmune gastritis (Katakai et al., *Int. Immunol.*, 14:167-175 (2002)) and other idiopathic conditions can be amenable to treatment.

The invention also relates to a method of inhibiting leukocyte infiltration of mucosal tissue. The invention also relates to a method for treating cancer (e.g., an α4β7 positive tumor, such as a lymphoma). Other examples of inflammatory diseases associated with mucosal tissues which can be treated using a formulation of the invention include mastitis (mammary gland) and irritable bowel syndrome.

Diseases or pathogens whose etiologies exploit the interaction of MAdCAM (e.g., MAdCAM-1) with α4β7 can be treated with an anti-α4β7 antibody in a formulation described herein. Examples of such diseases include immunodeficiency disorders, such as caused by human immunodeficiency virus (See, e.g., WO2008140602).

A formulation of the invention is administered in an effective amount which inhibits binding of α4β7 integrin to a ligand thereof. For therapy, an effective amount will be sufficient to achieve the desired therapeutic (including prophylactic) effect (such as an amount sufficient to reduce or prevent α4β7 integrin-mediated binding and/or signaling, thereby inhibiting leukocyte adhesion and infiltration and/or associated cellular responses). An effective amount of an anti-α4β7 antibody, e.g., an effective titer sufficient to maintain saturation, e.g., neutralization, of α4β7 integrin, can induce clinical response or remission in inflammatory bowel disease. An effective amount of an anti-α4β7 antibody can lead to mucosal healing in ulcerative colitis or Crohn's disease. A formulation of the invention can be administered in a unit dose or multiple doses. The dosage can be determined by methods known in the art and can be dependent, for example, upon the individual's age, sensitivity, tolerance and overall well-being. Examples of modes of administration include topical routes such as nasal or inhalational or transdermal administration, enteral routes, such as through a feeding tube or suppository, and parenteral routes, such as intravenous, intramuscular, subcutaneous, intraarterial, intraperitoneal, or intravitreal administration. Suitable dosages for antibodies can be from about 0.1 mg/kg body weight to about 10.0 mg/kg body weight per treatment, for example about 2 mg/kg to about 7 mg/kg, about 3 mg/kg to about 6 mg/kg, or about 15 to about 5 mg/kg. In particular embodiments, the dose administered is about 0.3 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. The total dose may be about 22 mg, about 50 mg, about 72 mg, about 125 mg, about 165 mg, or about 432 mg. The total dose may be at least 77 mg, at least 125 mg or at least 356 mg. In one embodiment, the total dose is 165 mg. In another embodiment, the total dose is 108 mg. In another embodiment, the total dose is 216 mg.

Modeling and simulations (BERKELEY MADONNA™ software, University of California) using pharmacokinetic (PK) data from studies of availability of anti-α4β7 antibody over time after administration can assess potential dosing regimens for subcutaneous or intramuscular administration. PK data can be evaluated for induction and for maintenance regimens. Another modeling approach is population pharmacokinetic/pharmacodynamic analysis (NONMEM® nonlinear mixed effects modeling tool, ICON plc, Dublin, Ireland). Both exposure levels and trough levels can be analyzed.

Typically, after target, e.g., α4β7 integrin, saturation is reached, the antibody concentration in the blood has a linear relationship to the dose administered. An anti-α4β7 antibody administered by the subcutaneous or intramuscular route has about 60% to about 90% of the bioavailability of an anti-α4β7 antibody administered by an intravenous route. In an example of this relationship, if an IV dose is assumed to have a 100% bioavailability and a subcutaneous dose is found to have a 69.5% bioavailability, then a 300 mg intravenous dose can be matched with a 432 mg dose by subcutaneous administration. Accordingly, a 150 mg intravenous dose can be matched by a 216 mg subcutaneous dose at 69.5% relative bioavailability. Similarly, if a subcutaneous dose is found to have a 75% availability and an intramuscular dose is found to have an 80% bioavailability, then to match a 300 mg intravenous dose, the subcutaneous dose can be 400 mg and the intramuscular dose can be 375 mg. Tables 40-43 in the examples illustrate these relationships and provide useful doses and dosing regimens of an anti-α4β7 antibody.

In some aspects, the dosing regimen has two phases, an induction phase and a maintenance phase. In the induction phase, the antibody or antigen-binding fragment thereof is administered in a way that quickly provides an effective amount of the antibody or antigen binding fragment thereof suitable for certain purposes, such as inducing immune tolerance to the antibody or antigen-binding fragment thereof or for inducing a clinical response and ameliorating inflammatory bowel disease symptoms. A patient can be administered an induction phase treatment when first being treated by an anti-α4β7 antibody, when being treated after a long absence from therapy, e.g., more than three months, more than four months, more than six months, more than nine months, more than one year, more than eighteen months or more than two years since anti-α4β7 antibody therapy or during maintenance phase of anti-α4β7 antibody therapy if there has been a return of inflammatory bowel disease symptoms, e.g., a relapse from remission of disease. In some embodiments, the induction phase regimen results in a higher mean trough serum concentration, e.g., the concentration just before the next dose, than the mean steady state trough serum concentration maintained during the maintenance regimen.

In the maintenance phase, the antibody or antigen-binding fragment thereof is administered in a way that continues the response achieved by induction therapy with a stable level of antibody or antigen-binding fragment thereof. A maintenance regimen can prevent return of symptoms or relapse of inflammatory bowel disease. A maintenance regimen can provide convenience to the patient, e.g., be a simple dosing regimen or require infrequent trips for treatment. In some embodiments, the maintenance regimen can include administration of the anti-α4β7 antibody or antigen-binding fragment thereof, e.g., in a formulation described herein, by a strategy selected from the group consisting of low dose, infrequent administration, self-administration and a combination any of the foregoing.

In one embodiment, e.g., during an induction phase of therapy, the dosing regimen provides an effective amount of an anti-α4β7 antibody or antigen-binding fragment in a formulation described herein for inducing remission of an inflammatory bowel disease in a human patient. In some embodiments, the effective amount of the anti-α4β7 antibody is sufficient to achieve about 5 μg/ml to about 60 μg/ml, about 15 μg/ml to about 45 μg/ml, about 20 μg/ml to about 30 μg/ml, or about 25 μg/ml to about 35 μg/ml mean trough serum concentration of the anti-α4β7 antibody by the end of the induction phase. The duration of induction phase can be about four weeks, about five weeks, about six weeks, about seven weeks, or about eight weeks of treatment. In some embodiments, the induction regimen can utilize a strategy selected from the group consisting of high dose, frequent administration, and a combination of high dose and frequent administration of the anti-α4β7 antibody or antigen-binding fragment thereof, e.g., in a formulation described herein. Induction dosing can be once, or a plurality of more than one dose, e.g., at least two doses. During induction phase, a dose can be administered once per day, every other day, twice per week, once per week, once every ten days, once every two weeks or once every three weeks. In some embodiments, the induction doses are administered within the first two weeks of therapy with the anti-α4β7 antibody. In one embodiment, induction dosing can be once at initiation of treatment (day 0) and once at about two weeks after initiation of treatment. In another embodiment, the induction phase duration is six weeks. In another embodiment, the induction phase duration is six weeks and a plurality of induction doses are administered during the first two weeks.

In some embodiments, e.g., when initiating treatment of a patient with severe inflammatory bowel disease (e.g., in patients who have failed anti-TNFα therapy), the induction phase needs to have a longer duration than for patients with mild or moderate disease. In some embodiments, the induction phase for a patient with a severe disease can have a duration of at least 6 weeks, at least 8 weeks, at least 10 weeks, at least 12 weeks or at least 14 weeks. In one embodiment, an induction dosing regimen for a patient with a severe disease can include a dose at week 0 (initiation of treatment), a dose at week 2 and a dose at week 6. In another embodiment, an induction dosing regimen for a patient with a severe disease can comprise a dose at week 0 (initiation of treatment), a dose at week 2, a dose at week 6 and a dose at week 10.

In one embodiment, e.g., during a maintenance phase of therapy, the dosing regimen maintains a mean steady state trough serum concentration, e.g., the plateau concentration just before the next dose, of about 5 to about 25 μg/mL, about 7 to about 20 μg/mL, about 5 to about 10 μg/mL, about 10 to about 20 μg/mL, about 15 to about 25 μg/mL or about 9 to about 13 μg/mL of anti-α4β7 antibody. In another embodiment, the dosing regimen e.g., during a maintenance phase of therapy, maintains a mean steady state trough serum concentration of about 20 to about 30 μg/mL, about 20 to about 55 μg/mL, about 30 to about 45 μg/mL, about 45 to about 55 μg/mL or about 35 to about 40 μg/mL of anti-α4β7 antibody. In another embodiment, the dosing regimen e.g., during a maintenance phase of therapy, maintains a long term mean serum concentration, e.g., exposure (e.g., area under the curve–concentration-time) of about 15 to about 40 μg/mL, about 10 to about 50 μg/mL, about 18 to about 26 μg/mL, or about 22 to about 33 μg/mL of anti-α4β7 antibody. In yet another embodiment, the dosing regimen e.g., during a maintenance therapy, maintains a long term mean serum concentration, e.g., exposure (e.g., area under the curve–concentration-time) of about 35 to about 90 μg/mL, about 45 to about 75 μg/mL, about 52 to about 60 μg/mL or about 50 to about 65 μg/mL of anti-α4β7 antibody.

The final dosage form can comprise the entire dose in about 0.5 ml, in about 1 ml, in about 1.5 ml in about 2 ml, in about 2.5 ml, in about 3 ml of the antibody formulation.

The final dosage form for intravenous administration may be at a concentration of between about 1.0 mg/ml to about 1.4 mg/ml, about 1.0 mg/ml to about 1.3 mg/ml, about 1.0 mg/ml to about 1.2 mg/ml, about 1.0 to about 1.1 mg/ml, about 1.1 mg/ml to about 1.4 mg/ml, about 1.1 mg/ml to about 1.3 mg/ml, about 1.1 mg/ml to about 1.2 mg/ml, about 1.2 mg/ml to about 1.4 mg/ml, about 1.2 mg/ml to about 1.3 mg/ml, or about 1.3 mg/ml to about 1.4 mg/ml. The final dosage form may be at a concentration of about 0.6 mg/ml, 0.8 mg/ml, 1.0 mg/ml, 1.1 mg/ml, about 1.2 mg/ml, about 1.3 mg/ml, about 1.4 mg/ml, about 1.5 mg/ml, about 1.6 mg/ml, about 1.8 mg/ml or about 2.0 mg/ml.

The dose can be administered once per week, once every 2 weeks, once every 3 weeks, once every 4 weeks, once every 6 weeks, once every 8 weeks or once every 10 weeks. A higher or more frequent dose, e.g., every other day, once per week, once every 2 weeks, once every 3 weeks or once every 4 weeks can be useful for inducing remission of active disease or for treating a new patient, e.g., for inducing tolerance to the anti-α4β7 antibody. A dose once every 2 weeks, once every 3 weeks, once every 4 weeks, once every 5 weeks, once every 6 weeks, once every 8 weeks or once every 10 weeks, can be useful for preventative therapy, e.g., to maintain remission of a patient with chronic disease. In one aspect, the treatment regimen is treatment at day 0, about week 2, about week 6 and every 1 or 2 weeks thereafter. In another aspect, the induction treatment regimen is treatment every other day for a total of 6 treatments.

The dosing regimen can be optimized to induce a clinical response and clinical remission in the inflammatory bowel disease of the patient. In some embodiments, the dosing regimen does not alter the ratio of CD4 to CD8 in cerebrospinal fluid of patients receiving treatment.

In some aspects, a durable clinical remission, for example, a clinical remission which is sustained through at least two, at least three, at least four visits with a caretaking physician within a six month or one year period after beginning treatment, may be achieved with an optimized dosing regimen.

In some aspects, a durable clinical response, for example, a clinical response which is sustained for at least 6 months, at least 9 months, at least a year, after the start of treatment, may be achieved with an optimized dosing regimen.

The formulation may be administered subcutaneously in single or multiple injections. For example, the volume of a single injection may range from about 0.5 ml to about 3 ml. In an embodiment, the volume of a single injection may be about 0.6 ml to about 1.1 ml or about 1 ml to about 3 mi. In one aspect, the volume of a single injection is about 1 ml. The gauge of the needle used to administer the formulation subcutaneously may be about 25, about 26, about 27, about 28, about 29 or about 30 G.

The formulation may be administered intramuscularly in single or multiple injections. For example, the volume of a single injection may range from about 0.5 ml to about 5 ml. In an embodiment, the volume of a single injection may be about 2 ml to about 5 ml, about 0.6 ml to about 1.1 ml or about 1 ml to about 3 ml. In one aspect, the volume of a single injection is about 1 ml, about 2 ml, about 3 ml, about 4 ml, or about 5 ml. The needle used to administer the formulation intramuscularly may be about ⅝", about ⅞", about 1", about 1.25", about 1.5", about 2", or about 3". The gauge of the needle may be between 20-22 G for intramuscular administration.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human α4β7 integrin, wherein the humanized immunoglobulin or antigen-binding fragment thereof is administered to the patient according to the following dosing regimen: (a) initial doses of 165 mg of the humanized immunoglobulin or antigen-binding fragment thereof as a subcutaneous injection every other day for six doses; (b) followed by a seventh and subsequent doses of 165 mg of the humanized immunoglobulin or antigen-binding fragment thereof as a subcutaneous injection every two weeks or every four weeks as needed; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In one aspect, the invention relates to a method for treating a human patient suffering from inflammatory bowel disease, wherein the method comprises the step of administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to the following dosing regimen: (a) an initial intravenous dose of 300 mg of the humanized immunoglobulin or antigen-binding fragment thereof as an intravenous infusion; (b) followed by a second intravenous subsequent dose of 300 mg of the humanized immunoglobulin or antigen-binding fragment thereof as an intravenous infusion at about two weeks after the initial dose; (c) followed beginning at week six by a third and subsequent doses of 165 mg of the humanized immunoglobulin or antigen-binding fragment thereof as a subcutaneous injection every week, every two weeks or every three weeks as needed; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a mean steady state serum trough concentration of about 9 to about 13 µg/mL of the antibody or antigen-binding fragment thereof; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In another aspect, the invention relates to a dosing regimen for the therapeutic treatment of inflammatory bowel disease, wherein the dosing regimen comprises the step of: administering to a patient suffering from inflammatory bowel disease, a humanized immunoglobulin or antigen-binding fragment thereof having binding specificity for human α4β7 integrin, wherein the humanized immunoglobulin or antigen-binding fragment comprises an antigen-binding region of nonhuman origin and at least a portion of an antibody of human origin, wherein the humanized immunoglobulin or antigen-binding fragment thereof is administered to the patient according to a subcutaneous or intramuscular dosing regimen which maintains a steady state serum trough concentrations of about 35 to about 40 µg/mL of the antibody or antigen-binding fragment thereof; wherein the dosing regimen induces a clinical response and clinical remission in the inflammatory bowel disease of the patient; and further wherein the humanized immunoglobulin or antigen-binding fragment has binding specificity for the α4β7 complex, wherein the antigen-binding region comprises three complementarity determining regions (CDR1, CDR2, and CDR3) of a light chain variable region and three complementarity determining regions (CDR1, CDR2, and CDR3) of a heavy chain variable region of the amino acid sequence set forth below: light chain: CDR1 SEQ ID NO:9, CDR2 SEQ ID NO:10, CDR3 SEQ ID NO:11; heavy chain: CDR1 SEQ ID NO:12, CDR2 SEQ ID NO:13, CDR3 SEQ ID NO:14.

In some embodiments, the method of treatment, dose or dosing regimen reduces the likelihood that a patient will develop a HAHA response to the anti-α4β7 antibody. The development of HAHA, e.g., as measured by antibodies reactive to the anti-α4β7 antibody, can increase the clearance of the anti-α4β7 antibody, e.g., reduce the serum concentration of the anti-α4β7 antibody, e.g., lowering the number of anti-α4β7 antibody bound to α4β7 integrin, thus making the treatment less effective. In some embodiments, to prevent HAHA, the patient can be treated with an induction regimen followed by a maintenance regimen. In some embodiments, there is no break between the induction regimen and the maintenance regimen. In some embodiments, the induction regimen comprises administering a plurality of doses of anti-α4β7 antibody to the patient. To prevent HAHA, the patient can be treated with a high initial dose, e.g., at least 1.5 mg/kg, at least 2 mg/kg, at least 2.5 mg/kg, at least 3 mg/kg, at least 5 mg/kg, at least 8 mg/kg, at least 10 mg/kg or about 2 to about 6 mg/kg, or frequent initial administrations, e.g., about once per week, about once every two weeks or about once every three weeks, of the standard dose when beginning therapy with an anti-α4β7 antibody. In some embodiments, the method of treatment maintains at least 30%, at least 40%, at least 50%, at least 60%, at least 70%, at least 80%, at least 90% or at least 95% of patients as HAHA-negative. In other embodiments, the method of treatment maintains patients as HAHA-negative for at least 6 weeks, at least 10 weeks at least 15 weeks, at least six months, at least 1 year, at least 2 years, or for the duration of therapy. In some embodiments, the patients, or at least 30%, at least 40%, at least 50% or at least 60% of patients who develop HAHA maintain a low titer, e.g., ≤125, of anti-α4β7 antibody. In an embodiment, the method of treatment maintains at least 70% of patients as HAHA-negative for at least 12 weeks after beginning therapy with an anti-α4β7 antibody.

The formulation may be administered to an individual (e.g., a human) alone or in conjunction with another agent. A formulation of the invention can be administered before, along with or subsequent to administration of the additional agent. In one embodiment, more than one formulation which inhibits the binding of α4β7 integrin to its ligands is administered. In such an embodiment, an agent, e.g., a monoclonal antibody, such as an anti-MAdCAM or an anti-VCAM-1 monoclonal antibody can be administered. In another embodiment, the additional agent inhibits the binding of leukocytes to an endothelial ligand in a pathway different from the α4β7 pathway. Such an agent can inhibit the binding, e.g. of chemokine (C—C motif) receptor 9 (CCR9)-expressing lymphocytes to thymus expressed chemokine (TECK or CCL25) or an agent which prevents the binding of LFA-1 to intercellular adhesion molecule (ICAM). For example, an anti-TECK or anti-CCR9 antibody or a small molecule CCR9 inhibitor, such as inhibitors disclosed in PCT publication WO03/099773 or WO04/046092, or anti-ICAM-1 antibody or an oligonucleotide which prevents expression of ICAM, is administered in addition to a formulation of the present invention. In yet another embodiment, an additional active ingredient (e.g., an anti-inflammatory compound, such as sulfasalazine, azathioprine, 6-mercaptopurine, 5-aminosalicylic acid containing anti-inflammatories, another non-steroidal anti-inflammatory compound, a steroidal anti-inflammatory compound, or antibiotics commonly administered for control of IBD (e.g. ciprofloxacin, metronidazole), or another biologic agent (e.g. TNF alpha antagonists) can be administered in conjunction with a formulation of the present invention.

In an embodiment, the dose of the co-administered medication can be decreased over time during the period of treatment by the formulation comprising the anti-α4β7 antibody. For example, a patient being treated with a steroid (e.g. prednisone, prednisolone) at the beginning, or prior to, treating with the anti-α4β7 antibody formulation would undergo a regimen of decreasing doses of steroid beginning as early as 6 weeks of treatment with the anti-α4β7 antibody formulation. The steroid dose will be reduced by about 25% within 4-8 weeks of initiating tapering, by 50% at about 8-12 weeks and 75% at about 12-16 weeks of tapering during treatment with the anti-α4β7 antibody formulation. In one aspect, by about 16-24 weeks of treatment with the anti-α4β7 antibody formulation, the steroid dose can be eliminated. In another example, a patient being treated with an anti-inflammatory compound, such as 6-mercaptopurine at the beginning, or prior to, treating with the anti-α4β7 antibody formulation would undergo a regimen of decreasing doses of anti-inflammatory compound similar to the tapering regimen for steroid dosing as noted above.

In one embodiment, the method comprises subcutaneously administering or intramuscularly administering an effective amount of a formulation of the invention to a patient. In another embodiment, the formulation can be prepared for self-administration.

If the formulation is in a solid, e.g., dry state, the process of administration can comprise a step of converting the formulation to a liquid state. In one aspect, a dry formulation can be reconstituted, e.g., by a liquid as described above, for use in injection, e.g. intravenous, intramuscular or subcutaneous injection. In another aspect, a solid or dry formulation can be administered topically, e.g., in a patch, cream, aerosol or suppository.

The invention also relates to a method for treating a disease associated with leukocyte infiltration of tissues expressing the molecule MAdCAM (e.g., MAdCAM-1). The method comprises administering to a patient in need thereof an effective amount of an anti-α4β7 antibody formulation of the invention. In an embodiment, the disease is graft versus host disease. In some embodiments, the disease is a disease associated with leukocyte infiltration of tissues as a result of binding of leukocytes expressing α4β7 integrin to gut-associated endothelium expressing the molecule MAdCAM (e.g., MAdCAM-1). In other embodiments, the disease is gastritis (e.g., eosinophilic gastritis or autoimmune gastritis), pancreatitis, or insulin-dependent diabetes mellitus. In yet other embodiments, the disease is cholecystitis, cholangitis, or pericholangitis.

The invention also relates to a method for treating inflammatory bowel disease in a patient. In one embodiment, the method comprises subcutaneously administering to the patient an effective amount of an anti-α4β7 antibody formulation of the invention. In some embodiments, the inflammatory bowel disease is ulcerative colitis or Crohn's disease. In other embodiments, the inflammatory bowel disease is Celiac disease, enteropathy associated with seronegative arthropathies, microscopic or collagenous colitis, gastroenteritis (e.g., eosinophilic gastroenteritis), or pouchitis.

In some embodiments, treatment with an anti-α4β7 antibody does not alter the ratio of CD4:CD8 lymphocytes. CD4:CD8 ratios can be measured in blood, lymph node aspirate, and cerebro-spinal fluid (CSF). The CSF CD4+:CD8+ lymphocyte ratios in healthy individuals are typically greater than or equal to about 1. (Svenningsson et al., J. Neuroimmunol. 1995; 63:39-46; Svenningsson et al., Ann Neurol. 1993; 34:155-161). An immunomodulator can alter the CD4:CD8 ratio to less than 1.

Articles of Manufacture

In another aspect, the invention is an article of manufacture which contains the pharmaceutical formulation of the present invention and provides instructions for its use. The article of manufacture comprises a container. Suitable containers include, for example, bottles, vials (e.g., dual chamber vials, a vial of liquid formulation with or without a needle, a vial of solid formulation with or without a vial of reconstitution liquid with or without a needle), syringes (such as dual chamber syringes, preloaded syringes, an auto-injector), cartridges, and test tubes. The container may be formed from a variety of materials such as glass, metal or plastic. The container holds the formulation and a label on, or associated with, the container may indicate directions for use. In another embodiment, the formulation can be prepared for self-administration and/or contain instructions for self-administration. In one aspect, the container holding the formulation may be a single-use vial. In another aspect, the container holding the formulation may be a multi-use vial, which allows for repeat administration (e.g., from 2-6 administrations) of the formulation, e.g., using more than one portion of a reconstituted formulation. The article of manufacture may further include other materials desirable from a commercial and user standpoint, including other buffers, diluents, filters, needles, syringes and package inserts with instructions for use as noted in the previous section.

In one embodiment, the article of manufacture is a syringe with a needle. The gauge of the needle may be 25 G, 26 G, 27 G, 29 G, 30 G. A thin wall needle, e.g, 19 G or 23 G, or greater, can facilitate injection of a high viscosity formulation. In one aspect, the needle gauge is 27 G or greater. Needle length can be suitable for subcutaneous administration, and can be about ½ inch, about ⅝ inch or 1 inch long. In some embodiments, the syringe is a pre-filled syringe.

Pre-Filled Syringe Product Development

In some aspects, there are several product attributes that are desired for a protein product (e.g., an anti-α4β7 antibody) in a pre-filled syringe (PFS) (e.g., for use in administration of a formulation for subcutaneous or intramuscular delivery). It is helpful to balance some of the attributes to mitigate competing effects. For example, when a low injection volume is desired, a high protein concentration for the formulation may be preferred. However, in the case of a high protein concentration, there can be higher rates of impurity formation (e.g., aggregated impurities that leach into formulation from syringe) and higher manual forces needed to operate the syringe. A small needle size used for patient comfort at the injection site, may require high forces to operate the syringe. An understanding of how product stability and performance is affected by both formulation and syringe parameters such as protein concentration, pH, and needle inner diameter aids in the development of a protein product (e.g., an anti-α4β7 antibody in a pre-filled syringe).

In one aspect, a method of developing a protein product (e.g., an anti-α4β7 antibody) for use in a pre-filled syringe comprises varying syringe parameters and formulation parameters together, e.g., in a coordinate fashion or simultaneously. This can lead to a better understanding of the range of protein stability and product performance that can be expected from a protein product in a pre-filled syringe than if each aspect is varied separately or in series.

Figure 15:
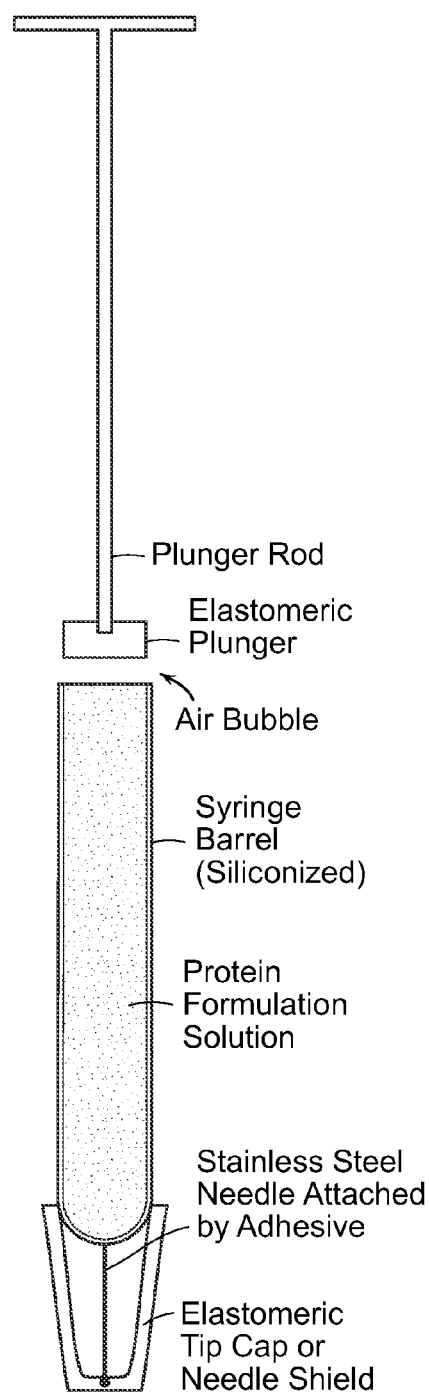
FIG. 15 shows components of a protein product in a pre-filled syringe.

The development of a pre-filled syringe product (e.g., an anti-α4β7 antibody) relates to understanding that at some point, there is a liquid formulation in contact with several components of the pre-filled syringe (FIG. 15). For example, the formulation can be in contact with a syringe barrel, which can be constructed of glass (e.g., type I borosilicate glass) or plastic (e.g., cyclic olefin polymer (COP), cyclic olefin copolymer (COC), polypropylene or polytetrafluoroethylene). The formulation can be in contact with the syringe, plunger and/or tip cap, which can be elastomeric (e.g., of the same or different materials (e.g., plastic, such as polyethylene, polystyrene or polypropylene or elastic, such as rubber (natural, synthetic, butyl) or silicone)). The formulation may be in contact with a lubricant that is added to an inner surface of the barrel for ease of plunger movement. The lubricant can be, for example, silicone oil, mineral oil or glycerin. In the embodiment of a staked needle syringe, there can be a metal alloy needle (e.g., stainless steel needle and adhesive used to glue the needle in place). A consideration for a protein product in a pre-filled syringe is that the liquid protein solution is in direct contact with one or more of these syringe components throughout the shelf life of the product. Both the formulation and syringe components can have an impact on the stability of the product.

Formulation parameters that can affect pre-filled syringe product stability include protein concentration, pH, buffer type, buffer concentration, ionic strength, stabilizer type, and stabilizer concentration. Examples of stabilizers for protein formulations include, for example, ionic salts, polysaccharides, amino acids, antioxidants, chelators, and surfactants as described in earlier sections.

Syringe components that can affect pre-filled syringe product stability include, for example, lubricant, composition of plunger and tip cap, and impurities. The amount of lubricant (e.g., silicone oil on the syringe barrel) may affect product stability. The composition of the plunger and tip cap, which can affect oxygen permeability of these components and introduce leachables from these components into the protein product (e.g., the anti-α4β7 antibody formulation) may also affect product stability. Another syringe parameter that can affect product stability includes the type and/or amount of impurities (e.g., heavy metal (e.g., tungsten)) that can leach into the product formulation (e.g., from in the barrel (e.g., glass barrel) and/or needle (e.g., stainless steel needle)). (See also Ludwig et al. *J. Pharm. Sci.* 99:1721-1733 (2010); Nashed-Samuel et al., *American Pharmaceutical Review* January/February:74-80 (2011); Badkar et al. *AAPS Pharm Sci Tech* 12:564-572)

A pre-filled syringe can be injected manually or used with an auto-injector device. Functional testing of the pre-filled syringe includes measuring the breakloose force, the force required to begin movement of the plunger, and the gliding force, the force needed to inject the contents of the syringe at a constant rate. The mechanical performance of the pre-filled syringe can be dependent on several formulation and syringe parameters such as the viscosity of the formulation and the amount of lubricant (e.g., silicone oil) in the syringe.

Several attributes of protein products in pre-filled syringes and formulation or syringe factors that can impact those product attributes are shown in Table 1. Many product attributes can be a complex function of several formulation and syringe parameters. For example, syringe gliding force is a function of formulation viscosity, although viscosity can be dependent on several formulation factors, such as protein concentration, stabilizer concentrations, and pH.

TABLE 1

Product Attributes for Protein Products in Pre-filled Syringes and the Potential Formulation and Syringe Parameters that may Impact These Attributes

| Product Attribute | Protein Formulation Parameters that may Impact Product Attribute | Syringe Parameters that may Impact Product Attribute |
| --- | --- | --- |
| Osmolality | Stabilizer concentrations, pH, protein concentration | None |
| Viscosity | Stabilizer concentrations, pH, protein concentration | None |
| Syringe Break Loose and Gliding Force | Viscosity, protein concentration, surfactant concentration | Injection speed, needle length, needle ID, syringe barrel ID, silicone oil amount, plunger formulation and shape |
| Rate of Protein Deamidation | Stabilizer concentrations, pH, protein concentration | None |
| Rate of Protein Oxidation | Stabilizer/antioxidant concentrations, pH, protein concentration, surfactant concentration, dissolved oxygen | Plunger and tip cap formulation (oxygen permeability), heavy metal impurity levels, size of air bubble |
| Rate of Soluble Aggregate Formation | Stabilizer concentrations, pH, protein concentration, surfactant concentration, dissolved oxygen in solution | Silicone oil amount, heavy metal impurity levels, size of air bubble |
| Rate of Sub-visible and Visible Proteinaceous Particulate Formation | Stabilizer concentrations, pH, protein concentration, surfactant concentration | Silicone oil amount, Heavy metal impurity levels, , size of air bubble, syringe internal surface area |

In one aspect, a surfactant, such as polysorbate 20 or polysorbate 80 can be added to protein formulations in pre-filled syringes (e.g., to prevent protein molecules from adsorbing and denaturing at the liquid/air and/or liquid/lubricant (e.g., silicone oil) interfaces). Surface adsorption and denaturation of protein molecules can be one mechanism for the nucleation of sub-visible and visible proteinaceous particles. Addition of a surfactant to a pre-filled syringe, therefore, can reduce the formation of sub-visible and visible particles in pre-filled syringe products. In one embodiment, a small amount of surfactant can emulsify lubricant (e.g., silicone oil droplets in the solution and thereby reduce the formation of subvisible and visible lubricant (e.g., silicone oil droplets)) (Ludwig et al., supra). In another embodiment, the amount of surfactant in a formulation is minimized, due to potential harmful effects of high amounts of surfactants on protein formulations. Peroxide impurities present in polysorbates can lead to increased protein oxidation (Wang and Wang *J. Pharm. Sci.* 91:2252-2264 (2002)). High amounts of surfactant can emulsify a significant amount of silicone oil from the walls of the syringe and lead to an increase in the functional gliding force over the shelf life. Product development studies should be designed to examine the effect of varying surfactant levels on both product stability and syringe performance.

The complex interactions between the formulation and the syringe parameters in protein/PFS systems are amenable to examination of these systems using a Quality by Design (QbD) or Design of Experiments (DOE) approach. Studies can be designed that simultaneously vary formulation and syringe parameters to gain a better understanding of these complex systems. This results in a comprehensive approach to the development of pre-filled syringe products. Table 2 shows an example of the input parameters and levels that may go into a design of experiment for a pre-filled syringe product and an example of the analytical testing to be employed. Depending on the type of experimental design that is used for QbD study, the number of experiments could vary from 9 for a screening design to 81 for a full-factorial design (all possible combinations). The higher the number of experiments, the higher the number of interactions between product parameters that can be resolved. Software designed for this analysis, for example, JMP® statistical discovery software (Cary, N.C.), can be helpful for QbD studies. This analysis results in a quantitative understanding of how formulation and syringe parameters interact to impact product attributes.

TABLE 2

Example of an Experimental Design for a Liquid Protein Product in a Pre-filled Syringe

| Formulation Input Parameters | Levels | Analytical Testing |
|---|---|---|
| Protein Concentration | 50, 100, 150 mg/mL | Protein stability by size exclusion chromatography and ion exchange chromatography |
| pH | 5.5, 6.5, 7.5 | |
| Surfactant Concentration | 0.01, 0.08, 0.15% | Break loose and gliding force over time using force testing |
| Amount of Silicone Oil in Syringe | 0.2, 0.5, 0.8 mg/syringe | Formation of sub-visible proteinaceous particles and silicone oil droplets over time using microflow imaging or/coulter counter |

An example of a predictive model that can be obtained from the example experiment shown in Table 2 is given below, where $C_0$ are numerical constants.

Soluble Aggregate Formation over Time=$C_0+C_1$[Protein Concentration]+$C_2$[Protein Concentration]$^2$+$C_3$[pH]+$C_4$[Surfactant Concentration]+$C_5$[Lubricant Amount]

Numerous syringe parameters can affect product stability and performance, therefore an embodiment includes characterization of how the allowable tolerances in syringe parameters affect product stability and performance. The amount of lubricant (e.g., silicone oil) on the syringe barrel may vary 50-100% from syringe to syringe. This variation in the amount may affect several product characteristics as shown in Table 1. The inner diameter of the syringe barrel can vary from syringe to syringe which affects injection forces. For staked-needle syringes, the needle inner diameter may vary from lot to lot or from manufacturer to manufacturer, which will affect injection forces. By using a QbD approach to examine how syringe parameters affect performance, predictive models can be obtained that can be used to estimate how the allowable tolerances in syringe parameters may affect product performance. Predictive models that are obtained using a QbD approach can be used to select formulation and syringe parameters that meet desired product attributes and to predict product stability and performance.

The pre-filled syringe may contain an addition of silicone emulsion or tungsten to the protein formulation. Exemplary amounts of silicone that may be present in the pre-filled syringe range from about 0.3 mg to about 0.8 mg. In one aspect, the amount of silicone that may be present in the pre-filled syringe is about 0.3 mg, about 0.4 mg, about 0.5 mg, about 0.6 mg, about 0.7 mg, or about 0.8 mg. In another aspect, the viscosity of the formulation will range from 2 to 60 cP, resulting in injection forces of 5N to 80N at a speed of 200 mm/min. In still yet another aspect, the viscosity of the formulation will range from 4 to 27 cP resulting in injection forces of 10 N to 40 N at a speed of 200 mm/min.

The invention will be more fully understood by reference to the following examples. They should not, however, be construed as limiting the scope of the invention. All literature and patent citations are incorporated herein by reference.

Protocol for Making Formulation

A solution of anti-α4β7 antibody is diafiltered in a tangential flow filtration system to reach a specified concentration in citrate, histidine, arginine buffer, then pooled and mixed with a solution of polysorbate 80 in citrate, histidine, arginine buffer. The solution is stored at −70° C. in either 2 L or 5 L bottles. The solution is then thawed and filtered twice through a 0.2 μm filter. Approximately 1.0 mL is filled into a sterilized syringe and closed with a sterilized plunger (stopper). The formulation is stored and the final drug product is shipped in syringes at 2-8° C.

EXAMPLES

Example 1

Formulation Manufacturing

Factors

Excipient Concentrations

Figure 6:
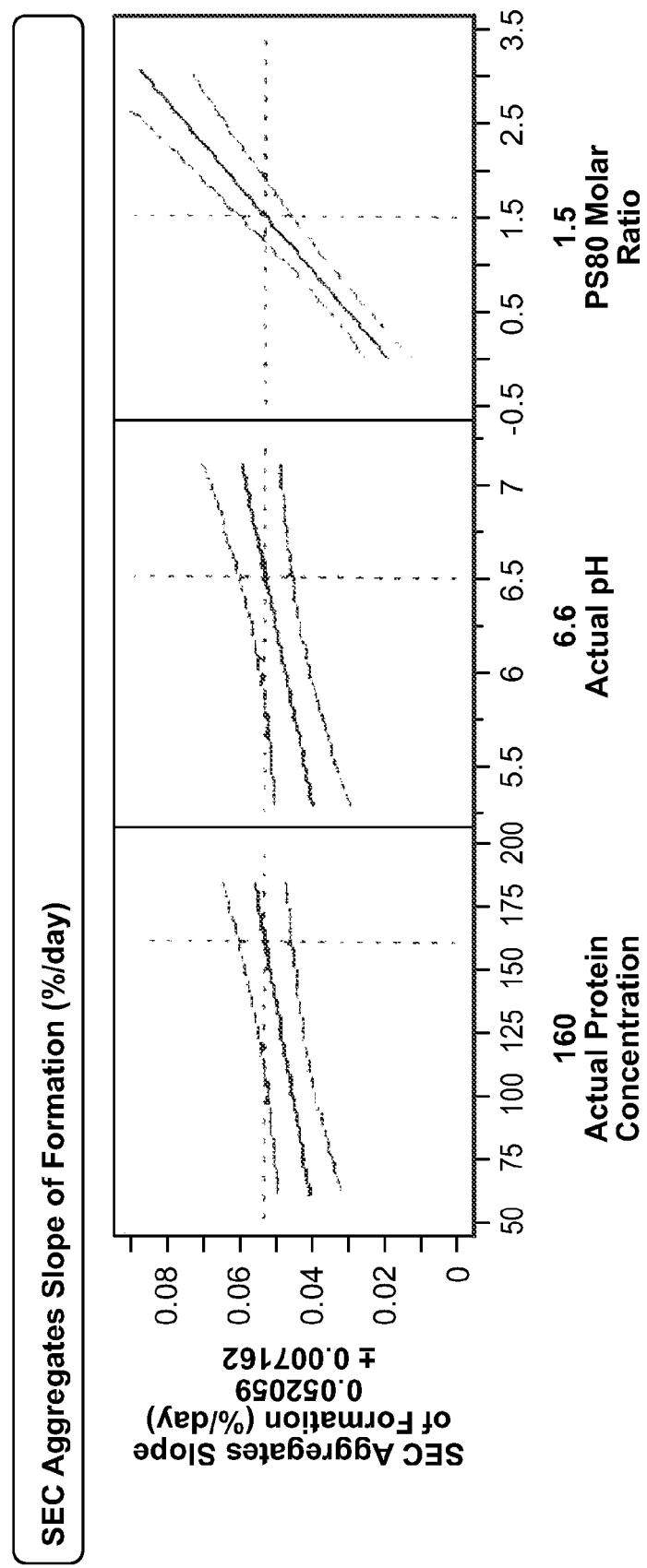
FIG. 6 shows the SEC aggregates slope of formation (% per day) as a result of changes to protein concentration, pH and surfactant:protein molar ratio. At a pH range of 6.0 to 6.5, the formation of aggregates was similar for formulation with the polysorbate 80:protein molar ratio range of 0.7 to 1.5.

The formation of aggregates in the antibody formulation was tested. An SEC aggregates model was developed from experimental data that examined protein concentration, pH, and surfactant:protein molar ratio. At a pH range from 6.0 to 6.5, the formation of aggregates was similar with the polysorbate 80 to protein molar ratio range from 0.7 to 1.5. (FIG. 6) Generally, at PS80:Protein ratios greater than 1.5, the aggregates formation rate increases with increasing pH. (FIG. 7) An experiment examining the formation of SEC aggregates in the presence of air was performed. Eleven different formulations of varying composition were put into borosilicate vials and capped with elastomeric stoppers with an air headspace. An identical set of formulations were created, and the air headspace was displaced with argon. These samples were placed on stability at 40° C. for two weeks. All the samples with the air headspace resulted in large amounts of aggregates at the end of the experiment in comparison to the same formulation with the argon headspace.

TABLE 3

| Sample | Protein Conc. (mg/ml) | Sucrose (%) | Histidine (mM) | Arginine (mM) | PS 80 (%) | pH | Aggregates Air Samples (%) | Aggregates Argon Samples (%) |
|---|---|---|---|---|---|---|---|---|
| 1 | 60 | 2 | 25 | 75 | 0.05 | 6.2 | 0.64 | 0.48 |
| 2 | 60 | 4 | 25 | 75 | 0.05 | 7 | 0.62 | 0.42 |
| 3 | 160 | 4 | 50 | 75 | 0.14 | 6.2 | 0.92 | 0.73 |
| 4 | 160 | 2 | 50 | 75 | 0.14 | 7 | 1.16 | 0.74 |
| 5 | 60 | 2 | 50 | 125 | 0.05 | 7 | 1.28 | 0.33 |
| 6 | 60 | 4 | 50 | 125 | 0.05 | 6.6 | 0.48 | 0.36 |
| 7 | 160 | 4 | 25 | 125 | 0.14 | 7 | 1.04 | 0.70 |
| 8 | 160 | 2 | 25 | 125 | 0.14 | 6.2 | 1.06 | 0.75 |
| 9 | 160 | 3 | 25 | 75 | 0.14 | 6.6 | 1.09 | 0.78 |
| 10 | 110 | 3 | 50 | 125 | 0.10 | 6.2 | 0.65 | 0.47 |
| 11 | 110 | 2 | 25 | 75 | 0.10 | 6.6 | 0.90 | 0.62 |

Based on these experiments, SEC aggregates were hypothesized to form by oxidation or by disulfide bond formation. The addition of antioxidants and/or chelators was explored. A formulation containing 40 mM Histidine, 90 mM Arginine, and 160 mg/mL protein with a polysorbate 80 to protein molar ratio of 1.5 at pH 6.6 was made. To the formulation, 25 mM citrate, 5 mM citrate, 5 mM EDTA, 25 mM cysteine, or 5 mM cysteine was added. All 3 additional excipients reduced the formation of aggregates (FIG. 8). The addition of the antioxidants and/or chelators were ranked in order of performance as citrate>EDTA>cysteine. Either 5 or 25 mM citrate reduced the formation of SEC aggregates as compared to the control formulation.

An experiment was performed to determine the effects of pH, protein concentration, citrate concentration, histidine concentration and the polysorbate 80 to protein molar ratio. The pH was varied from 6.0 to 6.3, the protein concentration was varied from 60 to 160 mg/mL, the citrate concentration was varied from 0 to 25 mM, the histidine concentration was varied from 25 to 50 mM, and the polysorbate 80 to protein molar ratio was varied from 0.7 to 1.5. Formulations were filled in 1 ml long, 27 G½" syringes (0.55+/−0.2 mg silicone). All formulations contained approximately 125 mM arginine.

Stability was tested at 40° C. for two weeks, using CEX and SEC. The results (FIG. 9 and Table 4) show a reduction in aggregate formation with the presence of 25 mM citrate in the formulation, while increasing the protein concentration increased the rate of aggregate formation. The amount of monomer shows opposite trends to the aggregate formation at 25° C. and 40° C., while at 5° C. the amount of monomer is essentially unchanged for up to 24 months (Table 5).

Another set of formulations explored the rate of formation of SEC aggregates in the presence of 40-63 mM citrate but with no histidine at 40° C., 25° C., 5° C. The rate of aggregate formation in these formulations was slightly higher than formulations with histidine at 40° C. However, at 5° C., the rate of formation of aggregates in the formulations with citrate and no histidine were comparable to the formulations containing citrate and histidine (Table 6). Also at 5° C., the amount of monomer is essentially unchanged for up to 24 months (Table 7).

TABLE 4

| Formulation # | Protein Conc. (mg/mL) | pH | Histidine Conc. (mM) | Citrate Conc. (mM) | Arginine Conc. (mM) | PS80: Protein Molar Ratio | Initial Amount of Aggregates (%) | Change in Aggregates After 12 Months at 5° C. | Change in Aggregates After 24 Months at 5° C. | Change in Aggregates After 12 Months at 25° C. | Change in Aggregates After 1 Month at 40° C. |
|---|---|---|---|---|---|---|---|---|---|---|---|
| 1 | 62 | 6.4 | 50 | 25 | 125 | 0.7 | 0.4 | 0.1 | 0.1 | 0.7 | 0.2 |
| 2 | 60 | 6.4 | 50 | 0 | 125 | 1.5 | 0.4 | 0.5 | 1.1 | 1.5 | 0.4 |
| 3 | 157 | 6.4 | 50 | 25 | 125 | 1.5 | 0.4 | 0.2 | 0.3 | 1.3 | 0.5 |
| 4 | 161 | 6.3 | 50 | 0 | 125 | 0.7 | 0.4 | 0.6 | 0.7 | 2.5 | 0.8 |
| 5 | 60 | 6.2 | 50 | 25 | 125 | 1.5 | 0.4 | 0.2 | 0.2 | 0.5 | 0.2 |
| 6 | 110 | 6.0 | 50 | 0 | 125 | 0.7 | 0.4 | 0.4 | 0.6 | 1.7 | 0.7 |
| 7 | 162 | 6.2 | 50 | 25 | 125 | 0.7 | 0.4 | 0.3 | 0.3 | 1.1 | 0.5 |
| 8 | 160 | 6.0 | 50 | 0 | 125 | 1.5 | 0.4 | 0.4 | 0.6 | 2.2 | 0.9 |
| 9 | 169 | 6.3 | 25 | 25 | 125 | 0.7 | 0.5 | — | 0.3 | — | 0.6 |
| 10 | 158 | 6.3 | 25 | 25 | 123 | 1.0 | 0.5 | — | — | — | 0.6 |

TABLE 5

| Formulation # | Protein Conc. (mg/mL) | pH | Histidine Conc. (mM) | Citrate Conc. (mM) | Arginine Conc. (mM) | PS80: Protein Molar Ratio | Initial Amount of Monomer (%) | Change in Monomer After 12 Months at 5° C. | Change in Monomer After 24 Months at 5° C. | Change in Monomer After 12 Months at 25° C. | Change in Monomer After 1 Month at 40° C. |
|---|---|---|---|---|---|---|---|---|---|---|---|
| 1 | 62 | 6.4 | 50 | 25 | 125 | 0.7 | 98.3 | 0.4 | 0.1 | −2.5 | −1.3 |
| 2 | 60 | 6.4 | 50 | 0 | 125 | 1.5 | 98.3 | −0.2 | −1.0 | −3.9 | −2.0 |
| 3 | 157 | 6.4 | 50 | 25 | 125 | 1.5 | 98.2 | 0.2 | 0.0 | −3.1 | −1.6 |

TABLE 5-continued

| Formulation # | Protein Conc. (mg/mL) | pH | Histidine Conc. (mM) | Citrate Conc. (mM) | Arginine Conc. (mM) | PS80: Protein Molar Ratio | Initial Amount of Monomer (%) | Change in Monomer After 12 Months at 5° C. | Change in Monomer After 24 Months at 5° C. | Change in Monomer After 12 Months at 25° C. | Change in Monomer After 1 Month at 40° C. |
|---|---|---|---|---|---|---|---|---|---|---|---|
| 4 | 161 | 6.3 | 50 | 0 | 125 | 0.7 | 98.2 | 0.0 | −0.4 | −4.5 | −2.1 |
| 5 | 60 | 6.2 | 50 | 25 | 125 | 1.5 | 98.3 | 0.3 | 0.2 | −2.2 | −1.4 |
| 6 | 110 | 6.0 | 50 | 0 | 125 | 0.7 | 98.3 | 0.1 | −0.3 | −3.6 | −2.1 |
| 7 | 162 | 6.2 | 50 | 25 | 125 | 0.7 | 98.3 | 0.2 | −0.1 | −2.8 | −1.7 |
| 8 | 160 | 6.0 | 50 | 0 | 125 | 1.5 | 98.3 | −0.1 | −0.4 | −4.2 | −2.3 |
| 9 | 169 | 6.3 | 25 | 25 | 125 | 0.7 | 98.2 | — | −0.1 | — | −1.8 |
| 10 | 158 | 6.3 | 25 | 25 | 123 | 1.0 | 98.1 | — | — | — | −1.7 |

TABLE 6

| Formulation # | Protein Conc. (mg/mL) | pH | Histidine Conc. (mM) | Citrate Conc. (mM) | Arginine Conc. (mM) | PS80: Protein Molar Ratio | Initial Amount of Aggregates (%) | Change in Aggregates After 12 Months at 5° C. | Change in Aggregates After 24 Months at 5° C. | Change in Aggregates After 12 Months at 25° C. | Change in Aggregates After 1 Month at 40° C. |
|---|---|---|---|---|---|---|---|---|---|---|---|
| 11 | 160 | 6.3 | 0 | 40 | 125 | 0.7 | 0.5 | — | 0.4 | — | 0.9 |
| 12 | 165 | 6.3 | 0 | 40 | 125 | 1.5 | 0.6 | 0.3 | — | — | 0.9 |
| 13 | 62 | 6.2 | 0 | 40 | 125 | 1.5 | 0.5 | — | — | 1.7 | 0.4 |
| 14 | 170 | 6.1 | 0 | 40 | 125 | 1.5 | 0.5 | — | — | — | 0.9 |
| 15 | 165 | 6.5 | 0 | 63 | 125 | 1.5 | 0.5 | — | — | — | 1.0 |
| 16 | 160 | 6.3 | 0 | 40 | 125 | 1.0 | 0.6 | 0.3 | — | — | 0.9 |

TABLE 7

| Formulation # | Protein Conc. (mg/mL) | pH | Histidine Conc. (mM) | Citrate Conc. (mM) | Arginine Conc. (mM) | PS80: Protein Molar Ratio | Initial Amount of Monomer (%) | Change in Monomer After 12 Months at 5° C. | Change in Monomer After 24 Months at 5° C. | Change in Monomer After 12 Months at 25° C. | Change in Monomer After 1 Month at 40° C. |
|---|---|---|---|---|---|---|---|---|---|---|---|
| 11 | 160 | 6.3 | 0 | 40 | 125 | 0.7 | 98.3 | — | −0.3 | — | −2.2 |
| 12 | 165 | 6.3 | 0 | 40 | 125 | 1.5 | 98.2 | 0.1 | — | −3.4 | −2.1 |
| 13 | 62 | 6.2 | 0 | 40 | 125 | 1.5 | 98.1 | — | — | — | −1.4 |
| 14 | 170 | 6.1 | 0 | 40 | 125 | 1.5 | 98.1 | — | — | — | −2.0 |
| 15 | 165 | 6.5 | 0 | 63 | 125 | 1.5 | 98.2 | — | — | — | −2.3 |
| 16 | 160 | 6.3 | 0 | 40 | 125 | 1.0 | 98.2 | 0.1 | — | — | −2.0 | pH

Several pH experiments were done to determine the effects of pH on CEX degradation at 5° C. The vedolizumab antibody formulation comprised 160 mg/ml of anti-α4β7 antibody, 125 mM arginine, 50 mM histidine, and 25 mM citrate. Several different pH levels, 6.3, 6.5, 6.7 and 6.9 were tested for stability at 40° C., 25° C., and 5° C.

Figure 10:
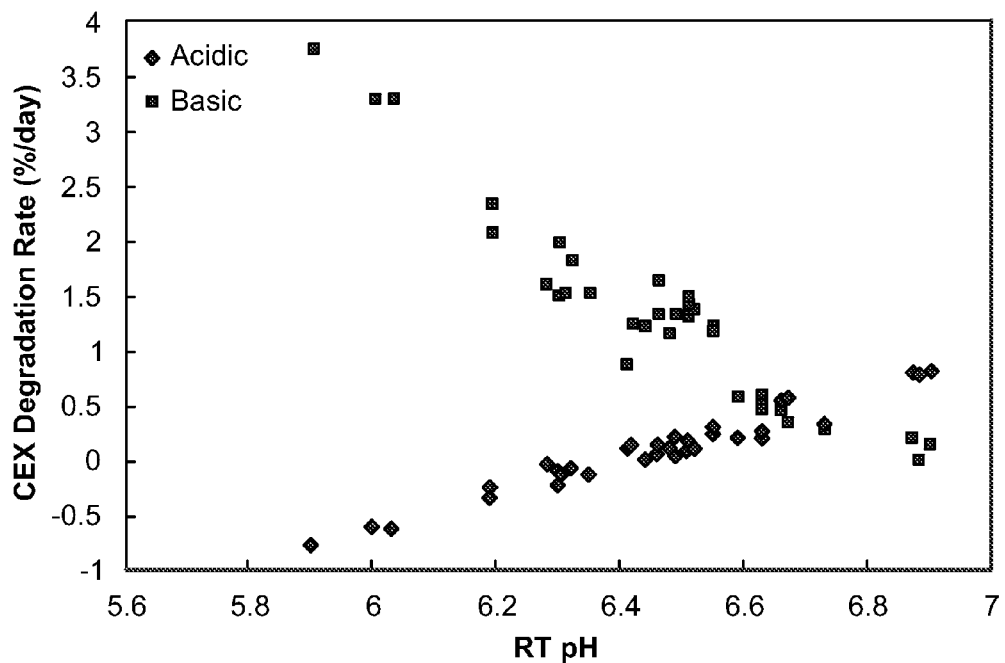
FIG. 10 is a graph showing the results of the CEX species degradation at 40° C. The data shows the influence of pH change on CEX degradation.
Figure 11:
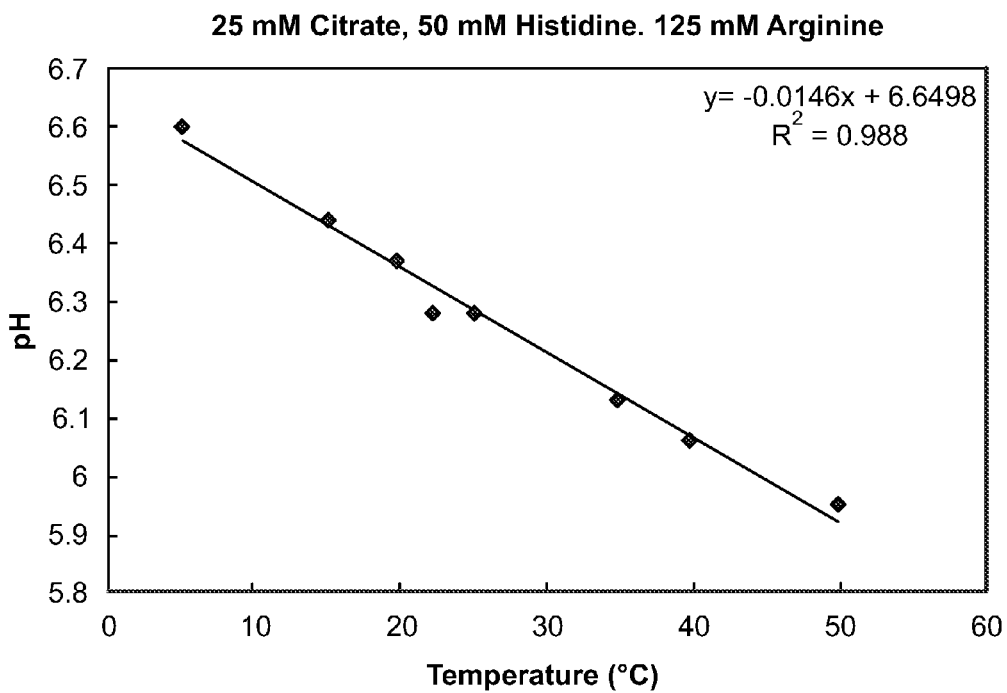
FIG. 11 is a graph showing the effect of temperature on the pH of formulations. The pH of formulations containing histidine decrease with temperature, whereas the pH of citrate formulations is not affected by temperature.

The CEX models at 40° C. show (FIG. 10) that pH influences CEX degradation the most. The pH of formulations containing histidine decrease with increasing temperature, however the pH of citrate formulations was shown to not be affected by temperature (FIG. 11). The histidine/citrate formulation was determined to have good stability at a pH of 6.8 at 40° C. after 1 week, 6.3-6.5 at 25° C. after 6 months and 6.3-6.5 at 5° C. after 6 months. Based on additional studies, the stability of the formulations were similar at 25° C. and 5° C. for the pH range of 6.2 to 6.9 (Tables 8 and 9).

TABLE 8

| | | | | | | | | | Difference in % Relative Area Over Time at 25° C. | | | | | |
|---|---|---|---|---|---|---|---|---|---|---|---|---|---|---|
| Protein Conc. (mg/mL) | pH | Histidine Conc. (mM) | Citrate Conc. (mM) | Arginine Conc. (mM) | PS80: Protein Molar Ratio | Initial Amount of Acidic Species (%) | Initial Amount of Basic Species (%) | Initial Amount of Major Isoform (%) | Change in CEX Acidic After 6 Months | Change in CEX Acidic After 12 Months | Change in CEX Basic After 6 Months | Change in CEX Basic After 12 Months | Change in CEX Major After 6 Months | Change in CEX Major After 12 Months |
| 157 | 6.4 | 50 | 25 | 125 | 1.5 | 23.9 | 6.8 | 69.3 | 8.5 | 17.4 | 7.1 | 3.4 | −15.6 | −20.8 |
| 162 | 6.2 | 50 | 25 | 125 | 0.7 | 24.0 | 6.9 | 69.1 | 4.4 | 12.8 | 10.8 | 8.6 | −15.2 | −21.4 |
| 158 | 6.3 | 50 | 25 | 125 | 1.5 | 24.8 | 5.5 | 69.7 | 7.2 | — | 4.9 | — | −14.4 | — |
| 160 | 6.4 | 42 | 25 | 125 | 1.5 | 24.9 | 5.5 | 69.7 | 9.5 | — | 1.0 | — | −14.4 | — |
| 147 | 6.7 | 45 | 25 | 125 | 2.1 | 24.9 | 4.7 | 70.4 | 14.8 | — | 3.6 | — | −16.5 | — |
| 147 | 6.9 | 45 | 25 | 125 | 2.2 | 25.0 | 4.9 | 70.1 | 14.5 | — | 3.2 | — | −17.9 | — |

TABLE 8-continued

| | | | | | | | | Difference in % Relative Area Over Time at 25° C. | | | | | |
|---|---|---|---|---|---|---|---|---|---|---|---|---|---|
| Protein Conc. (mg/mL) | pH | Histidine Conc. (mM) | Citrate Conc. (mM) | Arginine Conc. (mM) | PS80: Protein Molar Ratio | Initial Amount of Acidic Species (%) | Initial Amount of Basic Species (%) | Initial Amount of Major Isoform (%) | Change in CEX Acidic After 6 Months | Change in CEX Acidic After 12 Months | Change in CEX Basic After 6 Months | Change in CEX Basic After 12 Months | Change in CEX Major After 6 Months | Change in CEX Major After 12 Months |
| 153 | 6.7 | 46 | 25 | 125 | 1.5 | 24.8 | 5.5 | 69.7 | 14.7 | — | 0.3 | — | -17.3 | — |
| 154 | 6.9 | 46 | 25 | 125 | 1.5 | 24.9 | 5.3 | 69.8 | 19.7 | — | 0.5 | — | -20.2 | — |
| 170 | 6.5 | 50 | 25 | 125 | 1.0 | 25.7 | 4.6 | 69.7 | 10.8 | — | 4.4 | — | -15.2 | — |
| 170 | 6.5 | 50 | 25 | 125 | 1.5 | 25.7 | 4.6 | 69.7 | 11.1 | — | 5.2 | — | -16.4 | — |
| 160 | 6.5 | 50 | 25 | 125 | 1.5 | 26.3 | 7.0 | 66.7 | 11.8 | — | -2.6 | — | -11.9 | — |

TABLE 9

| | | | | | Difference in % Relative Area Over Time at 5° C. | | | | | |
|---|---|---|---|---|---|---|---|---|---|---|
| Protein Conc. (mg/mL) | pH | Histidine Conc. (mM) | Citrate Conc. (mM) | Arginine Conc. (mM) | PS80: Protein Molar Ratio | Change in CEX Acidic After 6 Months | Change in CEX Acidic After 24 Months | Change in CEX Basic After 6 Months | Change in CEX Basic After 24 Months | Change in CEX Major After 6 Months | Change in CEX Major After 24 Months |
| 157 | 6.4 | 50 | 25 | 125 | 1.5 | 0.2 | 0.6 | 2.3 | -0.9 | -2.5 | 0.3 |
| 162 | 6.2 | 50 | 25 | 125 | 0.7 | -0.2 | -0.7 | 4.3 | 2.2 | -4.1 | -1.5 |
| 158 | 6.3 | 50 | 25 | 125 | 1.5 | 0.0 | — | 1.9 | — | -1.9 | — |
| 160 | 6.4 | 42 | 25 | 125 | 1.5 | 0.1 | — | 1.7 | — | -1.8 | — |
| 147 | 6.7 | 45 | 25 | 125 | 2.1 | 1.7 | — | 1.7 | — | -3.4 | — |
| 147 | 6.9 | 45 | 25 | 125 | 2.2 | 1.6 | — | 1.1 | — | -2.7 | — |
| 153 | 6.7 | 46 | 25 | 125 | 1.5 | 1.7 | — | 0.4 | — | -2.1 | — |
| 154 | 6.9 | 46 | 25 | 125 | 1.5 | 2.1 | — | 0.4 | — | -2.4 | — |
| 170 | 6.5 | 50 | 25 | 125 | 1.0 | 0.9 | — | 1.6 | — | -2.5 | — |
| 170 | 6.5 | 50 | 25 | 125 | 1.5 | 0.8 | — | 1.6 | — | -2.5 | — |
| 160 | 6.5 | 50 | 25 | 125 | 1.5 | 11.8 | — | -2.6 | — | -11.9 | — |

Example 2

Stability

Figure 12:
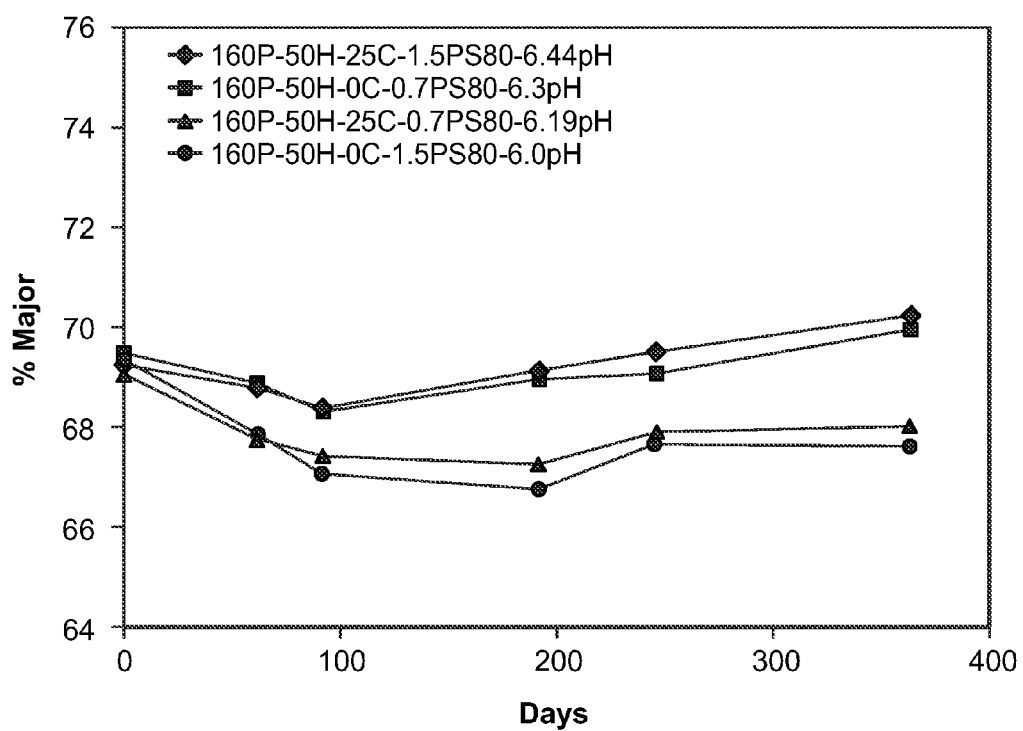
FIG. 12 is a graph showing the percentage of CEX major isoform over a period of twelve months. Formulations having a pH of 6.0-6.2 showed about 1-2% fewer major isoform than formulations having a pH of 6.3-6.4.

Four different anti-α4β7 antibody formulations were tested for stability over the course of twelve months. Formulations having a pH of 6.0-6.2 showed approximately 1-2% less major species than formulations having a pH of 6.3-6.4 (FIG. 12). Formulations having a pH of 6.3-6.4 showed less than 1% change in basic or major species at 5° C.

Ten different anti-α4β7 antibody formulations were tested for stability by SEC over the course of twelve months (Table 10). The formulations with 60 mg/mL protein concentration and containing 25 mM citrate had a change in aggregates of 0.1-0.2% after 1 year, while formulations containing 160 mg/mL protein and 25 mM citrate had an increase of aggregates from 0.2-0.3% over 1 year. There was an increase of 0.4-0.6% aggregates for formulations containing 60, 110, or 160 mg/mL protein with no citrate.

TABLE 10

| Formulation # | Protein Concentration (mg/mL) | pH | Histidine Concentration (mM) | Citrate Concentration (mM) | Arginine Concentration (mM) | PS80 Molar Ratio | Change in % Aggregates at 5° C. After 1 Year |
|---|---|---|---|---|---|---|---|
| 1 | 62 | 6.41 | 50 | 25 | 125 | 0.7 | 0.11 |
| 2 | 60 | 6.35 | 50 | 0 | 125 | 1.5 | 0.50 |
| 3 | 157 | 6.44 | 50 | 25 | 125 | 1.5 | 0.23 |
| 4 | 161 | 6.3 | 50 | 0 | 125 | 0.7 | 0.56 |
| 5 | 60 | 6.19 | 50 | 25 | 125 | 1.5 | 0.16 |
| 6 | 110 | 6.03 | 50 | 0 | 125 | 0.7 | 0.39 |
| 7 | 162 | 6.19 | 50 | 25 | 125 | 0.7 | 0.26 |
| 8 | 160 | 6 | 50 | 0 | 125 | 1.5 | 0.44 |
| 9 | 165 | 6.28 | 0 | 40 | 125 | 1.5 | 0.30 |
| 10 | 160 | 6.3 | 0 | 40 | 125 | 1.0 | 0.33 |

Example 3

Viscosity

Figure 13:
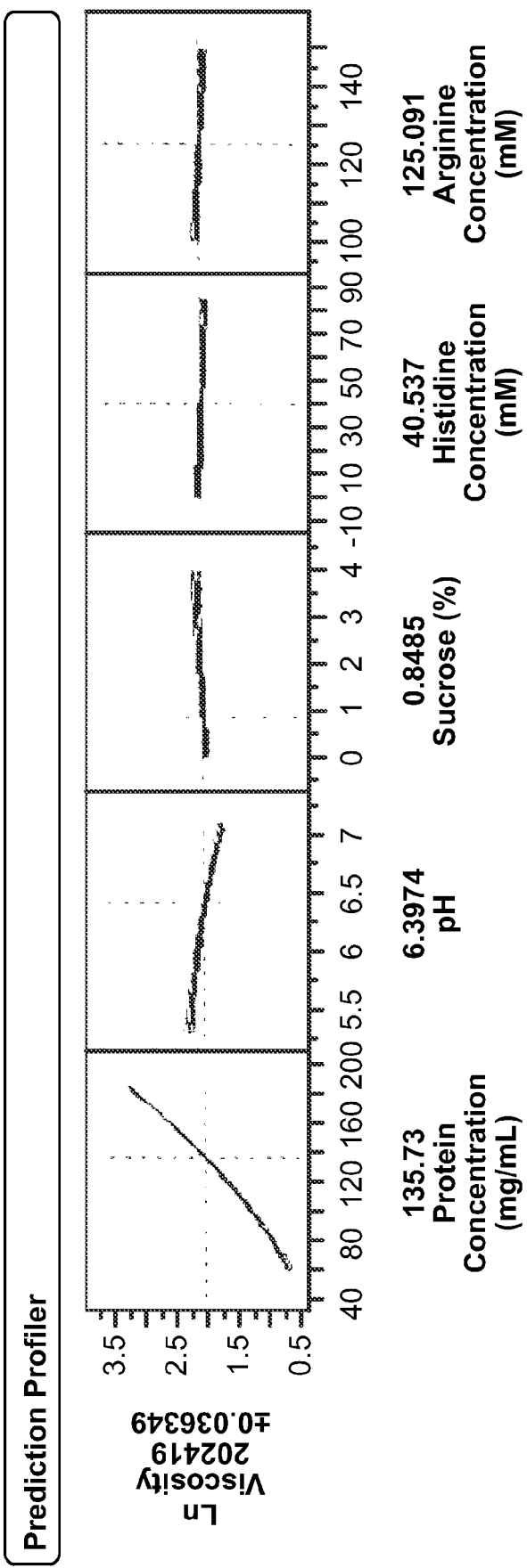
FIG. 13 shows a set of graphs that demonstrate that viscosity is affected mainly by protein concentration and pH. Sucrose, histidine and arginine additions are shown to have a minor affect on the viscosity of the formulation.

The injection force needed to administer the pharmaceutical formulation is related to the viscosity of the formulation. Formulations with varying pH and varying concentrations of protein, arginine, histidine, citrate, sucrose, and polysorbate 80 were made. The viscosity of these formulations was tested. A statistical model of the Ln (viscosity) was developed. The model showed that the viscosity is affected mainly by protein concentration and pH (FIG. 13). Sucrose, histidine and arginine also can have a minor effect on viscosity. In some protein formulations, sodium chloride is added to reduce the viscosity of the formulation. It is known, however, that the effect of sodium chloride on viscosity is protein and formulation dependent.

Sodium chloride was added to a formulation containing 140 mg/ml vedolizumab, 125 mM arginine, 25 mM histidine, 25 mM citrate, and polysorbate 80 at a 1.5 polysorbate 80 to protein molar ratio, and a pH of 6.4. The NaCl did not have any effect on the viscosity of the formulation.

Figure 16A:
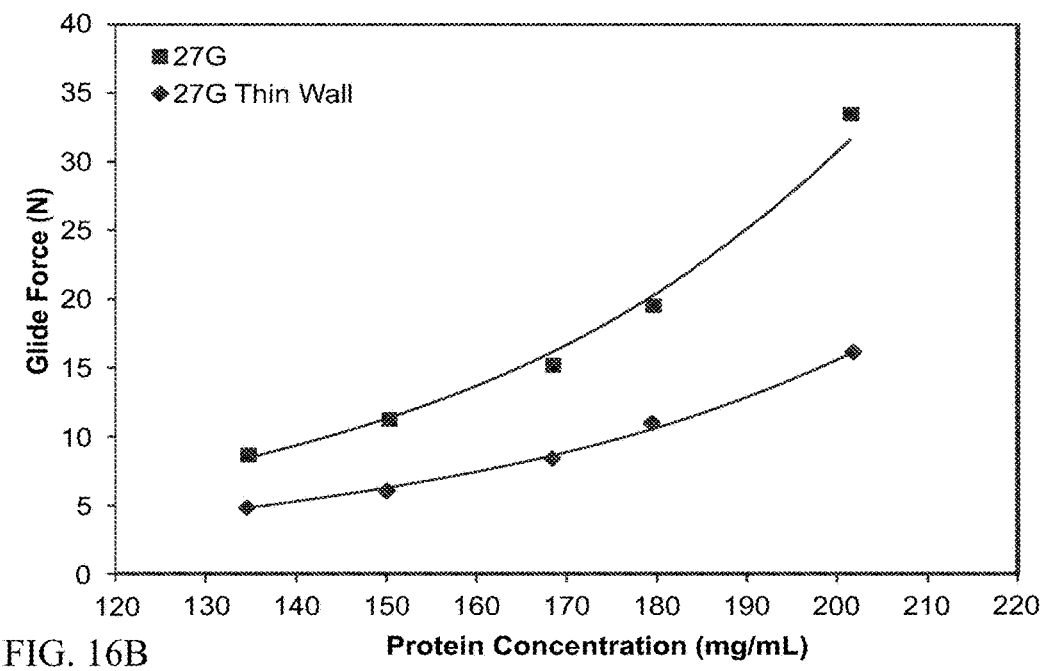
FIGS. 16A-B show the effect of (A) protein concentration and (B) viscosity on the injection force of various syringes tested.
Figure 16B:
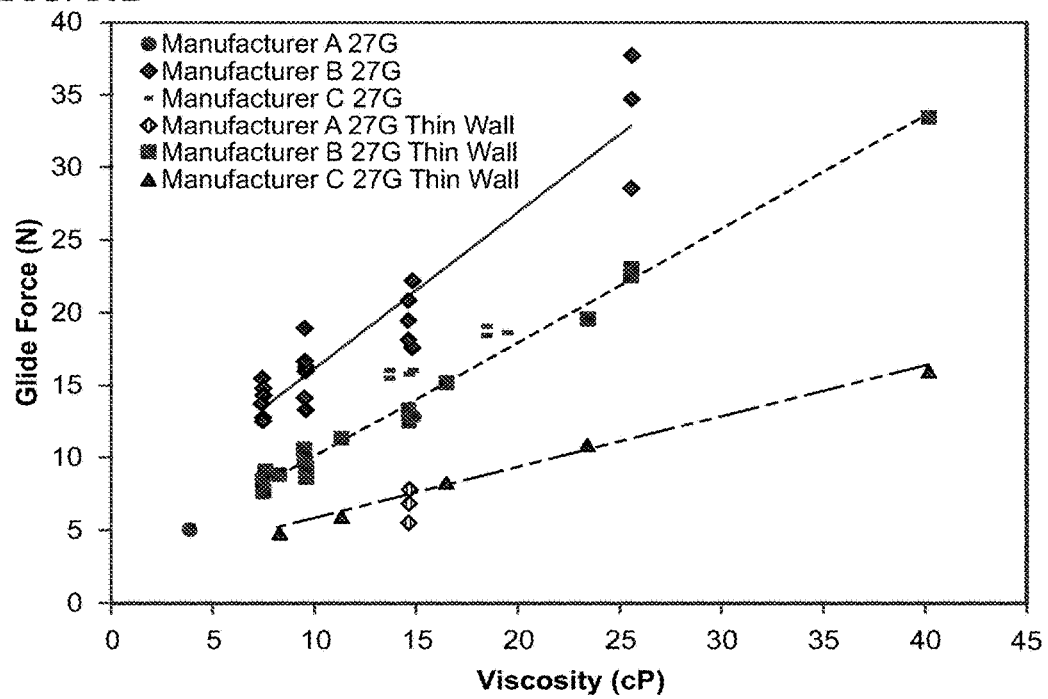

The effects of the viscosity on the injection force of various syringes tested are shown in FIGS. 16A and 16B.

Example 4

Methods

Cation Exchange Chromatography (CEX)

A phosphate/sodium chloride gradient on a weak cation exchange column is used in a high performance liquid chromatography system to separate charged species in anti-α4β7 antibody formulations and determine the charge composition of the antibody species. Acidic Isoforms elute before the Major Isoform and Basic Isoforms elute after the Major Isoform.

Stability data for a vedolizumab formulation generated using a CEX assay indicated that the % Major Isoform was above 55.0%.

Capillary Isoelectric Focusing (cIEF)

cIEF is performed using an iCE280 whole column detection cIEF system (Convergent Biosciences, Toronto, Ontario). Choice of ampholyte can be as recommended by the manufacturer or can be a combination of commercially available ampholytes. A useful combination is a mixture of 3-10 and 5-8 PHARMALYTE™ (GE Healthcare, Piscataway, N.J.).

Stability data for a vedolizumab formulation generated using a cIEF assay indicated that the % Major Isoform was about 53%, the % Acidic Species was about 42% and the % Basic Species was about 5%.

Size Exclusion Chromatography (SEC)

SEC is performed using an analytical SEC column (Tosoh Bioscience, LLC, King of Prussia, Pa.). The mobile phase is a phosphate-buffered saline solution and the absorbance is monitored at 280 nm.

Stability data for a vedolizumab formulation generated using an SEC assay indicated that the % Monomer was 99.0%, the % Aggregates was <0.5% and the % Low Molecular Weight substances was <1.0%.

SDS-PAGE Assay

SDS-PAGE is performed using an Invitrogen (Carlsbad, Calif.) Tris-Glycine gel, 4-20% for reducing condition and 4-12% for non-reducing condition. The reconstituted antibody formulation sample is diluted in liquid formulation buffer then diluted one to two with Tris-Glycine SDS Sample Buffer (2×, Invitrogen) either with 10% 2-mercaptoethanol (reducing sample buffer) or without 2-mercaptoethanol (non-reducing sample buffer). Samples are briefly heated and loaded in comparison with a molecular weight marker (Invitrogen). The gels are stained with colloidal coomassie blue (Invitrogen) according to the manufacturer's instruction. Protein bands are analyzed by densitometry to identify the % heavy and light chain for reduced gels and % IgG for non-reduced gels.

Binding Efficacy

HuT78 cells (human T cell lymphoma cells, American Type Culture Collection, Manassas, Va.) suspended in 1% BSA in PBS, 0.01% sodium azide are contacted with serial dilutions of primary test antibody. After incubation on ice, the cells are washed and treated with fluorescently labeled secondary antibody. After a further wash, the cells are fixed and suspended in FACS reagent for analysis by flow cytometry (Becton Dickinson Franklin Lakes, N.J.); also see U.S. Pat. No. 7,147,851.

Moisture by Karl Fischer

The formulation is titrated with methanol for a coulometric Karl Fischer moisture determination.

Example 5

Effects of Silicone from Syringe Products Pre-Filled with Anti-α4β7 Antibody Formulation A subcutaneous formulation consisting of 60-160 mg/mL of anti-α4β7 protein in a buffer containing L-Histidine, L-Arginine Hydrochloride, Citrate and Polysorbate 80 is used to study the effects of silicone on the stability of the protein formulations and container/closure attributes. The study is performed with a 0.5 mL fill.

Parameters including the protein concentration, the polysorbate 80 to protein molar ratio, and the amount of silicone that is sprayed onto the syringe barrels are explored. The range of each of the input parameters is shown in Table 11.

TABLE 11

Input Parameter Ranges

| Parameters | Low | High |
| --- | --- | --- |
| Protein Concentration (mg/mL) | 100 | 160 |
| Polysorbate 80:Protein Ratio | 0 | 2 |
| Silicone Amount (mg) | 0.4 | 0.8 |

A design of experiment is used to determine the set of formulations to study. A reasonable number of formulations range from 6 to 8 formulations. An example of the formulations that are tested is shown in Table 12.

TABLE 12

| Run | Protein Conc. (mg/mL) | PS80:Protein Ratio | PS80 Concentration (%) | Silicone Level (mg) |
| --- | --- | --- | --- | --- |
| 1 | 100 | 1 | 0.087 | 0.8 |
| 2 | 100 | 2 | 0.174 | 0.8 |
| 3 | 160 | 0 | 0 | 0.8 |
| 4 | 160 | 2 | 0.279 | 0.4 |
| 5 | 100 | 0 | 0 | 0.4 |
| 6 | 160 | 2 | 0.279 | 0.8 |
| 7 | 100 | 1 | 0.087 | 0.4 |
| 8 | 160 | 0 | 0 | 0.4 |
| 9 | 100 | 0 | 0 | 0 |

TABLE 12-continued

| Run | Protein Conc. (mg/mL) | PS80:Protein Ratio | PS80 Concentration (%) | Silicone Level (mg) |
|---|---|---|---|---|
| 10 | 100 | 2 | 0.174 | 0 |
| 11 | 160 | 0 | 0 | 0 |
| 12 | 160 | 2 | 0.279 | 0 |

Some controls may be added to the set of formulations and tested at a few select time points.

These formulations are placed on stability at several different temperatures (e.g., 5° C., 25° C./60% RH, 40° C./75% RH) and pulled at various time points (e.g., 0 week, 1 week, 2 weeks, 4 weeks, 8 weeks, 12 weeks, 6 months, and 12 months) for testing. Controls are tested at 0 weeks, 12 weeks, 6 months and 12 months.

The tests that are performed at each stability time pull include SEC, CEX, Instron, MFI, and Silicone Quantification. 1 syringe is tested for Instron, with the expelled material being used for SEC, CEX, injection force measurements and microflow imaging (MFI), and silicone quantification.

Example 6

Analysis of Pre-Filled Syringe Components Filled with Anti-α4β7 Antibody Formulation This study explored how various syringe manufacturers, plunger (stopper) elastomeric materials, and the amount of PS80 in the formulation affected the mechanical properties of the system and the stability of the formulation.

A design of experiment was created exploring 3 different syringe manufacturers, 2 different plunger (stopper) material types, and 2 different PS80 to protein molar ratios. The rest of the formulation was kept constant at 170 mg/mL of protein, 125 mM arginine, 50 mM histidine, 25 mM citrate, and a pH of 6.5. The needle size on these pre-filled syringes was 27 G ¼' or 29 G ½" thin wall. The experiments performed are detailed in Table 15.

The experimental design inputs for the active portion of the experiment are shown below in Table 13, while the constants are shown in Table 14. The experimental design was created utilizing the inputs shown in Table 13.
The list of experiments is shown in Table 10.

TABLE 13

DOE variables and levels with active formulation

| Variable | Values | | |
|---|---|---|---|
| PS80:Protein Molar Ratio | 1.0 | | 1.5 |
| Syringe Manufacturer | A | B | C |
| Plunger (Stopper) Type | 4432 | | 4023 Coated |

TABLE 14

Constants for active formulation

| Constant | Value |
|---|---|
| Protein Concentration (mg/mL) | 170 |
| Arginine Concentration (mM) | 125 |
| Histidine Concentration (mM) | 50 |

TABLE 14-continued

Constants for active formulation

| Constant | Value |
|---|---|
| Citrate Concentration (mM) | 25 |
| pH | 6.5 |

TABLE 15

Experimental details

| Run # | Syringe Type | Plunger (Stopper) | PS80 |
|---|---|---|---|
| 1 | C | 4432 | 1 |
| 2 | B | 4432 | 1 |
| 3 | A | 4023 | 1 |
| 4 | C | 4023 | 1 |
| 5 | B | 4023 | 1 |
| 6 | A | 4023 | 1.5 |
| 7 | C | 4023 | 1.5 |
| 8 | B | 4023 | 1.5 |

A concentrated formulation anti-α4β7 formulation is spiked with polysorbate 80 and diluted down to 170 mg/mL. The composition of the starting formulation is shown below in Table 16.

TABLE 16

Starting Formulation buffer details

| Protein (mg/ml) | Total His (mM) | Total Citrate (mM) | Arg (mM) | pH |
|---|---|---|---|---|
| 183 | 50 | 25 | 125 | 6.48 |

For the dilution of the material to the desired formulation composition, stock solutions of PS80 in 25 mM Citrate, 50 mM Histidine, 125 mM Arginine, pH 6.48 are made.

TABLE 17

Stock solution details

| Excipient | Concentration |
|---|---|
| PS 80 (%) | 5 |

The dilution scheme for the formulations is detailed in Table 18.

TABLE 18

Dilution detail

| Starting Formulation (uL) | PS80 in His/Arg/Citrate Buffer (uL) | 50 mM Histidine, 125 mM Arginine, 25 mM Citrate pH 6.48 Buffer (uL) | Total Volume (uL) |
|---|---|---|---|
| 27868.9 | 890.8 | 1240.3 | 30000.0 |
| 18579.2 | 890.8 | 530.0 | 20000.0 |

Compounding is performed based on the dilution scheme, and the starting formulation should be weighed, while the other stock solutions can be pipetted volumetrically. Formulations are filtered. 0.5 mL of formulation is aliquotted into as many 1 mL Long syringes as possible. The syringes are stoppered by the stoppering machine with a 2-4 mm bubble. For each time point, there is one syringe stored needle down and one syringe stored sideways. The extra syringes are stored needle down.

The syringes are tested at 5, 25 and 40° C. on week 2 and at one month. Analytical testing (appearance, Instron, pH, osmolality, density, viscosity, SEC, CEX, and Brightwell) is performed initially and then again at 2 weeks at 25 and 40° C. and at 4 weeks at 25° C.

Example 7

Analysis of Subcutaneous Container Closures Used in 27 G Thin Wall Needle Syringes Pre-Filled with Anti-α4β7 Antibody Formulation This study explores how various syringe models with a 27 G thin wall needle and various plunger (stopper) manufacturers and models affect the mechanical properties of the system and the stability of the formulation over time.

This study explores how the stability of the anti-α4β7 subcutaneous liquid formulation in a prefilled syringe and the mechanical properties of the syringe are affected by the syringe manufacturer and the plunger (stopper) model for syringes with a 27GTW needle. The data generated from this study may determine the container/closure components for the liquid subcutaneous anti-α4β7 formulation.

The experimental design inputs are shown below in Table 19, while the constants are shown in Table 20. The experimental design was created utilizing the inputs shown in Table 19.

The list of experiments to be performed is shown in Table 21.

TABLE 19

DOE variables and levels with active formulation

| Variable | Values | | | |
|---|---|---|---|---|
| Syringe Manufacturer | A | B | C | |
| Plunger (Stopper) Type | 4432 | 4023 Coated | D | E |

TABLE 20

Constants for active formulation

| Constant | Value |
|---|---|
| Protein Concentration (mg/mL) | 160 |
| Arginine Concentration (mM) | 125 |
| Histidine Concentration (mM) | 50 |
| Citrate Concentration (mM) | 25 |
| PS80 (%) | 0.2 |
| pH | 6.5 |

TABLE 21

Experimental details

| Run # | Syringe | Plunger (Stopper) |
|---|---|---|
| 1 | B | D |
| 2 | B | 4432 |
| 3 | A | 4432 |
| 4 | B | 4023 Coated |
| 5 | A | D |

TABLE 21-continued

Experimental details

| Run # | Syringe | Plunger (Stopper) |
|---|---|---|
| 6 | C | 4023 Coated |
| 7 | A | 4023 Coated |
| 8 | C | D |
| 9 | C | 4432 |
| 10 | C | E |

A concentrated anti-α4β7 formulation is spiked with polysorbate 80 and diluted down to 160 mg/mL. The composition of the starting formulation is shown below in Table 22.

TABLE 22

Starting Formulation buffer details

| Protein (mg/ml) | Total His (mM) | Total Citrate (mM) | Arg (mM) | pH |
|---|---|---|---|---|
| 180 | 50 | 25 | 125 | 6.3 |

For the dilution of the material to the desired formulation composition, stock solutions of PS80 in 25 mM Citrate, 50 mM Histidine and 125 mM Arginine, pH 6.3 are made.

TABLE 23

Stock solution details

| Excipient | Concentration |
|---|---|
| PS 80 (%) in His/Arg/Citrate buffer pH 6.3 | 1.68 |

The dilution scheme for the formulations is detailed in Table 24.

TABLE 24

Dilution detail

| Starting Formulation in His Arg Citrate buffer (mL) | PS80 in His/Arg/Citrate Buffer (mL) | Total Volume (mL) |
|---|---|---|
| 78 | 10 (1.68%) | 88 |

Compounding is performed based on the dilution scheme, and the starting formulation should be weighed, while the other stock solutions can be pipetted volumetrically. Formulations are filtered. 0.5 mL of formulation is aliquotted into as many 1 mL Long syringes as possible. The syringes are stoppered by the stoppering machine with a 2-4 mm bubble. For each time point, there is one syringe stored needle down (horizontal position).

The syringes are tested at 5° C., 25° C./60% RH, and 40° C./75% RH at 1 month, 3 months, 6 months, 9 months (optional), 12 months, 18 months and 24 months.

The liquid formulations are analytically tested (concentration, osmolality, pH, Instron, MFI, SEC, and/or CEX) at 1, 3, 6, 9, 12, 18, 24 month (5° C.); 1, 3, 6, 9, 12, 18, month (25° C.); 1, 3, 6, 9, 12, month (40° C.); and 1, 3, month (40° C.).

Example 8

Analysis of Subcutaneous Anti-α4β7 Antibody Formulation in Plastic Prefilled Syringes This study is initiated to research the use of plastic syringes as the container/closure system for an anti-α4β7 antibody subcutaneous formulation. The stability of a representative anti-α4β7 antibody subcutaneous formulation in candidate plastic prefilled syringes is studied. The data generated from this study helps to judge the applicability of using a plastic syringe for a liquid subcutaneous anti-α4β7 antibody formulation.

Stability test samples are prepared as shown below. Stability tests are conducted under the storage conditions of 40° C./75% RH, 25° C./60% RH, and 5° C.

Two types of plastic syringes and one glass syringe (Control) in Table 25 are tested with a liquid subcutaneous anti-α4β7 antibody formulation shown in Table 26. Table 27 shows the details of each set of samples to be tested in the experiment.

TABLE 25

Plastic syringes

|  |  | Sample #1 Plastic syringe 1 | Sample #2 Plastic syringe 2 | Sample #3 Glass syringe (Control) |
|---|---|---|---|---|
| Syringe | Vendor | F | B | A |
|  | Components | Syringe: polymer Needle: 27G(TW) Rigid needle shield | Syringe: polymer Needle: 26G(RW) Luer lock tip cap | Syringe: Glass Needle: 27G(TW) Rigid needle shield |
|  | Silicon coating | Free | Not free | Not free |
| Plunger | Vendor | F | F | ← |
|  | Product description | 1 mL material A | 1 mL material B | ← |
|  | Silicon coating | No | Yes | ← |

TABLE 26

Anti-α4β7 antibody subcutaneous formulation (pH 6.5)

| Component | Composition |
|---|---|
| Anti-α4β7 antibody | 160 mg/mL |
| Arginine | 125 mM |
| Histidine | 50 mM |
| Citrate | 25 mM |
| PS80 (Protein Molar Ratio) | 1.5 (0.2 w/v %) |

TABLE 27

Sample details

| Sample # | Plastic syringe vendor | Protein (MW: 150000) (mg/ml) | (mM) | Arg (MW: 174.20) (mM) | His (MW: 155.15) (mM) | Citrate (MW: 210.14) (mM) | PS80 (MW: 1309.68) (w/v %) | Protein Molar Ratio | pH |
|---|---|---|---|---|---|---|---|---|---|
| 1 | F | 160 | 1.067 | 125 | 50 | 25 | 0.21 | 1.5 | 6.5 |
| 2 | B | 160 | 1.067 | 125 | 50 | 25 | 0.21 | 1.5 | 6.5 |
| 3 (Cont.) | A | 160 | 1.067 | 125 | 50 | 25 | 0.21 | 1.5 | 6.5 |

Previously prepared liquid subcutaneous anti-α4β7 formulation are used for this investigation. Formulations are filtered. Sampling the filtered solution for the quality test as "before filling" sample (Appearance, MFI, DLS). 0.5 mL of formulation are aliquotted into 1 mL plastic syringes. The syringes are stoppered by the vacuum stoppering machine. The syringes are stored needle down.

An initial check is performed to measure pH, osmolality, density, viscosity, and protein concentration. Analytical testing (appearance, SEC (Aggregates, Monomer, LMW), CEX (Acidic, Main, Basic), glide force, MFI, DLS, and/or weight) is performed after 1 week, at 40° C., 2 weeks, 40° C., 1 month, 5, 25 and 40° C., 3 months, 5 and 25° C., 6 months at 5 and 25° C., 9 months at 5 and 25° C., and 12 months at 5 and 25° C.

Samples are taken at 1 month, 3 months, 6 months, 9 months and 12 months at 5° C. and 25° C. Samples are taken at 1 week, 2 weeks and 1 month at 40° C.

Example 9

Figure 17A:
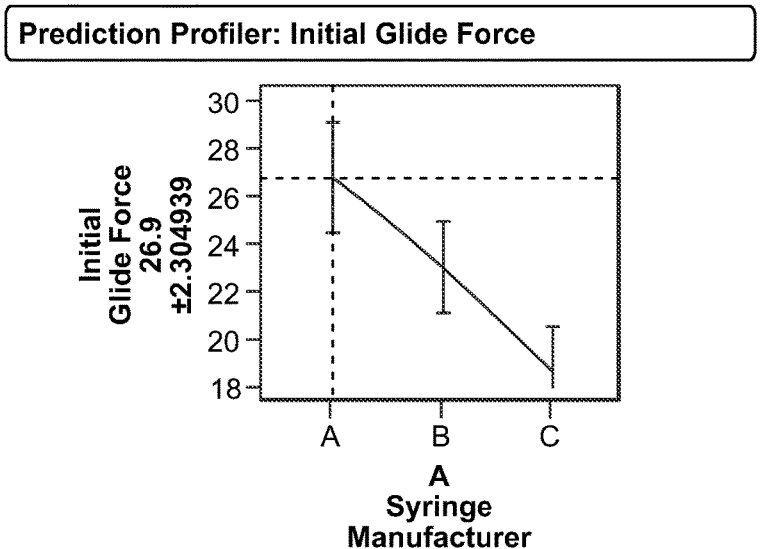
FIG. 17 (A) shows the initial glide force as a function of protein concentration and the needle size.
Figure 17B:
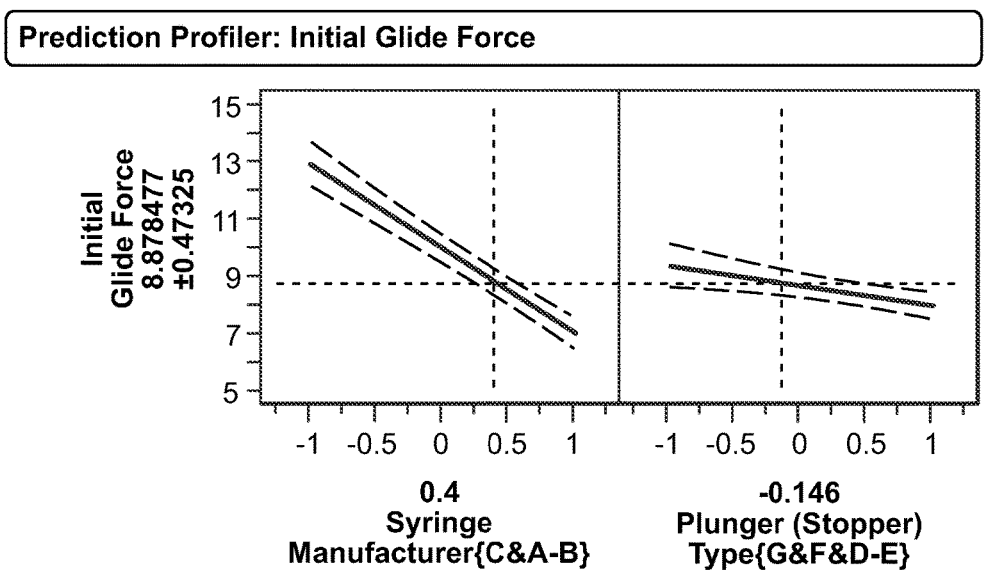

The samples were analyzed for appearance, injection force, SEC, CEX, and micro-flow imaging at 5° C. and 25° C. at various time points that may have included 0, 1, 3, 6, and 12 months. The stability of the formulation as measured by SEC and CEX were similar to what was discussed in Examples 1 and 2. For injection force testing, the glide force were measured (Table 28). A statistical model determined that the only significant factor affecting the glide force was the syringe manufacturer, where A had higher glide forces than B, which was greater than C (FIG. 17). The changes in glide force of the syringes over 12 months at 5° C. and 6 months at 25° C. were less than 10 N, but mostly less than 5 N.

TABLE 28

| Run # | Syringe Manufacturer | Needle Size | Plunger (Stopper) Type | PS80:Protein Molar Ratio | Initial Glide Force (N) |
|---|---|---|---|---|---|
| 1 | C | 27G | D | 1 | 19.2 |
| 2 | B | 27G | D | 1 | 22.9 |
| 3 | A | 29GTW | E | 1 | 25.0 |
| 4 | C | 27G | E | 1 | 18.5 |
| 5 | B | 27G | E | 1 | 22.7 |
| 6 | A | 29GTW | E | 1.5 | 28.8 |
| 7 | C | 27G | E | 1.5 | 18.7 |
| 8 | B | 27G | E | 1.5 | 23.7 |

Example 10

Analysis of Pre-Filled Syringe Components Used in 27 G Thin Wall Needle Syringes Filled with Anti-α4β7 Antibody Formulation This study explored how various syringe manufacturers with a 27 G thin wall needle and various plunger (stopper) manufacturers and elastomeric materials affected the mechanical properties of the pre-filled syringe system and the stability of the formulation over time.

Three different syringe manufacturers and 4 different plunger (stopper) models were tested with 27 G ½" thin wall needles and a formulation containing 160 mg/mL protein, 125 mM arginine, 50 mM histidine, 25 mM citrate, 0.2% PS80, at a pH of 6.5. All of the samples created and tested are shown in Table 29.

TABLE 29

| Experimental details | | |
|---|---|---|
| Run # | Syringe | Plunger (Stopper) |
| 1 | B | F |
| 2 | B | D |
| 3 | A | D |
| 4 | B | E |
| 5 | A | F |
| 6 | C | E |
| 7 | A | E |
| 8 | C | F |
| 9 | C | D |
| 10 | C | G |

The samples were analyzed for appearance, injection force, SEC, CEX, and micro-flow imaging at 5° C., 25° C., and 40° C. at various time points that may have included 0, 1, 3, 6, and 12 months. The stability of the formulation as measured by SEC and CEX were similar to what was discussed in Examples 1 and 2. For injection force testing, the breakloose and glide force were measured. The results at the initial time point are shown in Table 30.

TABLE 30

| Run # | Syringe Manufacturer | Plunger (Stopper) Type | Initial Glide Force (N) | Initial Breakloose Force (N) | Breakloose Force at 12 Months at 5° C. (N) | Breakloose Force at 12 Months at 25° C. (N) | Breakloose Force at 12 Months at 40° C. (N) |
|---|---|---|---|---|---|---|---|
| 1 | B | F | 12.0 | 4.0 | 3.8 | 12.9 | 28.7 |
| 2 | B | D | 11.9 | 3.9 | 4.6 | 12.4 | 36.0 |
| 3 | A | D | 7.0 | 4.0 | 6.5 | 5.1 | 6.4 |
| 4 | B | E | 13.9 | 4.5 | 4.7 | 5.8 | 17.2 |
| 5 | A | F | 5.7 | 4.1 | 3.0 | 17.5 | 23.9 |
| 6 | C | E | 6.7 | 4.1 | 5.0 | 5.8 | 11.4 |
| 7 | A | E | 7.9 | 7.6 | 4.3 | 10.4 | 6.1 |
| 8 | C | F | 6.3 | 4.2 | 4.1 | 15.0 | 33.3 |
| 9 | C | D | 5.9 | 4.8 | 3.9 | 4.4 | 10.0 |
| 10 | C | G | 7.2 | 4.6 | 6.1 | 9.8 | 13.0 |

A statistical model showed that syringe manufacturers A and C were similar and had lower glide forces than manufacturer B, while plunger (stopper) E have slightly higher glide force than the other plunger (stoppers).

Generally, the initial breakloose forces were similar between all the samples that were tested.

Over 12 months at 5° C., 25° C., and 40° C., the glide forces did not signicantly change. However, the breakloose force for syringes with plunger (stopper) F increased by 12 months at 25° C. and 40° C.

Example 11

Analysis of Anti-α4β7 Antibody Formulation in Prefilled Syringes

This study determines how varying levels of protein concentration, polysorbate 80 concentration, citrate concentration, and pH affects anti-α4β7 antibody formulations in a prefilled syringe format.

Part of the experimental design is created in JMP with a fraction factorial of two levels of protein concentration (60 to 160 mg/mL), pH (6.0 to 6.3), polysorbate 80:protein molar ratio (0.723 to 1.5), and citrate concentration (0 to 25 mM). These formulations have a constant value of Histidine concentration (50 mM) and Arginine (125 mM) (Formulations 1-8). Variations of these formulations with 25 mM Histidine are added (Formulations 9-10).

An additional set of formulations are developed to explore formulations with no histidine present and only citrate acting as the buffer (Formulations 11-16). The levels of the inputs for all formulations being explored are shown in Table 31. The constants used for all formulations are shown in Table 32.

TABLE 31

DOE variables and levels

| | Nominal Values | |
|---|---|---|
| Variable | Low | High |
| Protein Concentration (mg/mL) | 60 | 160 |
| pH | 6.0 | 6.3 |
| PS80:Protein Molar Ratio | 0.723 | 1.5 |
| Citrate Concentration (mM) | 0 | 40 |
| Histidine Concentration (mM) | 0 | 50 |

TABLE 32

Constants

| Constant | Value |
|---|---|
| Arginine Concentration (mM) | 125 |

Table 33 lists the formulations to be tested.

TABLE 33

Formulation details

| Formulation # | Protein (mg/ml) | Protein (mM) | His (mM) | Arg (mM) | PS80 % | pH | PS80:Protein Molar Ratio | Antioxidant | Antioxidant Concentration (nM) |
|---|---|---|---|---|---|---|---|---|---|
| 1 | 60 | 0.400 | 50 | 125 | 0.038 | 6.3 | 0.723 | Citric Acid | 25 |
| 2 | 60 | 0.400 | 50 | 125 | 0.079 | 6.3 | 1.5 | Citric Acid | 0 |
| 3 | 157 | 1.047 | 50 | 125 | 0.206 | 6.3 | 1.5 | Citric Acid | 25 |
| 4 | 160 | 1.067 | 50 | 125 | 0.101 | 6.3 | 0.723 | Citric Acid | 0 |
| 5 | 60 | 0.400 | 50 | 125 | 0.079 | 6.0 | 1.5 | Citric Acid | 25 |
| 6 | 110 | 0.733 | 50 | 125 | 0.069 | 6.0 | 0.723 | Citric Acid | 0 |
| 7 | 160 | 1.067 | 50 | 125 | 0.101 | 6.0 | 0.723 | Citric Acid | 25 |
| 8 | 160 | 1.067 | 50 | 125 | 0.210 | 6.0 | 1.5 | Citric Acid | 0 |
| 9* | 160 | 1.067 | 25 | 125 | 0.101 | 6.0 | 0.723 | Citric Acid | 25 |
| 10* | 160 | 1.067 | 25 | 125 | 0.140 | 6.0 | 1 | Citric Acid | 25 |
| 11 | 160 | 1.067 | 0 | 125 | 0.101 | 6.3 | 0.723 | Citric Acid | 40 |
| 12 | 160 | 1.067 | 0 | 125 | 0.210 | 6.3 | 1.5 | Citric Acid | 40 |
| 13 | 60 | 0.400 | 0 | 125 | 0.079 | 6.3 | 1.5 | Citric Acid | 40 |
| 14* | 160 | 1.067 | 0 | 125 | 0.210 | 6.1 | 1.5 | Citric Acid | 40 |
| 15* | 160 | 1.067 | 0 | 125 | 0.210 | 6.6 | 1.5 | Citric Acid | 40 |
| 16* | 160 | 1.067 | 0 | 125 | 0.140 | 6.3 | 1 | Citric Acid | 40 |

Each formulation is generated from a starting stock formulation containing anti-α4β7 antibody and diluted down with various excipient stock solutions. In order to achieve reasonable dilution volumes, the anti-α4β7 antibody stock solution used is shown in Table 34. Two different TFF operations are performed to achieve the formulations TFF 1 and 2. A portion of TFF 1 is used in a dialysis to achieve the formulation labeled "Dialysis".

TABLE 34

Starting Formulation buffer details

| Starting Formulation | Protein (mg/ml) | Total His (mM) | Total Citrate (mM) | Arg (mM) | pH |
|---|---|---|---|---|---|
| TFF 1 | 192.1 | 50 | 0 | 125 | 6.1 |
| TFF 2 | 206.1 | 0 | 40 | 125 | 6.3 |
| Dialysis | 169.65 | 25 | 25 | 125 | 6.0 |

For the dilution of the material to the desired formulation composition, stock solutions of each excipient in water are made at the concentrations specified by Table 35.

TABLE 35

Stock solution details

| Excipient | Concentration |
|---|---|
| Histidine (mM) | 220 |
| Arginine Hydrochloride (mM) | 625 |
| PS 80 (%) | 2.5 |
| Histidine Hydrochloride (mM) | 600 |
| Citric Acid (mM) (pH 6.3) | 1500 |
| Citric Acid (mM) (pH 6.0) | 1500 |

TABLE 35-continued

| Stock solution details | |
|---|---|
| Excipient | Concentration |
| Citrate (mM) | 600 |
| Sodium Citrate (mM) | 800 |

The dilution scheme for the formulations is detailed in Table 36 and 37.

TABLE 36

Dilution detail

| | Starting Formulation (uL) | Starting Formulation (mg) | His (uL) | His*HCl (uL) | Arg (uL) | Citrate Solution (uL) | PS80 (uL) | WFI (uL) |
|---|---|---|---|---|---|---|---|---|
| 1 | 4685.06 | 4961.01 | 1612.2 | 268.4 | 2063.0 | 250 | 227.3 | 5894.0 |
| 2 | 4685.06 | 4961.01 | 1612.2 | 268.4 | 2063.0 | 0 | 471.6 | 5899.7 |
| 3 | 12259.2 | 12981.31 | 724.1 | 0.0 | 548.2 | 250.0 | 1234.0 | 0.0 |
| 4 | 12493.49 | 13229.36 | 696.7 | 0.0 | 501.3 | 0 | 606.2 | 702.4 |
| 5 | 4685.06 | 4961.01 | 1002.8 | 491.9 | 2063.0 | 250 | 471.6 | 6035.7 |
| 6 | 8589.28 | 9095.18 | 545.0 | 334.4 | 1282.1 | 0 | 416.7 | 3832.4 |
| 7 | 12493.49 | 13229.36 | 87.2 | 176.9 | 501.3 | 250 | 606.2 | 884.9 |
| 8 | 12493.49 | 13229.36 | 87.2 | 176.9 | 501.3 | 0 | 1257.6 | 483.5 |
| 9 | 12260.8 | 12941.30 | 38.2 | 16.8 | 147.8 | 12.3 | 525.3 | 0.0 |
| 10 | 12260.8 | 12941.30 | 38.2 | 16.8 | 147.8 | 12.3 | 726.6 | 0.0 |

TABLE 37

Dilution details

| | Starting Formulation (uL) | Starting Formulation (mg) | Citrate (uL) | NaCitrate (uL) | Arg (uL) | PS80 (uL) | WFI (uL) |
|---|---|---|---|---|---|---|---|
| 11 | 9315.87 | 9944.69 | 8.3 | 128.0 | 536.8 | 484.9 | 1526.1 |
| 12 | 9315.87 | 9944.69 | 8.3 | 128.0 | 536.8 | 1006.1 | 1005.0 |
| 13 | 3493.45 | 3729.26 | 30.5 | 402.5 | 1701.3 | 377.3 | 5995.0 |
| 14 | 5822.42 | 6215.43 | 22.0 | 67.4 | 335.5 | 628.8 | 623.9 |
| 15 | 5822.42 | 6215.43 | 0.0 | 300.0 | 335.5 | 628.8 | 413.3 |
| 16 | 5822.42 | 6215.43 | 5.2 | 80.0 | 335.5 | 419.2 | 837.7 |

Compounding is performed based on the dilution scheme, and the starting formulation is weighed, while the other stock solutions are pipetted volumetrically. Formulations are filtered. 0.5 mL of formulation is aliquotted into as many 1 mL Long syringes as possible. The syringes are stoppered by the stoppering machine. The syringes are stored needle down.

Liquid formulations are tested analytically (appearance, pH, osmolality, density, DLS, SEC, CEX, and/or Brightwell) initially, and at 1 week, 40° C., 2 weeks, 40° C., 1 month 25 and 40° C., 2 months, 5 and 25° C., 3 months, 5 and 25° C., 6 months, 5 and 25° C., 9 months, 5 and 25° C., and 12 months, 5 and 25° C.

Specific formulation pulls according to Table 38 are also performed.

TABLE 38

Specific formulation pulls

| Formulation | Temperature | 1 Week | 2 Week | 1 Month | 2 Month | 3 Month | 6 Month | 9 Month | 12 Month | Extras |
|---|---|---|---|---|---|---|---|---|---|---|
| 1 | 5 | — | — | — | X | X | X | X | X | 1 |
| 2 | 5 | — | — | — | X | X | X | X | X | 1 |
| 3 | 5 | — | — | — | X | X | X | X | X | 1 |
| 4 | 5 | — | — | — | X | X | X | X | X | 1 |
| 5 | 5 | — | — | — | X | X | X | X | X | 1 |
| 6 | 5 | — | — | — | X | X | X | X | X | 1 |
| 7 | 5 | — | — | — | X | X | X | X | X | 0 |
| 8 | 5 | — | — | — | X | X | X | X | X | 1 |
| 9 | 5 | — | — | — | — | — | — | — | — | 3 |
| 10 | 5 | — | — | — | X | X | X | — | X | 0 |
| 11 | 5 | — | — | — | — | — | — | — | — | 5 |
| 12 | 5 | — | — | — | X | — | — | — | — | 4 |
| 13 | 5 | — | — | — | — | — | — | — | — | 5 |
| 14 | 5 | — | — | — | X | — | — | — | — | 1 |
| 15 | 5 | — | — | — | — | — | — | — | — | 2 |
| 16 | 5 | — | — | — | X | — | — | — | — | 1 |
| 1 | 25 | — | — | X | X | X | X | X | X | 1 |
| 2 | 25 | — | — | X | X | X | X | X | X | 1 |
| 3 | 25 | — | — | X | X | X | X | X | X | 1 |
| 4 | 25 | — | — | X | X | X | X | X | X | 1 |
| 5 | 25 | — | — | X | X | X | X | X | X | 1 |

TABLE 38-continued

Specific formulation pulls

| Formulation | Temperature | 1 Week | 2 Week | 1 Month | 2 Month | 3 Month | 6 Month | 9 Month | 12 Month | Extras |
|---|---|---|---|---|---|---|---|---|---|---|
| 6 | 25 | — | — | X | X | X | X | X | X | 1 |
| 7 | 25 | — | — | X | X | X | X | X | X | 1 |
| 8 | 25 | — | — | X | X | X | X | X | X | 1 |
| 9 | 25 | — | — | X | — | — | — | — | — | 3 |
| 10 | 25 | — | — | X | X | — | X | — | — | 0 |
| 11 | 25 | — | — | X | — | — | — | — | — | 5 |
| 12 | 25 | — | — | X | X | — | — | — | — | 4 |
| 13 | 25 | — | — | X | — | — | — | — | — | 6 |
| 14 | 25 | — | — | X | X | — | — | — | — | 1 |
| 15 | 25 | — | — | X | — | — | — | — | — | 2 |
| 16 | 25 | — | — | X | X | — | — | — | — | 1 |
| 1 | 40 | X | X | X | — | — | — | — | — | 1 |
| 2 | 40 | X | X | X | — | — | — | — | — | 1 |
| 3 | 40 | X | X | X | — | — | — | — | — | 1 |
| 4 | 40 | X | X | X | — | — | — | — | — | 1 |
| 5 | 40 | X | X | X | — | — | — | — | — | 1 |
| 6 | 40 | X | X | X | — | — | — | — | — | 1 |
| 7 | 40 | X | X | X | — | — | — | — | — | 1 |
| 8 | 40 | X | X | X | — | — | — | — | — | 1 |
| 9 | 40 | X | X | X | — | — | — | — | — | 0 |
| 10 | 40 | X | X | X | — | — | — | — | — | 0 |
| 11 | 40 | X | X | X | — | — | — | — | — | 0 |
| 12 | 40 | X | X | X | — | — | — | — | — | 0 |
| 13 | 40 | X | X | X | — | — | — | — | — | 0 |
| 14 | 40 | X | X | X | — | — | — | — | — | 0 |
| 15 | 40 | X | X | X | — | — | — | — | — | 0 |
| 16 | 40 | X | X | X | — | — | — | — | — | 0 |

Example 12

A formulation containing 160 mg/mL protein, 50 mM histidine, 25 mM citrate, 125 mM arginine at pH 6.5 was tested for stability in either a glass syringe or two different COP plastic syringes. At 5° C. and 25° C. after 12 months, the amount of aggregates and monomer were comparable between the plastic and glass syringes.

TABLE 39

| Formulation # | PS80: Protein Molar Ratio | Syringe Material | Change in SEC Aggregates After 12 Months at 5° C. (%) | Change in SEC Aggregates After 12 Months at 25° C. (%) | Amount of Monomer After 12 Months at 5° C. (%) | Amount of Monomer After 12 Months at 25° C. (%) |
|---|---|---|---|---|---|---|
| 1 | 1.5 | COP Manufacturer 1 | 0.2 | 1.0 | 98.3 | 96.8 |
| 2 | 1.5 | COP Manufacturer 2 | 0.2 | 1.6 | 98.3 | 96.9 |
| 3 | 1.5 | Glass | 0.2 | 1.4 | 98.4 | 96.8 |
| 4 | 1 | Glass | 0.2 | 1.6 | 98.3 | 96.8 |

Example 13

Bioavailability of Vedolizumab Administered by Subcutaneous and Intramuscular Injection A phase I study of the bioavailability of vedolizumab administered by subcutaneous and intramuscular injection to healthy male subjects was completed. A total of 42 healthy males were enrolled in the study. The subjects were divided into three groups (subcutaneous, intramuscular, and intravenous administration) of 14 subjects each. The subjects were administered 180 mg of vedolizumab on one day. The dose was reconstituted from a lyophilized formulation of 60 mg/ml antibody in 50 mM histidine, 125 mM arginine, 0.06% polysorbate 80, 10% sucrose, at pH 6.3. For the intramuscular and subcutaneous subjects, the dose was divided into two injections of 1.5 ml each. Blood was sampled to determine the plasma vedolizumab concentration and the bioavailability of vedolizumab in each set of subjects was determined.

No serious adverse events or significant infections, clinically significant abnormalities, positive subjective/objective RAMP checklists, nor clinically significant ECG findings were reported.

PK/PD modeling and simulation was completed to determine the dose and regimens of extra-vascular doses that result in similar exposures as the intravenous doses in order to maintain this desired serum concentrations at trough levels.

Figure 18:
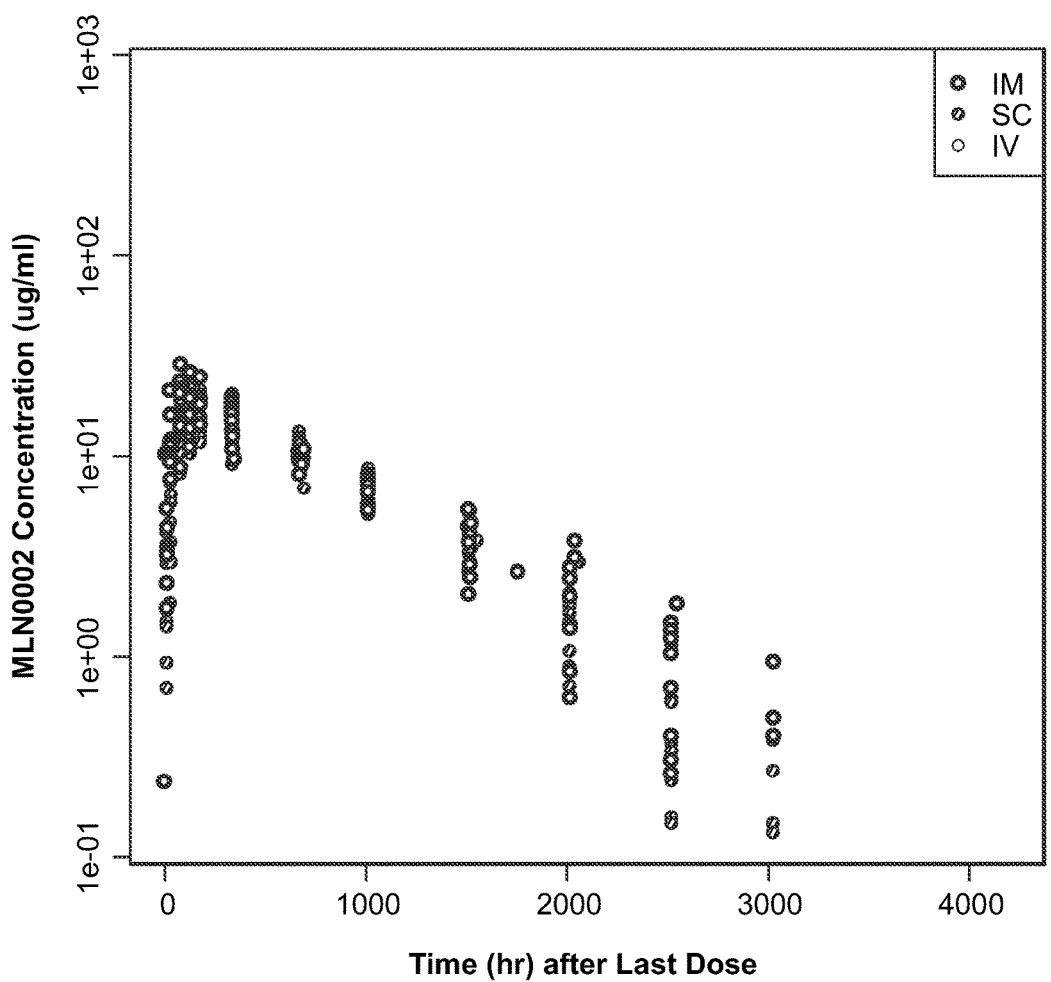
FIG. 18 shows the absorption profile of vedolizumab. The graph shows that concentrations of the intramuscular and subcutaneous doses generally overlap. There are no apparent gross differences in the absorption profiles of these routes of administration.

The absorption profile (FIG. 18) showed that concentrations of the intramuscular and subcutaneous doses generally overlap. There are no apparent gross differences in the absorption profiles of these routes of administration. The absolute bioavailability of vedolizumab following SC injection was approximately 75% and following IM injection was approximately 80%.

Example 14

Modeling Subcutaneous Dose Regimens

PK/PD modeling and simulation was completed to determine the dose and regimens of extra-vascular doses that result in similar exposures as the intravenous doses in order to maintain certain serum concentrations at trough levels.

A final combined dataset (IV, SC and IM data) showed two compartment linear models parameterized in terms of clearance (CL) and central volume of distribution (V2), peripheral volume of distribution (V3), an extra-vascular route dependent absorptionrate constant (KA) and the relative bioavailability (compared to intravenous administration) of the extra-vascular doses (F). IIV terms were included on CL, V2 and V3 with body weight as the only covariate influencing CL and V3 through an allometric effect.

Model acceptability and predictability was demonstrated through bootstrap parameter estimates, visual predictive checks and goodness of fit plot. Analysis of the model identified body weight as a predictor for the PK of vedolizumab with the variability in the PK attributed to between subject and within subject components.

Once the model was demonstrated to be adequate for simulation, simulations were performed in order to assess the effect of route of administration (IV, IM or SC), and assess the effect of frequency of dosing (weekly, every 2 weeks, every 4 weeks, and every 8 weeks) on the steady state trough concentrations. Based on these values and the relative bioavailability of vedolizumab following IM and SC administration (F=69.5%), doses were selected to achieve similar trough concentrations as the IV doses.

Simulations modeled doses and regimens to match intravenous induction and maintenance regimens. The targets were both exposure (area under serum drug concentration-time curve (AUC)) and trough drug concentration. Tables 40-43 provide results of simulations.

TABLE 40

Induction regimen matching an IV AUC during weeks 0-6

| Route | Dose | Frequency |
|---|---|---|
| IV | 300 mg | Week 0 & 2 |
| SC | 485 mg | Week 0 & 2 |
| SC | 160 mg | Every other day (6 doses) |
| SC | >160 mg | Weekly (6 doses) |

TABLE 41

Induction regimen matching an IV trough concentration, weeks 0-6

| Route | Dose | Frequency |
|---|---|---|
| IV | 300 mg | Week 0 & 2 |
| SC | >160 mg | Week 0 & 2 |
| SC | 100 mg | Every week (6 doses) |
| SC | 160 mg | Every other day (for 2 weeks) |

TABLE 42

Maintenance regimen matching a 300 mg IV dose every 4 weeks

| Frequency | Route | Dose matching 4 wk IV steady state trough concentration | Dose matching 4 wk IV AUC |
|---|---|---|---|
| Once every 4 weeks | IV | 300 | 300 |
| | IM | 432 | 432 |
| | SC | 432 | 432 |
| Once every 2 weeks | IV | 115 | 150 |
| | IM | 165 | 216 |
| | SC | 165 | 216 |
| Every week | IV | 50 | 75 |
| | IM | 72 | 108 |
| | SC | 72 | 108 |

TABLE 43

Maintenance regimen matching a 300 mg IV dose every 8 weeks

| Frequency | Route | Dose matching 8 wk IV steady state trough concentration | Dose matching 8 wk IV AUC |
|---|---|---|---|
| Once every 8 weeks | IV | 300 | 300 |
| | IM | 432 | 432 |
| | SC | 432 | 432 |
| Once every 4 weeks | IV | 90 | 150 |
| | IM | 125 | 216 |
| | SC | 125 | 216 |
| Once every 2 weeks | IV | 35 | 75 |
| | IM | 50 | 108 |
| | SC | 50 | 108 |
| Every week | IV | 15 | 37.5 |
| | IM | 22 | 54 |
| | SC | 22 | 54 |

Example 15

Phase 2a Multiple Dose Study

A Phase 2a multiple dose study can assess the safety, tolerability and steady state PK of vedolizumab following multiple doses of vedolizumab by the subcutaneous administration route and to assess the relative bioavailability of the subcutaneous regimen compared with the intravenous regimen. The development of HAHA and neutralizing HAHA and the effect on PD of multiple doses of vedolizumab following subcutaneous administration can be assessed.

Ulcerative colitis patients having a partial Mayo score of 1-12 and Crohn's disease patients having a CDAI greater than 150 can be included in the study. Cohorts can receive an induction regimen of vedolizumab (300 mg) administered IV at weeks 0 and 2, followed by a maintenance regimen of either Vedolizumab (300 mg) administered IV every 4 weeks at weeks 6-22

Vedolizumab (300 mg) administered IV every 8 weeks at weeks 6-22

Vedolizumab (108 mg) administered SC every week at weeks 6-22

Vedolizumab (108 mg) administered SC every 2 weeks at weeks 6-22

Vedolizumab (165 mg) administered SC every 3 weeks at weeks 6-22.

Samples can be collected before dosing on day 1, and then again on day 1 (12 hours), 2, 3, 5, 8, 15, 29, 43, 127, 127 (12 hours), 128, 129, 131, 134, 141, and 155 to assess PK and PD.

Example 16

Long-Term Clinical Experience with Vedolizumab for the Treatment of IBD

A phase 2 open-label safety extension study was completed to assess the long-term pharmacokinetics (PK), pharmacodynamics (PD), safety, and efficacy of vedolizumab. Patients were aged 18 to 75 years old, and had either previously participated in an earlier PK/PD/safety study in ulcerative colitis patients or had IBD symptoms for at least 2 months confirmed endoscopically and/or histopathologically and/or radiologically within 36 months of screening.

All patients received an intravenous dosing regimen of either 2 mg/kg or 6 mg/kg of vedolizumab (5 mg/mL antibody, 20 mM citrate/citric acid, 125 mM sodium chloride, 0.05% polysorbate 80, pH 6.0 (stored long term $-70°$ C. and up to 3 mo $-20°$ C.)) on days 1, 15 and 43, followed by a dose every 8 weeks for up to a total of 78 weeks. Patients were either treatment-naïve ulcerative colitis or Crohn's disease patients, or ulcerative colitis patients that had participated in an earlier clinical trial.

Efficacy/quality of life (QoL); partial Mayo score (PMS), Crohn's disease activity index (CDAI), and Inflammatory Bowel Disease Questionnaire (IBDQ) were used to assess the results of the study.

PK Results

Mean pre-infusion vedolizumab concentrations were dose proportional, and remained steady and detectable throughout the study.

PD Results

Receptors (% ACT-1+[CD4+CD45RO HIGH] and % MADCAM+[CD4+CD45RO HIGH] were almost fully inhibited throughout the study period at all dose levels.

Partial Mayo Score

Baseline mean PMS was higher for treatment-naïve ulcerative colitis patients (5.4) than for ulcerative colitis rollover patients (2.3). By day 43, mean PMS showed a pronounced decrease for both rollover and treatment-naïve ulcerative colitis patients. By day 155, mean scores of the two groups were similar. Mean PMS continued to decrease through day 267, and leveled off thereafter.

Crohn's Disease Activity Index

CD patients' mean CDAI decreased from 294.6 at baseline to 237.7 at Day 43, and continued to decrease through day 155 (156.1).

IBDQ

Ulcerative colitis rollover patients had the highest mean IBDQ scores at baseline. By day 43, mean IBDQ scores had increased in all three disease groups. Mean IBDQ scores continued to increase over time in all 3 disease groups, reaching a maximum at day 155 for Crohn's Disease patients, and at day 491 for treatment-naïve ulcerative colitis patients and ulcerative colitis rollover patients.

C— Reactive Protein

Both ulcerative colitis rollover and Crohn's disease patients showed decreased mean CRP levels through day 155 and then leveled off. Treatment-naïve ulcerative colitis patients had a lower mean CRP level at baseline than ulcerative colitis rollover patients (2.28 v. 7.09). Mean CRP levels of the treatment-naïve ulcerative colitis patients remained relatively constant at all time points assessed.

Other Safety Results

No systematic opportunistic infections (including PML) were reported during the study. One patient tested positive for JC viremia at a single time point, though was negative for JCV at all other time points. Three of 72 patients (4%) had positive HAHA results (two of these were transiently positive). The study showed no evidence of liver toxicity, lymphocytosis, or lymphopenia, or any other drug-associated laboratory changes.

Conclusions

Vedolizumab administered at 2.0 or 6.0 mg/kg once every 8 weeks for up to 78 weeks achieved target receptor saturations, was associated with durable mean decreases in disease activity and improved IBDQ scores, was generally safe and well tolerated, and demonstrated acceptable immunogenicity.

Example 17

Induction and Maintenance of Response and Remission in Patients with Moderately to Severely Active Ulcerative Colitis A single trial comprising two randomized, double blind, multi-center studies designed to evaluate induction and maintenance of response and remission in patients with moderately to severely active ulcerative colitis. Demographic and baseline disease characteristics were comparable across all treatment groups.

The induction study, using intravenous administration, compared placebo against vedolizumab, at a 300 mg dose reconstituted from a lyophilized formulation of 60 mg/ml antibody in 50 mM histidine, 125 mM arginine, 0.06% polysorbate 80, 10% sucrose, at pH 6.3, with an endpoint at 6 weeks after 2 doses of vedolizumab.

The maintenance study, using the same formulation and route of administration as the induction study, compared placebo against vedolizumab dosed every four weeks, and placebo against vedolizumab dosed every eight weeks. The endpoint of this study was at 52 weeks, analyzing the induction responder population.

Blood samples were collected to measure concentrations of vedolizumab during the study. The mean serum concentration of vedolizumab at the end of the induction phase was 20 to 30 µg/mL. The mean vedolizumab trough serum concentrations at steady state after 30 min IV infusion of 300 mg dose administration were between 9 to 13 µg/mL for the q8 wks regimen (8 week regimen) and between 35 to 40 µg/mL for the q4 wks regimen (4 week regimen). At the end of infusion, the vedolizimab median plasma concentrations were between 98 and 101 µg/mL for the q8ks regimen and around 129 and 137 µg/mL for the q4 wks regimen.

Summaries of the responses of the induction and maintenance studies are provided in Tables 44-47. A significantly greater proportion of vedolizumab-treated patients achieved clinical response, remission, and mucosal healing at 6 weeks, compared with placebo (Table 44). 39% of the induction phase intent-to-treat population had prior anti-TNFα failure. Clinical response and remission rates were higher in vedolizumab than placebo patients among both those with prior anti-TNF failure and those with no prior anti-TNF exposure. In preliminary analyses through week 6, rates of adverse events (AEs), serious AEs, and adverse events leading to study discontinuation were higher in the placebo group than vedolizumab group. A significantly greater proportion of vedolizumab patients than placebo patients achieved clinical remission, mucosal healing, and corticosteroid-free remission at 52 wks and durable response and remission (Table 45). 32% of the maintenance study population had prior anti-TNFα failure. Clinical remission and durable clinical response rates were greater with vedolizumab than placebo in both TNF failure and TNF naïve patients. In the safety population (N=895) for wks 0-52, rates of adverse events (AEs), serious AEs, and serious infections were similar between vedolizumab and placebo groups. No increase in rates of opportunistic or enteric infections was observed in the vedolizumab group.

TABLE 44

Induction Study Results-Primary and Key Secondary Endpoints

| Efficacy Endpoints | Placebo | Vedolizumab | Difference/RR | P value |
|---|---|---|---|---|
| Clinical Response (%) | 25.5% | 47.1% | 21.7%/1.8 | <0.0001 |
| Clinical Remission (%) | 5.4% | 16.9% | 11.5%/3.1 | 0.0010 |
| Mucosal Healing (%) | 24.8% | 40.9 | 16.1%/1.6 | 0.0013 |

TABLE 45

Maintenance Study Results-Primary and Key Secondary Endpoints

| Efficacy Endpoint | Placebo N = 126 | VDZ Q8 N = 122 | VDZ Q4 N = 125 | Difference/RR Q8 vs. Pb Q4 vs. Pb | P value |
|---|---|---|---|---|---|
| Clinical Remission (%) | 15.9 | 41.8 | 44.8 | 26.1/2.7 29.1/2.8 | <0.0001 <0.0001 |
| Durable Response (%) | 23.8 | 56.6 | 52.0 | 32.8/2.4 28.5/2.2 | <0.0001 <0.0001 |
| Mucosal Healing (%) | 19.8 | 51.6 | 56.0 | 32.0/2.6 36.3/2.8 | <0.0001 <0.0001 |
| Durable Remission (%) | 8.7 | 20.5 | 24.0 | 11.8/2.4 15.3/2.8 | 0.0090 0.0011 |
| Corticosteroid-free Remission (%) | 13.9 n = 72 | 31.4 n = 70 | 45.2 N = 73 | 17.6/2.3 31.4/3.3 | 0.0133 <0.0001 |

TABLE 46

Induction Study: Clinical Response and Remission at 6 Weeks in Patients with Prior Anti-TNF-α Antagonist Failure and Without Anti-TNF Exposure, ITT Population Patients with Prior Anti-TNF-α Antagonist Failure (39%)

| Endpoint | Placebo N = 63 | Vedolizumab N = 82 | Difference | 95% Cl |
|---|---|---|---|---|
| Clinical Response (%) | 20.6 | 39.0 | 18.4 | 3.9, 32.9 |
| Clinical Remission (%) | 3.2 | 9.8 | 6.6 | −9.8, 22.8 |

Patients Without Anti-TNF-α Antagonist Exposure (55%)

| Endpoint | Placebo N = 76 | Vedolizumab N = 130 | Difference | 95% Cl |
|---|---|---|---|---|
| Clinical Response (%) | 26.3 | 53.1 | 26.8 | 13.7, 39.9 |
| Clinical Remission (%) | 6.6 | 23.1 | 16.5 | 2.4, 30.2 |

TABLE 47

Clinical Remission and Durable Clinical Response at 52 Weeks: Patients with Prior Anti-TNF-α Antagonist Failure or Without Anti-TNF-α Antagonist Exposure ITT Population Patients with Prior Anti-TNF-α Antagonist Failure (32%)

| Endpoint | Placebo N = 38 | VDZ Q8 Wks N = 43 | VDZ Q4 Wks N = 40 | Difference Q8 wks vs Placebo Q4 wks vs. Placebo | 95% Cl |
|---|---|---|---|---|---|
| Clinical remission (%) | 5.3 | 37.2 | 35.0 | 31.9 29.7 | 10.3, 51.4 7.4, 49.4 |
| Durable Clinical Response (%) | 15.8 | 46.5 | 42.5 | 30.7 26.7 | 11.8, 49.6 7.5, 45.9 |

Patients without Anti-TNF-α Antagonist Exposure (60%)

| Endpoint | Placebo N = 79 | VDZ Q8 wks N = 72 | VDZ Q4 wks N = 73 | Difference Q8 wks vs. Placebo Q4 wks vs. Placebo | 95% Cl |
|---|---|---|---|---|---|
| Clinical Remission (%) | 19.0 | 45.8 | 47.9 | 26.8 29.0 | 12.4, 41.2 14.6, 43.3 |
| Durable Clinical Response (%) | 26.6 | 65.3 | 56.2 | 38.7 29.6 | 24.0, 53.4 14.6, 44.6 |

Example 18

Induction and Maintenance of Response and Remission in Patients with Moderately to Severely Active Crohn's Disease A single trial comprising two randomized, double blind, multi-center studies designed to evaluate induction and maintenance of response and remission in patients with moderately to severely active Crohn's Disease. Demographic and baseline disease characteristics were comparable across all treatment groups.

The induction study, using intravenous administration, compared placebo against vedolizumab, at a 300 mg dose reconstituted from a lyophilized formulation of 60 mg/ml antibody in 50 mM histidine, 125 mM arginine, 0.06% polysorbate 80, 10% sucrose, at pH 6.3, with an endpoint at 6 weeks after 2 doses of vedolizumab.

The maintenance study, using the same formulation and route of administration as the induction study, compared placebo against vedolizumab dosed every four weeks, and placebo against vedolizumab dosed every eight weeks. The endpoint of this study was at 52 weeks, analyzing the induction responder population.

Surprisingly, this study showed that Q4 and Q8 week groups yielded very similar results. Summaries of the responses of the induction and maintenance studies are provided in Tables 48-51. A significantly greater proportion of vedolizumab-treated patients achieved clinical remission and enhanced response, compared with placebo (Table 48). Clinical remission and enhanced response rates were higher in vedolizumab than placebo patients among both those with prior anti-TNF failure and those with no prior anti-TNF exposure. Rates of adverse events (AEs), serious AEs, and serious infections were similar between vedolizumab and placebo groups. No increase in rates of opportunistic or enteric infections was observed in the vedolizumab group.

TABLE 48

Induction Study Results-Primary and Secondary Endpoints

| Endpoints | Placebo N = 148 | Vedolizumab N = 220 | Adjusted Difference/RR | P value |
|---|---|---|---|---|
| Clinical Remission (%) | 6.8% | 14.5% | 7.8%/2.1 | 0.0206 |
| Enhanced Response (%) | 25.7% | 31.4% | 5.7%/1.2 | 0.2322 |
| Mean CRP Change (μg/mL) | −3.6 N = 147 | −2.9 N = 220 | | 0.9288 |

TABLE 49

Maintenance Study Results-Primary and Key Secondary Endpoints

| Efficacy Endpoint | Placebo N = 153 | VDZ Q8 N = 154 | VDZ Q4 N = 154 | Adj. Difference/ RR Q8 vs. Pb Q4 vs. Pb | P value |
|---|---|---|---|---|---|
| Clinical Remission (%) | 21.6 | 39.0 | 36.4 | 17.4/1.8 14.7/1.7 | 0.0007 0.0042 |
| Enhanced Response (%) | 30.1 | 43.5 | 45.5 | 13.4/1.4 15.3/1.5 | 0.0132 0.0053 |
| Corticosteroid-free Remission (%) | 15.9 N = 82 | 31.7 N = 82 | 28.8 N = 80 | 15.9/2.0 12.9/1.8 | 0.0154 0.0450 |
| Durable Remission (%) | 14.4 | 21.4 | 16.2 | 7.2/1.5 2.0/1.1 | 0.1036 0.6413 |

TABLE 50

Clinical Remission and Enhanced Response at 6 Weeks in Patients with Prior Anti-TNF-α Antagonist Failure and Without Anti-TNF Exposure, ITT Population Patients with Prior Anti-TNF-α Antagonist Failure (48%)

| Endpoint | Placebo N = 70 | Vedolizumab N = 105 | Difference | 95% CI |
|---|---|---|---|---|
| Clinical Remission (%) | 4.3 | 10.5 | 6.2 | (−9.1, 21.3) |
| Enhanced Response (%) | 22.9 | 23.8 | 1.0 | (−11.8, 13.7) |

Patients Without Anti-TNF-α Antagonist Exposure (50%)

| | Placebo N = 76 | Vedolizumab N = 130109 | Difference | 95% CI |
|---|---|---|---|---|
| Clinical Remission (%) | 9.2 | 17.4 | 8.2 | (−1.4, 17.9) |
| Enhanced Response (%) | 30.3 | 42.2 | 11.9 | (−1.9, 25.8) |

TABLE 51

Clinical Remission and Enhanced Response at 52 Weeks: Patients with Prior Anti-TNF-α Antagonist Failure or Without Anti-TNF-α Antagonist Exposure ITT Population Patients with Prior Anti-TNF-α Antagonist Failure (51%)

| Endpoint | Placebo N = 78 | VDZ Q8 Wks N = 82 | VDZ Q4 Wks N = 77 | Difference Q8 wks vs Placebo Q4 wks vs. Placebo | 95% CI |
|---|---|---|---|---|---|
| Clinical remission (%) | 12.8 | 28.0 | 27.3 | 15.2 14.5 | (3.0, 27.5) (2.0, 26.9) |
| Enhanced Response (%) | 20.5 | 29.3 | 37.7 | 8.8 17.1 | (−4.6, 22.1) (3.1, 31.2) |

Patients without Anti-TNF-α Antagonist Exposure (45%)

| | Placebo N = 71 | VDZ Q8 wks N = 66 | VDZ Q4 wks N = 71 | Difference Q8 wks vs. Placebo Q4 wks vs. Placebo | 95% CI |
|---|---|---|---|---|---|
| Clinical Remission (%) | 26.8 | 51.1 | 46.5 | 24.8 19.7 | (8.9, 40.6) (4.2, 35.2) |
| Enhanced Response (%) | 38.0 | 60.6 | 53.5 | 22.6 15.5 | (6.3, 38.9) (−0.7, 31.7) |

Example 19

Induction of Response and Remission in Patients with Moderate to Severely Active Crohn's Disease A randomized, double blind, placebo controlled multi-center study was completed to evaluate the induction effect of vedolizumab at 300 mg doses (reconstituted from a formulation of 60 mg/ml antibody in 50 mM histidine, 125 mM arginine, 0.06% polysorbate 80, 10% sucrose, at pH6.3 which was lyophilized), in TNFα antagonist failure patients at week 6 (after 2 doses—0 and 2 weeks) and at week 10 (after 3 doses). The study consisted of 416 patients, 75% of whom were TNFα antagonist failures, and 25% of whom were TNFα naïve. Demographics and concomitant IBD medication were balanced across treatment groups. Baseline disease characteristics were also balanced across treatment groups, except for baseline disease activity.

The primary endpoint designated for the study was week 6 remission (%) in anti-TNF-α antagonist failure population. The key secondary endpoints that were evaluated (sequential testing procedure) were: week 6 remission (%) in overall population, week 10 remission (%) in anti-TNF-α antagonist failure and overall population (using Hochberg procedure), week 6 and 10 sustained remission (%) in anti-TNF-α antagonist failure and overall population (using Hochberg procedure), and week 6 enhanced response (%) in anti-TNF-α antagonist failure population.

TABLE 52

| Baseline CDAI: | | | |
|---|---|---|---|
| | Placebo | Vedolizumab | p-value |
| TNF ITT: Mean (Std Dev) | 306.1 (55.43) | 316.1 (52.63) | 0.0945 |
| Overall ITT: Mean (Std Dev) | 301.3 (54.97) | 313.9 (53.17) | 0.0153 |

TABLE 53

Induction Study Results: Primary and Key Secondary Endpoints

| | Endpoints | | | | | | | |
|---|---|---|---|---|---|---|---|---|
| | TNF ITT (N = 315) | | | | Overall ITT (N = 416) | | | |
| | PLA N = 157 | VDZ N = 158 | Diff (RR) | P-value | PLA N = 207 | VDZ N = 209 | Diff (RR) | P-value |
| Primary Wk6 Remission | 12.1% | 15.2% | 3.0% (1.2) | 0.4332 | | | | |
| 1st Secondary Wk6 Remission | | | | | 12.1% | 19.1% | 6.9% (1.6) | 0.0478 |
| 2nd Secondary Wk10 Remission | 12.1% | 26.6% | 14.4% (2.2) | 0.0012 | 13% | 28.7% | 15.5% (2.2) | <0.0001 |
| Sustained Remission (both Wk 6&10) | 8.3% | 12.0% | 3.7% (1.4) | 0.2755 | 8.2% | 15.3% | 7% (1.9) | 0.0249 |
| Enhanced Response (CDAI100) | 22.3% | 39.2% | 16.9% (1.8) | 0.0011 | | | | |

TABLE 54

Results in Anti-TNF-α Antagonist Naive Patients (n = 101, 24% of overall)

| | Placebo % | Vedolizumab % | Difference % | 95% Cl |
|---|---|---|---|---|
| Remission Week 6 | 12 | 31.4 | 19.1 | (3.3, 35.0) |
| Remission Week 10 | 16 | 35.3 | 19.2 | (2.4, 35.8) |

TABLE 55

Study Results: Clinical Remission at Weeks 6 and 10, Key Subgroup-Previous Tx Failures, ITT Overall

| Subgroup | Variable | Placebo | VDZ | Diff | 95% Cl |
|---|---|---|---|---|---|
| Any prior anti-TNF failure (75% of ITT) | N | 156 | 155 | | |
| | Wk 6 Rem (%) | 12.8 | 14.8 | 2 | (−5.7, 9.7) |
| | Wk 10 Rem (%) | 12.8 | 26.5 | 13.6 | (4.9, 22.3) |
| Prior immunomodulator failure but not anti-TNF failure (21% ITT) | N | 45 | 44 | | |
| | Wk 6 Rem (%) | 11.1 | 31.8 | 20.7 | (−0.5, 39.7) |
| | Wk 10 Rem (%) | 15.6 | 31.8 | 16.3 | (−1.1, 33.6) |
| Prior corticosteroid failure only (3% TT) | N | 5 | 9 | | |
| | Wk 6 Rem (%) | 0 | 33.3 | 33.3 | (−23.9, 75.7) |
| | Wk 10 Rem (%) | 0 | 44.4 | 44.4 | (−13.4, 85.3) |

The study showed that TNF-α antagonist failure patients required 3 doses for induction of remission. Remission rates in TNF-α antagonist failure patients increased between week 6 and week 10, but only for the vedolizumab group (not placebo). Remission rates for TNF-α antagonist naïve patients did not increase substantially between week 6 and 10. Of the TNF-α antagonist failure population with a high degree of disease severity, 43% never responded to a TNF-α antagonist, and 45% lost response.

Example 20

Stability

Various different anti-α4β7 antibody formulations were tested for stability over the course of 6 to 24 months at 5° C. (Tables 6 and 7). Formulations having a pH of 6.0-6.2 showed approximately less than 4% major species degradation after 6 months and at 24 months.

Various different anti-α4β7 antibody formulations were tested for stability by SEC for up to 24 months (Tables 4 and 5). The formulations with 60 mg/mL protein concentration and containing 25 mM citrate had a change in aggregates of 0.1-0.2% after 2 years, while formulations containing 160 mg/mL protein and 25 mM citrate had an increase of aggregates of approximately 0.3% over 2 years. There was an increase of 0.6-1.1% aggregates for formulations containing 60, 110, or 160 mg/mL protein with no citrate. For the formulations tested containing citrate, but no histidine, after 12 months and 24 months, there was approximately 0.3-0.4% growth of aggregates.

Example 21

Determination of the Effect of Vedolizumab on the CD4:CD8 Ratio

Healthy subjects ages 18-45 were treated with a single 450 mg dose of vedolizumab reconstituted from a lyophilized formulation of 10% sucrose and diluted into an infusion system of 0.9% saline. Cerebrospinal fluid (CSF) was collected by lumbar puncture before (baseline) and 5 weeks after the single 450-mg dose of vedolizumab. Each subject served as his/her own control.

A 5-week time point was selected based on a previous study that showed patients with MS treated with natalizumab demonstrated effects on CSF CD4+:CD8+ lymphocyte ratio and reduction in number of brain lesions after only one dose (Stuve et al. Arch Neurol. 2006; 63:1383-1387; Stuve et al. Ann Neurol. 2006; 59:743-747. Miller et al. N Engl J Med. 2003; 348(1):15-23); and also because at 5 weeks, a 450-mg dose of vedolizumab is sufficient to saturate the target and provides serum concentrations that exceed estimated steady-state trough levels associated with the phase 3 dose regimen of 300 mg every 4 weeks.

Approximately 15 mL CSF was obtained from each subject for immunophenotyping. CSF samples were included for analyses if they met the following criteria: ≤10 RBCs/µL per sample (to minimize peripheral blood contamination); negative CSF culture result; adequate T-Lymphocyte numbers in each flow cytometry sample; and no detection of serum antibodies to vedolizumab.

Week 5 median (34.80 µg/mL) and individual subject serum vedolizumab concentrations (range 24.9-47.9 µg/mL) were higher than projected steady-state trough concentration (~24 µg/mL) for the phase 3 dose regimen. A high degree (>90%) of α4β7 receptor saturation was observed at week 5 as measured by MAdCAM-1-Fc, indicating vedolizumab's saturation of its target at the time of endpoint assessment.

Vedolizumab was not detected in any CSF sample (detection limit=0.125 µg/mL).

Effect on CD4+ and CD8+T Lymphocyte Numbers and Ratio

Vedolizumab did not significantly reduce CD4+:CD8+ ratio (Table 56). None of the subjects had a postdose CD4+:CD8+ ratio <1 ($p<0.0001$ (1-sided t-test)). Vedolizumab did not significantly reduce the number of CD4+ or CD8+ T lymphocytes in CSF. In addition, there were no significant changes in CSF CD4+ and % CD8+ T lymphocytes (Table 57). Also, no significant changes in peripheral blood WBC, CD4+ and CD8+ memory T lymphocytes (Table 58) were observed.

TABLE 56

Effect of Treatment on CSF CD4+:CD8+ Ratio (Evaluable Population, n = 13)

|  | Baseline | Week 5 | CD4+:CD8+ Ratio Difference† |
|---|---|---|---|
| CD4+:CD8+ ratio Mean (SE) Range | 3.59 (0.273) 1.53-5.67 | 3.60 (0.265)* 1.42-5.15 | 0.01 (0.197) |
| 90% 2-sided CI for ratio | 3.00-4.19 | 3.132, 4.077 |  |
| 90% 2-sided CI for difference |  |  | −0.337, 0.363 |

CI = confidence interval
*$p < 0.0001$ (one sided one sample t-test for H0: µ < 1 vs H1: µ >= 1).
†Difference is defined as week 5 ratio minus baseline ratio

TABLE 57

Treatment Effect on CSF CD4+ and CD8+ Lymphocyte Count (Evaluable Population, n = 13)

|  | Baseline | Week 5 |
|---|---|---|
| CD4+ as % of Lymphocytes, mean (SD) | 75.160 (7.3831) | 74.215 (6.3732) |
| CD8+ as % of Lymphocytes, mean (SD) | 22.272 (5.4320) | 22.007 (6.1624) |

TABLE 58

Peripheral Blood Memory T Lymphocytes (RO+) Counts (Evaluable Population, n = 13)

|  | Baseline Mean (SD) | Week 5 Mean (SD) |
|---|---|---|
| CD4+CD45RO+ | 27.85 (4.98) | 27.06 (5.02) |
| CD8+CD45RO+(%) | 11.24 (3.40) | 10.78 (2.98) |

SUMMARY

Vedolizumab did not affect CSF CD4+ and CD8+ cell counts or CD4+:CD8+ ratio in healthy volunteers after a single 450 mg dose. None of the subjects had a reduction in the post-dose CSF CD4+:CD8+ ratio to less than 1. Vedolizumab was not detected in CSF. In addition, there was no change observed in the total WBCs or memory T lymphocyte CD4+ and CD8+ subsets in peripheral blood. Saturation of the target (α4β7) in blood occurred in all subjects at the time of endpoint assessment. The CSF CD4+ and CD8+ lymphocyte levels and ratio were similar to those previously reported in the literature.

These results are consistent with vedolizumab's lack of effect on both physiologic CNS immune surveillance and pathologic CNS inflammation of monkeys.

While this invention has been particularly shown and described with references to preferred embodiments thereof, it will be understood by those skilled in the art that various changes in form and details may be made therein without departing from the scope of the invention encompassed by the appended claims.

TABLE 59

Sequences

| SEQ ID NO: | Sequence Shown | Description |
|---|---|---|
| 1 | FIG. 1 | DNA encoding heavy chain of humanized anti-α4β7 immunoglobulin |
| 2 | FIG. 1 | Amino acid sequence of heavy chain of humanized anti-α4β7 immunoglobulin |
| 3 | FIG. 2 | DNA encoding the light chain of humanized anti-α4β7 immunoglobulin |

TABLE 59-continued

Sequences

Figure 7:
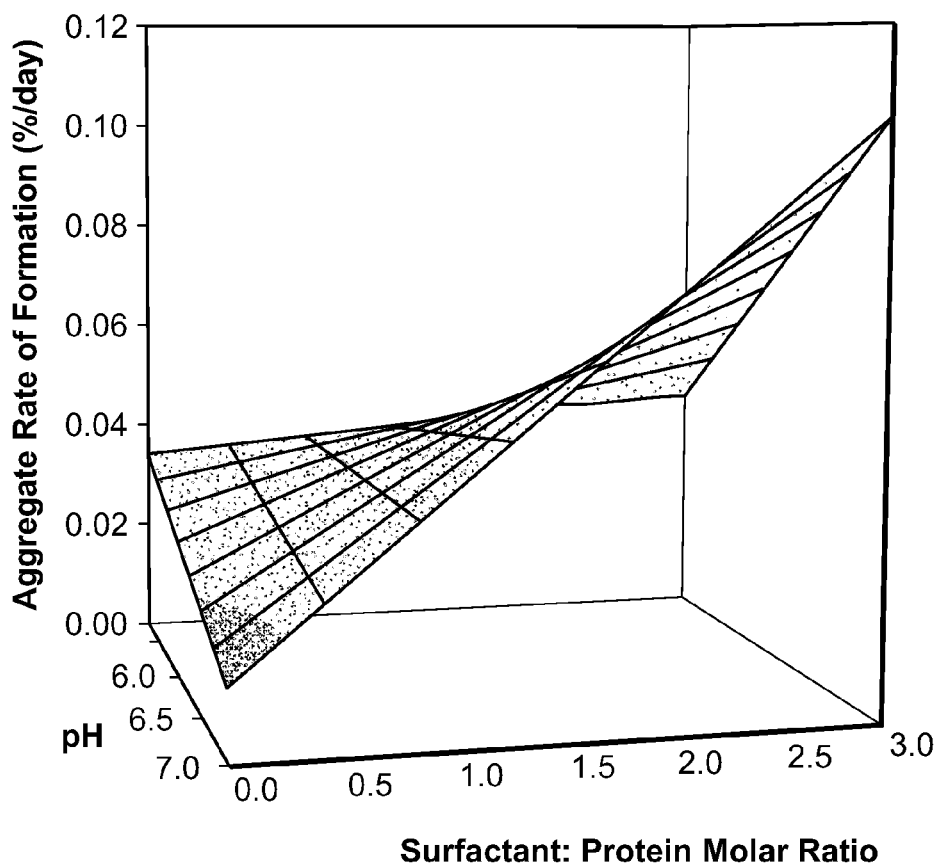
FIG. 7 is a graph showing that at polysorbate 80:protein molar ratios greater than 1.5, the aggregate formation rate increases as pH increases.

| SEQ ID NO: | Sequence Shown | Description |
| --- | --- | --- |
| 4 | FIG. 2 | Amino acid sequence of light chain of humanized anti-α4β7 immunoglobulin |
| 5 | FIG. 3 | Mature humanized light chain of LDP-02 |
| 6 | FIG. 4 | Generic human kappa light chain constant region |
| 7 | FIG. 4 | Generic murine kappa light chain constant region |
| 8 | Referenced on page 31 SYWMH | CDR1 of heavy chain mouse ACT-1 antibody |
| 9 | Referenced on page 31 EIDPSESNTNYNQKFKG | CDR2 of heavy chain mouse ACT-1 antibody |
| 10 | Referenced on page 31 GGYDGWDYAIDY | CDR3 of heavy chain mouse ACT-1 antibody |
| 11 | Referenced on page 31 RSSQSLAKSYGNTYLS | CDR1 of light chain mouse ACT-1 antibody |
| 12 | Referenced on page 31 GISNRFS | CDR2 of light chain mouse ACT-1 antibody |
| 13 | Referenced on page 31 LQGTHQPYT | CDR3 of light chain mouse ACT-1 antibody |
| 14 | FIG. 7 | human GM607 CL antibody kappa light chain variable region |
| 15 | FIG. 7 | Human 21/28 CL antibody heavy chain variable region |

What is claimed is:

1. A stable liquid pharmaceutical formulation comprising an anti-α4β7 antibody at a concentration of about 150 mg/ml to about 180 mg/ml, citrate, at least one free amino acid, a buffering agent, and a surfactant, wherein the anti-α4β7 antibody is an IgG1 isotype comprising a light chain variable region comprising a CDR1 comprising SEQ ID NO: 11, a CDR2 comprising SEQ ID NO: 12, and a CDR3 comprising SEQ ID NO: 13, and comprising a heavy chain variable region comprising a CDR1 comprising SEQ ID NO:8, a CDR2 comprising SEQ ID NO: 9, and a CDR3 comprising SEQ ID NO: 10, and wherein the formulation has a pH of 6 to 7, and wherein the formulation has greater than or equal to 96% monomeric anti-α4β7 antibody as determined by size exclusion chromatography (SEC) after storage at 40° C. for 4 weeks.

2. The stable liquid pharmaceutical formulation of claim 1, wherein the molar ratio of the anti-α4β7 antibody to citrate is about 1:4 to about 1:100.

3. The stable liquid pharmaceutical formulation of claim 1, wherein said free amino acid is selected from the group consisting of histidine, alanine, arginine, glycine, and glutamic acid.

4. The stable liquid pharmaceutical formulation of claim 1, wherein the molar ratio of citrate to the surfactant is about 3:1 to about 156:1.

5. The stable liquid pharmaceutical formulation of claim 1, wherein said surfactant is polysorbate 80.

6. A stable liquid pharmaceutical formulation comprising an anti-α4β7 antibody at a concentration of about 150 mg/ml to about 180 mg/ml, citrate, histidine, arginine, and polysorbate 80, wherein the anti-α4β7 antibody comprises a light chain variable region comprising a CDR1 comprising SEQ ID NO: 11, a CDR2 comprising SEQ ID NO: 12, and a CDR3 comprising SEQ ID NO: 13, and comprises a heavy chain variable region comprising a CDR1 comprising SEQ ID NO:8, a CDR2 comprising SEQ ID NO: 9, and a CDR3 comprising SEQ ID NO: 10, and wherein the formulation has greater than or equal to 96% monomeric anti-α4β7 antibody as determined by size exclusion chromatography (SEC) after storage at 40° C. for 4 weeks.

7. The stable liquid pharmaceutical formulation of claim 1, wherein said antibody is vedolizumab.

8. The stable liquid pharmaceutical formulation of claim 6, wherein said antibody is vedolizumab.

9. The stable liquid pharmaceutical formulation of claim 1, wherein the concentration of citrate is 20 mM to 30 mM.

10. The stable liquid pharmaceutical formulation of claim 1, wherein said free amino acid is arginine at a concentration of 50 mM to 150 mM.

11. The stable liquid pharmaceutical formulation of claim 1, wherein the buffering agent is histidine.

12. The stable liquid pharmaceutical formulation of claim 11, wherein the concentration of histidine is 25 mM to 65 mM.

13. The stable liquid pharmaceutical formulation of claim 1, wherein the heavy chain variable region comprises amino acids 20-140 of SEQ ID NO:2 and the light chain variable region comprises amino acids 20-131 of SEQ ID NO:4.

14. The stable liquid pharmaceutical formulation of claim 1, wherein said formulation has a pH between 6.2 and 6.8.

15. The stable liquid pharmaceutical formulation of claim 1, wherein there is ≤2.5% aggregate antibody.

16. A stable liquid pharmaceutical formulation comprising about 140 mg/ml to about 170 mg/ml of an anti-α4β7 antibody, about 20 mM to about 30 mM citrate, about 10 mM to about 75 mM histidine, about 0.01% to about 0.5% (w/v) polysorbate 80, and about 50 mM to about 150 mM arginine, wherein the anti-α4β7 antibody is an IgG1 isotype comprising a light chain variable region comprising a CDR1 comprising SEQ ID NO:11, a CDR2 comprising SEQ ID NO: 12, and a CDR3 comprising SEQ ID NO: 13, and comprising a heavy chain variable region comprising a CDR1 comprising SEQ ID NO:8, a CDR2 comprising SEQ ID NO: 9, and a CDR3 comprising SEQ ID NO: 10, and wherein the formulation has greater than or equal to 96% monomeric anti-α4β7 antibody as determined by size exclusion chromatography (SEC) after storage at 40° C. for 4 weeks.

17. The stable liquid pharmaceutical formulation of claim 16, wherein the heavy chain variable region comprises amino acids 20-140 of SEQ ID NO:2 and the light chain variable region comprises amino acids 20-131 of SEQ ID NO:4.

18. The stable liquid pharmaceutical formulation of claim 16, wherein said antibody is vedolizumab.

19. The stable liquid pharmaceutical formulation of claim 1, wherein after 12 months at 5° C. the stable liquid pharmaceutical formulation has less than about 1.0% antibody aggregate formation.

20. The stable liquid pharmaceutical formulation of claim 6, wherein the heavy chain variable region comprises amino acids 20-140 of SEQ ID NO:2 and the light chain variable region comprises amino acids 20-131 of SEQ ID NO:4.

21. The stable liquid pharmaceutical formulation of claim 6, comprising a dose of 108 mg of the anti-α4β7 antibody.

22. The stable liquid pharmaceutical formulation of claim 1, comprising a dose of 108 mg of the anti-α4β7 antibody.

23. The stable liquid pharmaceutical formulation of claim 1, wherein the molar ratio of the surfactant to the anti-α4β7 antibody is 0.7:1 to 2.0:1.

24. The stable liquid pharmaceutical formulation of claim 16, comprising a dose of 108 mg of the anti-α4β7 antibody.

25. The stable liquid pharmaceutical formulation of claim 6, comprising 150 mg/ml to 170 mg/ml of the anti-α4β7 antibody, wherein the antibody is an IgG1 isotype.

26. The stable liquid pharmaceutical formulation of claim 6, wherein the concentration of histidine is about 25 mM to about 50 mM.

27. The stable liquid pharmaceutical formulation of claim 26, wherein the concentration of arginine is 50 mM to 150 mM.

28. The stable liquid pharmaceutical formulation of claim 26, wherein the concentration of citrate is about 5 mM to about 50 mM.

29. The stable liquid pharmaceutical formulation of claim 5, comprising 0.1% to 0.3% (w/v) polysorbate 80.

* * * * *